US009549941B2

(12) United States Patent
Cleary et al.

(10) Patent No.: US 9,549,941 B2
(45) Date of Patent: *Jan. 24, 2017

(54) COMPOSITIONS AND METHODS FOR TREATING HEPATITIS C VIRUS

(71) Applicant: GILEAD PHARMASSET LLC, Foster City, CA (US)

(72) Inventors: Darryl G. Cleary, Chapel Hill, NC (US); Charles J. Reynolds, Greenville, NC (US); Miriam Michelle Berrey, Durham, NC (US); Robert G. Hindes, Skillman, NJ (US); William T. Symonds, San Francisco, CA (US); Adrian S. Ray, Redwood City, CA (US); Hongmei Mo, Palo Alto, CA (US); Christy M. Hebner, Belmont, CA (US); Reza Oliyai, Burlingame, CA (US); Vahid Zia, San Carlos, CA (US); Dimitrios Stefanidis, Mountain View, CA (US); Rowchanak Pakdaman, San Carlos, CA (US); Melissa Jean Casteel, Burlingame, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/538,736

(22) Filed: Nov. 11, 2014

(65) Prior Publication Data

US 2015/0150896 A1 Jun. 4, 2015

Related U.S. Application Data

(63) Continuation of application No. 13/686,664, filed on Nov. 27, 2012, now Pat. No. 8,889,159, which is a
(Continued)

(51) Int. Cl.
A61K 31/685 (2006.01)
A61K 31/7056 (2006.01)
(Continued)

(52) U.S. Cl.
CPC ......... *A61K 31/7072* (2013.01); *A61K 9/2009* (2013.01); *A61K 9/2013* (2013.01);
(Continued)

(58) Field of Classification Search
None
See application file for complete search history.

(56) References Cited

U.S. PATENT DOCUMENTS 3,798,209 A   3/1974 Witkowski et al.
3,852,267 A   12/1974 Meyer, Jr. et al.
(Continued)

FOREIGN PATENT DOCUMENTS

CA   2682230   10/2008
CN   101108870   1/2008
(Continued)

OTHER PUBLICATIONS

Jen et al., "Ribavirin dosing in chronic hepatitis C: application of population pharmacokinetic-pharmacodynamics models", Clinical Pharmacology & Therapeutics, vol. 72, #4, pp. 349-361 (2002).*
(Continued)

*Primary Examiner* — Ernst V Arnold
*Assistant Examiner* — Kyung Sook Chang
(74) *Attorney, Agent, or Firm* — Sheppard Mullin Richter & Hampton LLP

(57) ABSTRACT

Disclosed herein are a composition and unit dosage form for the treatment of hepatitis C virus (HCV) infection comprising GS-7977 and at least one pharmaceutically acceptable excipient, as well as methods for making said composition and unit dosage form. Also disclosed herein is a method of
(Continued)

treating a subject, preferably a human, infected with hepatitis C virus, said method comprising administering to the subject for a time period an effective amount of GS-7977 and an effective amount of ribavirin. In one aspect, the method comprises administering to the subject an interferon-free treatment regimen comprising an effective amount of GS-7977 and an effective amount of ribavirin. In a particular aspect, the method is sufficient to produce an undetectable amount of HCV RNA in the subject for at least 12 weeks after the end of the time period.

23 Claims, 3 Drawing Sheets

Related U.S. Application Data continuation-in-part of application No. 13/661,509, filed on Oct. 26, 2012, now abandoned, and a continuation-in-part of application No. PCT/US2012/055621, filed on Sep. 14, 2012.

(60) Provisional application No. 61/564,500, filed on Nov. 29, 2011, provisional application No. 61/707,459, filed on Sep. 28, 2012.

(51) Int. Cl.
| | |
|---|---|
| A61K 31/7068 | (2006.01) |
| A61K 31/4196 | (2006.01) |
| A61K 31/7072 | (2006.01) |
| A61K 9/20 | (2006.01) |
| A61K 31/513 | (2006.01) |
| A61K 31/664 | (2006.01) |
| A61K 31/675 | (2006.01) |

(52) U.S. Cl.
CPC ........ *A61K 9/2054* (2013.01); *A61K 31/4196* (2013.01); *A61K 31/513* (2013.01); *A61K 31/664* (2013.01); *A61K 31/675* (2013.01); *A61K 31/685* (2013.01); *A61K 31/7056* (2013.01); *A61K 31/7068* (2013.01)

(56) References Cited

U.S. PATENT DOCUMENTS

| | | |
|---|---|---|
| RE29,835 E | 11/1978 | Witkowski et al. |
| 4,814,477 A | 3/1989 | Wijnberg et al. |
| 4,957,924 A | 9/1990 | Beauchamp |
| 5,026,687 A | 6/1991 | Yarchoan et al. |
| 5,118,820 A | 6/1992 | Hertel |
| 5,149,794 A | 9/1992 | Yatvin et al. |
| 5,157,027 A | 10/1992 | Biller et al. |
| 5,192,549 A | 3/1993 | Barenolz et al. |
| 5,194,654 A | 3/1993 | Hostetler et al. |
| 5,210,015 A | 5/1993 | Gelfand et al. |
| 5,223,263 A | 6/1993 | Hostetler et al. |
| 5,256,641 A | 10/1993 | Yatvin et al. |
| 5,256,798 A | 10/1993 | Chou et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou et al. |
| 5,462,724 A | 10/1995 | Schinazi et al. |
| 5,463,092 A | 10/1995 | Hostetler et al. |
| 5,496,546 A | 3/1996 | Wang et al. |
| 5,538,848 A | 7/1996 | Livak et al. |
| 5,538,865 A | 7/1996 | Reyes et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,610,054 A | 3/1997 | Draper |
| 5,633,358 A | 5/1997 | Gruetzke et al. |
| 5,633,388 A | 5/1997 | Diana et al. |
| 5,676,942 A | 10/1997 | Testa et al. |
| 5,703,058 A | 12/1997 | Schinazi et al. |
| 5,711,944 A | 1/1998 | Gilbert et al. |
| 5,725,859 A | 3/1998 | Omer |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,869,253 A | 2/1999 | Draper |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,156,501 A | 12/2000 | McGall et al. |
| 6,180,134 B1 | 1/2001 | Zalipsky et al. |
| 6,232,300 B1 | 5/2001 | Schinazi et al. |
| 6,239,159 B1 | 5/2001 | Brown et al. |
| 6,348,587 B1 | 2/2002 | Schinazi et al. |
| 6,372,883 B1 | 4/2002 | Attwood et al. |
| 6,391,859 B1 | 5/2002 | Schinazi et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan et al. |
| 6,455,690 B1 | 9/2002 | Tam et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,555,677 B2 | 4/2003 | Petrillo et al. |
| 6,573,248 B2 | 6/2003 | Ramasamy et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,846,810 B2 | 1/2005 | Martin et al. |
| 6,897,201 B2 | 5/2005 | Boyer et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,962,991 B2 | 11/2005 | Dempcy et al. |
| 7,018,985 B1 | 3/2006 | Boyer et al. |
| 7,018,989 B2 | 3/2006 | McGuigan et al. |

(56) References Cited

U.S. PATENT DOCUMENTS

| | | |
|---|---|---|
| 7,081,449 B2 | 7/2006 | Pietrzkowski et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,217,523 B2 | 5/2007 | Wagner |
| 7,268,119 B2 | 9/2007 | Cook et al. |
| 7,307,065 B2 | 12/2007 | Schinazi et al. |
| 7,323,453 B2 | 1/2008 | Bhat et al. |
| 7,365,057 B2 | 4/2008 | LaColla et al. |
| 7,390,791 B2 | 6/2008 | Becker et al. |
| 7,429,572 B2 | 9/2008 | Clark |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | LaColla et al. |
| 7,754,699 B2 | 7/2010 | Chun et al. |
| 7,820,380 B2 | 10/2010 | Huang |
| 7,879,815 B2 | 2/2011 | MacCoss et al. |
| 7,964,580 B2 | 6/2011 | Sofia et al. |
| 8,148,349 B2 | 4/2012 | Meppen et al. |
| 8,173,621 B2 | 5/2012 | Du et al. |
| 8,334,270 B2 | 12/2012 | Sofia et al. |
| 8,415,322 B2 | 4/2013 | Clark |
| 8,466,159 B2 | 6/2013 | Bernstein et al. |
| 8,551,973 B2 | 10/2013 | Bao et al. |
| 8,580,765 B2 | 11/2013 | Sofia et al. |
| 2001/0034440 A1 | 10/2001 | Shepard et al. |
| 2001/0038833 A1 | 11/2001 | Rybak et al. |
| 2002/0008241 A1 | 1/2002 | Edmond et al. |
| 2002/0058635 A1 | 5/2002 | Averett |
| 2002/0147160 A1 | 10/2002 | Bhat et al. |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0096364 A1 | 5/2003 | Baker et al. |
| 2003/0119752 A1 | 6/2003 | Farmer et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0176433 A1 | 9/2003 | Beaulieu et al. |
| 2003/0187018 A1 | 10/2003 | Llinas-Brunet et al. |
| 2003/0207922 A1 | 11/2003 | Neuner et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0024190 A1 | 2/2004 | Beaulieu et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0142989 A1 | 7/2004 | Finzel et al. |
| 2004/0142993 A1 | 7/2004 | Battistini et al. |
| 2004/0167140 A1 | 8/2004 | Schinazi et al. |
| 2004/0171570 A1 | 9/2004 | Allerson et al. |
| 2004/0191824 A1 | 9/2004 | Dempcy et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0026160 A1 | 2/2005 | Allerson et al. |
| 2005/0026853 A1 | 2/2005 | Mekouar et al. |
| 2005/0031588 A1 | 2/2005 | Sommadossi et al. |
| 2005/0043390 A1 | 2/2005 | Bravi et al. |
| 2005/0069522 A1 | 3/2005 | Colonno et al. |
| 2005/0075309 A1 | 4/2005 | Storer et al. |
| 2005/0080034 A1 | 4/2005 | Standring et al. |
| 2005/0090432 A1 | 4/2005 | McPhee et al. |
| 2005/0090660 A1 | 4/2005 | Watanabe et al. |
| 2005/0096364 A1 | 5/2005 | Romine et al. |
| 2005/0098125 A1 | 5/2005 | Hathaway et al. |
| 2005/0124532 A1 | 6/2005 | Sommadossi et al. |
| 2005/0130923 A1 | 6/2005 | Bhat et al. |
| 2005/0130931 A1 | 6/2005 | Boyer et al. |
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0215614 A1 | 9/2005 | Singh et al. |
| 2005/0227947 A1 | 10/2005 | Chen et al. |
| 2005/0228013 A1 | 10/2005 | Thurkauf et al. |
| 2005/0261237 A1 | 11/2005 | Boojamra et al. |
| 2005/0267018 A1 | 12/2005 | Blatt et al. |
| 2006/0003951 A1 | 1/2006 | Mekouar et al. |
| 2006/0004063 A1 | 1/2006 | Finzel et al. |
| 2006/0014943 A1 | 1/2006 | Dempcy et al. |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0046983 A1 | 3/2006 | Hudyma et al. |
| 2006/0079478 A1 | 4/2006 | Boojamra et al. |
| 2006/0094706 A1 | 5/2006 | Paruch et al. |
| 2006/0110724 A1 | 5/2006 | Burkhardt, III. et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0166964 A1 | 7/2006 | Hudyma et al. |
| 2006/0194749 A1 | 8/2006 | Keicher et al. |
| 2006/0199783 A1 | 9/2006 | Wang et al. |
| 2006/0234962 A1 | 10/2006 | Olsen et al. |
| 2006/0241064 A1 | 10/2006 | Roberts et al. |
| 2006/0276405 A1 | 12/2006 | Albrecht |
| 2006/0276511 A1 | 12/2006 | Serrano-Wu et al. |
| 2006/0287300 A1 | 12/2006 | Klein et al. |
| 2006/0293306 A1 | 12/2006 | Beaulieu et al. |
| 2007/0004669 A1 | 1/2007 | Carroll et al. |
| 2007/0015905 A1 | 1/2007 | LaColla et al. |
| 2007/0024277 A1 | 2/2007 | Cech et al. |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0054842 A1 | 3/2007 | Blatt et al. |
| 2007/0059360 A1 | 3/2007 | Jaiswal et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0123484 A1 | 5/2007 | Bhat et al. |
| 2007/0135363 A1 | 6/2007 | Cook et al. |
| 2007/0142380 A1 | 6/2007 | Beaulieu et al. |
| 2007/0155716 A1 | 7/2007 | Simmen et al. |
| 2007/0197463 A1 | 8/2007 | Chun et al. |
| 2007/0197478 A1 | 8/2007 | Jones et al. |
| 2007/0225249 A1 | 9/2007 | Shi |
| 2007/0231318 A1 | 10/2007 | Saha et al. |
| 2007/0232627 A1 | 10/2007 | Betebenner et al. |
| 2007/0232645 A1 | 10/2007 | Rockway et al. |
| 2007/0265222 A1 | 11/2007 | MacCoss et al. |
| 2007/0265262 A1 | 11/2007 | Schmitz et al. |
| 2007/0274947 A1 | 11/2007 | Young et al. |
| 2007/0275912 A1 | 11/2007 | Bhat et al. |
| 2007/0275930 A1 | 11/2007 | Gentles et al. |
| 2007/0275947 A1 | 11/2007 | Bergstrom |
| 2008/0021047 A1 | 1/2008 | Butora et al. |
| 2008/0050336 A1 | 2/2008 | Bachand et al. |

(56) References Cited

U.S. PATENT DOCUMENTS

| | | |
|---|---|---|
| 2008/0070861 A1 | 3/2008 | Clark |
| 2008/0108617 A1 | 5/2008 | Desai et al. |
| 2008/0146788 A1 | 6/2008 | Bhat et al. |
| 2008/0182863 A1 | 7/2008 | Simmen et al. |
| 2008/0253995 A1 | 10/2008 | Clark |
| 2008/0260826 A1* | 10/2008 | Birudaraj ............. A61K 9/2031 424/474 |
| 2008/0280842 A1 | 11/2008 | MacCoss et al. |
| 2009/0004135 A1 | 1/2009 | Clark |
| 2009/0036666 A1 | 2/2009 | Clark |
| 2009/0041716 A1 | 2/2009 | Kim et al. |
| 2009/0062311 A1 | 3/2009 | Simmen et al. |
| 2009/0105302 A1 | 4/2009 | Simmen et al. |
| 2009/0137521 A1 | 5/2009 | Hamilton et al. |
| 2009/0156595 A1 | 6/2009 | Raboisson et al. |
| 2009/0176732 A1 | 7/2009 | Beigelman et al. |
| 2009/0233879 A1 | 9/2009 | Reddy et al. |
| 2009/0269305 A1 | 10/2009 | Seiwert et al. |
| 2009/0280084 A1 | 11/2009 | Schinazi et al. |
| 2009/0281140 A1 | 11/2009 | Simmen et al. |
| 2009/0281141 A1 | 11/2009 | Simmen et al. |
| 2009/0291902 A1 | 11/2009 | Cottrell et al. |
| 2009/0306007 A1 | 12/2009 | Wagner |
| 2010/0015090 A1 | 1/2010 | Tung et al. |
| 2010/0016251 A1 | 1/2010 | Sofia et al. |
| 2010/0022468 A1 | 1/2010 | Meppen et al. |
| 2010/0029008 A1 | 2/2010 | Rojas Stutz et al. |
| 2010/0035835 A1 | 2/2010 | Narjes et al. |
| 2010/0081628 A1 | 4/2010 | Du et al. |
| 2010/0137576 A1 | 6/2010 | Stec et al. |
| 2010/0152128 A1 | 6/2010 | Attenni et al. |
| 2010/0173863 A1 | 7/2010 | Schinazi et al. |
| 2010/0226885 A1 | 9/2010 | Albrecht et al. |
| 2010/0227801 A1 | 9/2010 | Hopkins |
| 2010/0234316 A1 | 9/2010 | MacCoss et al. |
| 2010/0267785 A1 | 10/2010 | Wu et al. |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0316594 A1 | 12/2010 | Sommadossi et al. |
| 2011/0015146 A1 | 1/2011 | Sophia et al. |
| 2011/0020272 A1 | 1/2011 | Schubert |
| 2011/0124592 A1 | 5/2011 | McGuigan et al. |
| 2011/0237621 A1 | 9/2011 | Simmen et al. |
| 2011/0245484 A1 | 10/2011 | Ross et al. |
| 2011/0251152 A1 | 10/2011 | Ross et al. |
| 2011/0257122 A1 | 10/2011 | Sofia et al. |
| 2012/0094284 A1 | 4/2012 | Lopatin et al. |
| 2012/0107278 A1 | 5/2012 | Berrey et al. |
| 2012/0245335 A1 | 9/2012 | Clark |
| 2012/0246335 A1 | 9/2012 | Clark |
| 2012/0251152 A1 | 10/2012 | Brewington et al. |
| 2013/0029929 A1 | 1/2013 | Sofia et al. |
| 2013/0102526 A1 | 4/2013 | Bernstein et al. |
| 2013/0102557 A1 | 4/2013 | Bernstein et al. |
| 2013/0102558 A1 | 4/2013 | Bernstein et al. |
| 2013/0109647 A1 | 5/2013 | Berrey et al. |
| 2013/0136776 A1 | 5/2013 | Cleary et al. |
| 2013/0137654 A1 | 5/2013 | Ross et al. |
| 2013/0165401 A1 | 6/2013 | Ross et al. |
| 2013/0165644 A1 | 6/2013 | Ross et al. |
| 2013/0288997 A1 | 10/2013 | Ross et al. |
| 2013/0310551 A1 | 11/2013 | Ross et al. |

FOREIGN PATENT DOCUMENTS

| | | |
|---|---|---|
| DE | 199 14 474 | 10/1999 |
| DE | 102008057284 | 5/2010 |
| EP | 0 180 276 | 5/1986 |
| EP | 0 350 287 | 1/1990 |
| EP | 1 828 217 | 9/2007 |
| EP | 1 881 001 | 1/2008 |
| EP | 2 097 430 | 9/2009 |
| EP | 2 124 555 | 12/2009 |
| EP | 2 207 786 | 3/2012 |
| JP | 5-238939 | 9/1993 |
| WO | WO-89/02733 | 4/1989 |
| WO | WO-90/00555 | 1/1990 |
| WO | WO-91/16920 | 11/1991 |
| WO | WO-91/18914 | 12/1991 |
| WO | WO-91/19721 | 12/1991 |
| WO | WO-93/00910 | 1/1993 |
| WO | WO-94/26273 | 11/1994 |
| WO | WO-95/13090 | 5/1995 |
| WO | WO-95/24185 | 9/1995 |
| WO | WO-96/15132 | 5/1996 |
| WO | WO-96/32403 | 10/1996 |
| WO | WO-97/12033 | 4/1997 |
| WO | WO-97/36554 | 10/1997 |
| WO | WO-98/16184 | 4/1998 |
| WO | WO-98/17679 | 4/1998 |
| WO | WO-98/22496 | 5/1998 |
| WO | WO-99/07734 | 2/1999 |
| WO | WO-99/15194 | 4/1999 |
| WO | WO-99/32139 | 7/1999 |
| WO | WO-99/32140 | 7/1999 |
| WO | WO-99/43691 | 9/1999 |
| WO | WO-99/59621 | 11/1999 |
| WO | WO 99/64016 | 12/1999 |
| WO | WO-00/06529 | 2/2000 |
| WO | WO-00/09531 | 2/2000 |
| WO | WO-00/37110 | 6/2000 |
| WO | WO-01/09121 | 2/2001 |
| WO | WO-01/32153 | 5/2001 |
| WO | WO-01/60315 | 8/2001 |
| WO | WO-01/79246 | 10/2001 |
| WO | WO-01/81359 | 11/2001 |
| WO | WO-01/90121 | 11/2001 |
| WO | WO-01/91737 | 12/2001 |
| WO | WO-01/92282 | 12/2001 |
| WO | WO-01/96353 | 12/2001 |
| WO | WO-02/08187 | 1/2002 |
| WO | WO-02/08198 | 1/2002 |
| WO | WO-02/08251 | 1/2002 |
| WO | WO-02/08256 | 1/2002 |
| WO | WO-02/18404 | 3/2002 |
| WO | WO-02/32414 | 4/2002 |
| WO | WO-02/32920 | 4/2002 |
| WO | WO 02/48116 | 6/2002 |
| WO | WO 02/48157 | 6/2002 |
| WO | WO-02/48165 | 6/2002 |
| WO | WO-02/48172 | 6/2002 |
| WO | WO-02/057287 | 7/2002 |
| WO | WO-02/057425 | 7/2002 |
| WO | WO-02/060926 | 8/2002 |
| WO | WO-02/100415 | 12/2002 |
| WO | WO-03/000713 | 1/2003 |
| WO | WO-03/006490 | 1/2003 |
| WO | WO-03/010141 | 2/2003 |
| WO | WO-03/024461 | 3/2003 |
| WO | WO 03/026589 | 4/2003 |
| WO | WO-03/037895 | 5/2003 |
| WO | WO-03/051899 | 6/2003 |
| WO | WO-03/053989 | 7/2003 |
| WO | WO-03/061576 | 7/2003 |
| WO | WO-03/062256 | 7/2003 |
| WO | WO-03/064456 | 8/2003 |
| WO | WO-03/068244 | 8/2003 |
| WO | WO-03/101993 | 12/2003 |
| WO | WO-03/104250 | 12/2003 |
| WO | WO-03/105770 | 12/2003 |
| WO | WO-03/106477 | 12/2003 |
| WO | WO-2004/000858 | 12/2003 |
| WO | WO-2004/002422 | 1/2004 |
| WO | WO-2004/002940 | 1/2004 |
| WO | WO-2004/002944 | 1/2004 |
| WO | WO-2004/002977 | 1/2004 |
| WO | WO-2004/002999 | 1/2004 |
| WO | WO-2004/003000 | 1/2004 |
| WO | WO-2004/003138 | 1/2004 |
| WO | WO-2004/007512 | 1/2004 |
| WO | WO-2004/009020 | 1/2004 |
| WO | WO-2004/009610 | 1/2004 |

(56) References Cited

FOREIGN PATENT DOCUMENTS

| | | |
|---|---|---|
| WO | WO-2004/011478 | 2/2004 |
| WO | WO-2004/014313 | 2/2004 |
| WO | WO-2004/014852 | 2/2004 |
| WO | WO-2004/035571 | 4/2004 |
| WO | WO-2004/041201 | 5/2004 |
| WO | WO-2004/046331 | 6/2004 |
| WO | WO-2004/065367 | 8/2004 |
| WO | WO 2004/069149 | 8/2004 |
| WO | WO-2004/069149 | 8/2004 |
| WO | WO-2004/080466 | 9/2004 |
| WO | WO-2004/094452 | 11/2004 |
| WO | WO-2004/096210 | 11/2004 |
| WO | WO-2004/096234 | 11/2004 |
| WO | WO-2004/096235 | 11/2004 |
| WO | WO-2004/096286 | 11/2004 |
| WO | WO-2004/106356 | 12/2004 |
| WO | WO-2005/002626 | 1/2005 |
| WO | WO-2005/003147 | 1/2005 |
| WO | WO-2005/007810 | 1/2005 |
| WO | WO-2005/009418 | 2/2005 |
| WO | WO-2005/102327 | 2/2005 |
| WO | WO-2005/020884 | 3/2005 |
| WO | WO-2005/021568 | 3/2005 |
| WO | WO-2005/028502 | 3/2005 |
| WO | WO-2005/037214 | 4/2005 |
| WO | WO-2005/067900 | 7/2005 |
| WO | WO-2005/072361 | 8/2005 |
| WO | WO-2005/082144 | 9/2005 |
| WO | WO-2005/087788 | 9/2005 |
| WO | WO-2005/095403 | 10/2005 |
| WO | WO-2005/103045 | 11/2005 |
| WO | WO-2005/123087 | 12/2005 |
| WO | WO-2006/000922 | 1/2006 |
| WO | WO-2006/012078 | 2/2006 |
| WO | WO-2006/012440 | 2/2006 |
| WO | WO-2006/020082 | 2/2006 |
| WO | WO-2006/029081 | 3/2006 |
| WO | WO-2006/031725 | 3/2006 |
| WO | WO-2006/035061 | 4/2006 |
| WO | WO-2006/037028 | 4/2006 |
| WO | WO-2006/050161 | 5/2006 |
| WO | WO-2006/063149 | 6/2006 |
| WO | WO-2006/063717 | 6/2006 |
| WO | WO-2006/065335 | 6/2006 |
| WO | WO-2006/065590 | 6/2006 |
| WO | WO-2006/067606 | 6/2006 |
| WO | WO-2006/093801 | 9/2006 |
| WO | WO-2006/100310 | 9/2006 |
| WO | WO-2006/116557 | 11/2006 |
| WO | WO-2006/120251 | 11/2006 |
| WO | WO-2006/120252 | 11/2006 |
| WO | WO-2006/121820 | 11/2006 |
| WO | WO-2007/002602 | 1/2007 |
| WO | WO-2007/014920 | 2/2007 |
| WO | WO-2007/014921 | 2/2007 |
| WO | WO-2007/014922 | 2/2007 |
| WO | WO-2007/014925 | 2/2007 |
| WO | WO-2007/014926 | 2/2007 |
| WO | WO-2007/015824 | 2/2007 |
| WO | WO-2007/020193 | 2/2007 |
| WO | WO-2007/027248 | 3/2007 |
| WO | WO-2007/039142 | 4/2007 |
| WO | WO-2007/039145 | 4/2007 |
| WO | WO-2007/058397 | 5/2007 |
| WO | WO 2007/058397 | 5/2007 |
| WO | WO-2007/065829 | 6/2007 |
| WO | WO-2007/070556 | 6/2007 |
| WO | WO-2007/076034 | 7/2007 |
| WO | WO-2007/088148 | 8/2007 |
| WO | WO-2007/092000 | 8/2007 |
| WO | WO-2007/093901 | 8/2007 |
| WO | WO-2007/095269 | 8/2007 |
| WO | WO-2008/010921 | 1/2008 |
| WO | WO-2008/045419 | 4/2008 |
| WO | WO-2008/048128 | 4/2008 |
| WO | WO-2008/062206 | 5/2008 |
| WO | WO-2008/079206 | 7/2008 |
| WO | WO-2008/082601 | 7/2008 |
| WO | WO-2008/085508 | 7/2008 |
| WO | WO-2008/106130 | 9/2008 |
| WO | WO-2008/124148 | 10/2008 |
| WO | WO-2008121634 | 10/2008 |
| WO | WO-2008/142055 | 11/2008 |
| WO | WO-2009/029844 | 3/2009 |
| WO | WO-2009/038663 | 3/2009 |
| WO | WO-2009/052287 | 4/2009 |
| WO | WO-2009/115893 | 9/2009 |
| WO | WO-2009/120878 | 10/2009 |
| WO | WO-2009/129120 | 10/2009 |
| WO | WO-2009/132123 | 10/2009 |
| WO | WO-2009/152095 | 12/2009 |
| WO | WO-2010/042834 | 4/2010 |
| WO | WO-2010/075517 | 7/2010 |
| WO | WO-2010/075549 | 7/2010 |
| WO | WO-2010/075554 | 7/2010 |
| WO | WO-2010/080878 | 7/2010 |
| WO | WO-2010/081082 | 7/2010 |
| WO | WO-2010/112203 | 10/2010 |
| WO | WO-2010/135569 | 11/2010 |
| WO | WO-2011/035231 | 3/2011 |
| WO | WO-2011/123645 | 10/2011 |
| WO | WO-2011/123672 | 10/2011 |
| WO | WO-2012/130862 | 10/2012 |
| WO | WO-2013/059630 | 4/2013 |
| WO | WO-2013/059638 | 4/2013 |

OTHER PUBLICATIONS

Abonyi et al., "Ribavirin in the Treatment of Hepatitis C," Anticancer Res. (2005) 25:1315-1320.
Abraham et al., "Synthesis and Biological Activity of Aromatic Amino Acid Phosphoramidates of 5-fluoro-2'-1 deoxyuridine and 1-beta-Arabinofuranosylcytosine: Evidence of Phosphoramidase Activity," J. Med. Chem., vol. 39, No. 23, pp. 4569-4575, (1996).
Abraham et al., "Synthesis, Biological Activity and Decomposition Studies of Amino Acid Phosphomonoester Amidates of Acyclovir," Nucleotides and Nucleic Acids, vol. 16, No. 10, pp. 2079-2092 (1997).
Afdhal et al., Hepatology (2011) 53(1): 336-345.
Alan Franciscus, "Hepatitis C Treatments in Current Clinical Development", HCV Advocate, pp. 1-26 (Mar. 2010).
Aquaro et al., "Activities of Masked 2',3'-Dideoxynucleoside Monophosphate Derivaties Against Human Immunodeficiency Virus in Resting Macrophages," Antimicrobial Agents and Chemotherapy, vol. 44, No. 1, pp. 173-177 (2000).
Asif et al., "Pharmacokinetics of the Antiviral Agent B-D-2'-Deoxy-2'-Fluoro-2'-C-Methylcytidine in Rhesus Monkeys," Antimicrobial Agents and Chemotherapy, vol. 51, No. 8, pp. 2877-2882 (2007).
Asselah et al., Gut (2009) 58: 846-858.
Asselah et al., J. Hepatology (2012) 56: 527-532.
Balzarini et al., "Mechanism of anti-HIV action of masked alaninyl d4t-MP derivatives," Proc. Natl. Acad. Sci., vol. 93, pp. 7295-7299 (1996).
Banker et al., "Prodrugs," Modern Pharmaceutics, Third Edition, Revised and Expanded, pp. 451 and 596 (1996).
Bartenschlager et al., "Kinetic and Structural Analyses of Hepatitis C Virus Polyprotein Processing," J. Virol., vol. 68, No. 8, pp. 5045-5055 (1994).
Bartenschlager et al., "Nonstructural Protein 3 of the Hepatitis C Virus Encodes a Serine-Type Proteinase Required for Cleavage at the NS3/4 and NS4/5 Junctions," J. Virol., vol. 67, No. 7, pp. 3835-3844 (1993).
Baschang et al., "Neue Derivate von Thymidin-3',5'-cyclophosphat," Angew. Chem., vol. 85, No. 1, pp. 44-45 (1973).
Battaglia et al., "Combination Therapy with Interferon and Ribavirin in the Treatment of Chronic Hepatitis C Infection," The Annals of Pharmacotherapy, vol. 34, No. 4, pp. 487-494 (2000).

(56) References Cited

OTHER PUBLICATIONS

Bazan et al., "Detection of a Trypsin-like Serine Protease Domain in Flaviviruses and Pestiviruses," Virology, vol. 171, pp. 637-639 (1989).

Beaulieu et al., "Inhibitors of the HGV NS5B polymerase: New hope for the treatment of hepatitis C infections," Current Opinion in Investigational Drugs, vol. 5, No. 8, pp. 838-850 (2004).

Behrens et al., "Identification and properties of the RNA-dependent RNA polymerase of hepatitis C virus," The EMBO Journal, vol. 15, No. 1, pp. 12-22 (1996).

Berenguer, M., "Hepatitis C virus in the transplant setting," Antiviral Therapy, vol. 3, Supplement 3, pp. 125-136 (1998).

Bhat et al., "Synthesis and Pharmacokinetic Properties of Nucleoside Analogues as Possible Inhibitors of HGV RNA Replication," (Oral Session V: Hepatitis C Virus, Flaviviruses), 16th International Conference on Antiviral Research, Abstract No. 120, p. A75 (Apr. 27-May 1, 2003).

Bodenheimer et al., "Tolerance and Efficacy of Oral Ribavirin Treatment of Chronic Hepatitis C: A Multicenter Trial," Hepatology (1997) 26(2):473-477.

Bonkovsky et al., "Comparative Effects of Different Doses of Ribavirin Plus Interferon-alfa2b for Therapy of Chronic Hepatitis C: Results of a Controlled, Randomized Trial," Digestive Dis. & Sci. (2001) 46(10):2051-2059.

Bourliere, M., "Chronic hepatitis C: Treatments of the future," Clin. Res. Hepatology & Gastroenterology (2011) 35: S84-S95.

Broeders et al., "A 400- and 600-Mhz ¹H NMR Confromational Study on Nucleoside Cyclic 3', 5' PV-TBP Systems. Conformational Transmission Induces Diequatorial Orientation of the 3', 5'-Dioxaphosphorinane Ring in a Nonchair Confirmation," J. Am. Chem. Soc., vol. 112, No. 21, pp. 7475-7482 (1990).

Byrn et al., "Pharmaceutical Solids: A Strategic Approach to Regulatory Considerations," Pharmaceutical Research, vol. 12, No. 7., pp. 945-954 (1995) Cahard.

Cahard, Dominique et al., "Aryloxy Phosphoramidate Triesters as Pro-Tides," Mini-Reviews in Medicinal Chemistry (2004), 4, 371-381.

Calisher et al.. "Antigenic Relationships between Flaviviruses as Determined by Cross-neutralization Tests with Polyclonal Antisera," J. Gen. Virol., vol. 70, pp. 37-43 (1989).

Carroll et al., "Nucleoside Analog Inhibitors of Hepatitis C Virus Replication," Infectious Disorders—Drug Targets, vol. 6, No. 1, pp. 17-29 (2006).

Chang et al., "Amino Acid Phosphoramidate Monoesters of 3'-Azido-3'-deoxythymidine: Relationship between Antiviral Potency and Intracellular Metabolism," J. Med. Chem., vol. 44, No. 2, pp. 223-231 (2001).

Chapman et al., "Practical Synthesis, Separation, and Stereochemical Assignment of the PMPA Pro-Drug GS-7340," Nucleosides, Nucleotides & Nucleic Acids, vol. 20, No. 4-7, pp. 621-628 (2001).

Chapman et al., "Purification of PMPA Amidate Prodrugs by SMB Chromatography and X-Ray Crystallography of the Diastereomerically Pure GS-7340," Nucleosides, Nucleotides & Nucleic Acids, vol. 20, No. 4-7, pp. 1085-1090 (2001) 22.

Chawla et al., "Challenges in Polymorphism of Pharmaceuticals," CRIPS, vol. 5, No. 1, pp. 9-12 (2004).

Chem Ello et al., "The Effect of Interferon Alfa and Ribavirin Combination Therapy in Naive Patients with Chronic Hepatitis C," J. Hepatology (1995) 23(Suppl. 2):8-12.

Chen et al., "In Vivo Pharmacokinetics and Metabolism of Anti-Human Immunodeficiency Virus Agent D4t-5'-[P-Bromophenyl Methoxyalaninyl Phosphate] (Sampidine) in Mice," Drug Metabolism and Disposition, vol. 29, No. 7, pp. 1035-1041 (2001).

Chen et al., "Metabolism of Stavudine-5'-[P-Bromophenyl Methoxyalaninyl Phosphate], Stampidine, in Mice, Dogs, and Cats," Drug Metabolism and Disposition, vol. 30, No. 12, pp. 1523-1531 (2002).

Chou et al., "Evidence that Human Histidine Triad Nucleotide Binding Protein 3 (Hint3) is a Distinct Branch of the Histidine Triad (HIT) Superfamily," J. Mol. Biol., vol. 373, pp. 978-989 (2007).

Chou et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, vol. 4, No. 2, pp. 208-217 (2006).

Chu et al., "Isolation and Structure of SCH 351633: A Novel Hepatitis C Virus (HGV) NS3 Protease Inhibitor from the Fungus Penicillium Griseofulvum," Bioorg. & Med. Chem. Lett., vol. 9, pp. 1949-1952 (1999).

Chu et al., "Structure of Sch 68631: A New Hepatitis C Virue Proteinase Inhibitor from *Streptomyces sp*." Tel. Lett., vol. 37, No. 40, pp. 7229-7232 (1996).

Cihlar et al. "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, vol. 52, No. 2, pp. 655-665 (2008).

Clark et al., "Design, Synthesis, and Antiviral Activity of 2'-Deoxy-2'-ftuoro-2'-C-methylcytidine, a Potent Inhibitor of Hepatitis C Virus Replication," J. Med. Chem., vol. 48, No. 17, pp. 5504-5508 (2005).

Clark et al., Bioorg. Med. Chem. Lett. (2006) 16: 1712-1715.

Congiatu et al. "Molecular Modeling Studies on the Binding of Some Protides to the Putative Human Phosphoramidase Hint1 ," Nucleosides, Nucleotides and Nucleic Acids, vol. 26, pp. 1121-1124 (2007).

Congiatu et al., "Naphthyl Phosphoramidate Derivatives of BVdU as Potential Anticancer Agents: Design, Synthesis and Biological Evaluation," Nucleosides, Nucleotides, and Nucleic Acids, vol. 24, No. 5-7, pp. 485-489 (2005).

Cornprost et al., "The Effect of Renal Impairment and End Stage Renal Disease on the Single-Dose Pharmacokinetics of GS-7977," J. Hepatology, vol. 56:S433 (Abstract #1101) (2012).

Cornprost, M. et al., "The Effect of Renal Impairment and End Stage Renal Disease on the Single-Dose 10 Pharmacokinetics of GS-7977," Presented at the 4 7th Annual Meeting of the European Association for the Study of the Liver (Apr. 18-22, 2012), Barcelona, Spain (Poster #1101).

Cotton R.G.H., et al., "Reactivity of cytosine and thymine in single-base-pair mismatches hydroxylamine and osmium tetroxide and its application to the study of mutations," Proc. Natl. Acad. Sci. USA (1988), vol. 85, pp. 4397-4401.

Cotton, R.G.H., et al., "Reactivity of cytosine and thymine in single-base-pair mismatches with hydroxylamine and osmium tetroxide and its application to the study of mutations," Proc. Natl. Acad. Sci. USA (1988), vol. 85, pp. 4397-4401.

Curley et al., "Synthesis and anti-HIV evaluation of some phosphoramidate derivatives of AZT: studies on the effect of chain elongation on biological activity," Antiviral Research, vol. 14, pp. 345-356 (1990).

Davis, G. L., "Current Therapy for Chronic Hepatitis C," Gastroenterology, vol. 118, No. 2, pp. S104-S114 (2000).

D'Cruz et al., "Stampidine: a selective oculo-genital microbicide," Journal of Antimicrobial Chemotherapy, vol. 56, pp. 10-19 (2005).

De Lombaert et al., "N-Phosphonomethyl Dipeptides and Their Phosphonate Prod rugs, a New Generation of Neutral Endopeptidase (NEP, EC 3.4.24.11) Inhibitors," J. Med. Chem., vol. 37, No. 4, pp. 498-511 (1994).

Di Bisceglie et al., "Ribavirin as Therapy for Chronic Hepatitis C," Annals of Internal Medicine (1995) 123(12): 897-903.

Dienstag and McHutchison Gastroenterology 2006 et al 130: 231-264.

Drontle et al., "Designing a Pronucleotide Stratagem: Lessons from Amino Acid Phosphoramidates of Anticancer and Antiviral Pyrimidines," MiniReviews in Medicinal Chemistry, vol. 4, No. 4, pp. 409-419 (2004).

Dumez et al., Arzneim.-Forsch./Drug Res. (2006), 56(2a):136-151.

Dusheiko et al., "Ribavirin Treatment for Patients with Chronic Hepatitis C: Results of a Placebo-Controlled Study," J. Hepatology (1996) 25:591-598.

Eckart et al., "The Hepatitis C Virus Encodes a Serine Protease Involved in Processing of the Putative Nonstructural Proteins from the Viral Polyprotein Precursor," Biochemical and Biophysical Research Communications, vol. 192, No. 2, pp. 399-406 (1993).

(56) References Cited

OTHER PUBLICATIONS

Edmundson et al., "Cyclic Organophosphorus Compounds. Part 23. Configurational Assignments in the 4-Phenyl-1,3,2-dioxaphosphorinane Series. X-Ray Molecular Structure of cis-2-Benzylamino-4-phenyl-1,3,2- dioxaphosphorinane 2-oxide," J. Chem. Research (S), pp. 122-123 (1989).

Egron et al., "S-Acyl-2-thioethyl Phosphoramidate Diester Derivatives as Mononucleotide Prodrugs" J. Med. Chem., vol. 46, No. 21, pp. 4564-4571 (2003).

Eisenberg et al., "Metabolism of GS-7340, A Novel Phenyl Monophosphoramidate Intracellular Prodrug of PMPA, In Blood," Nucleosides, Nucleotides & Nucleic Acids, vol. 20, No. 4-7, pp. 1091-1098 (2001).

Eldrup et al., "Oral Session V: Hepatitis C Virus, Flaviviruses," Program and Abstracts, The Sixteenth International Conference on Antiviral Research, p. A75, Abstract 119 (Apr. 27 to May 1, 2003).

Eldrup et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).

Engels et al., "Ctclophosphate, III. Synthese und Eignschaften von Uridin-3',5'-cyclophosphat-estern," Chemische Berichte, vol. 110, No. 6, pp. 2019-2027 (1977).

F. Ruebasam etal., Bio. Org. Med. Chem. Lett. (2008) 18: 3616-3621.

Failla et al., "Both NS3 and NS4A are Required for Proteolytic Processing of Hepatitis C Virus Nonstructural Proteins," J. Virol., vol. 68, No. 6, pp. 3753-3760 (1994).

Farquhar et al., "Synthesis and Biological Evaluation of Neutral Derivatives of 5-Fluoro-2'-deoxyuridine 5'-Phosphate," J. Med. Chem., vol. 26, No. 8, pp. 1153-1158 (1983).

Farquhar et al., "Synthesis of Biological Evaluation of 9-]5'-(2-0xo-1,3,2-oxazaphosphorinan-2-yl)-beta-D-arabinosyl] adenine and 9-]5'-(2-0xo-1,3,2-dioxaphosphorinan-2-yl)-beta-D-arabinosyl]adenine: Potential Neutral Precursors of 9- [beta-D-Arabinofuranosyl]adenine 5'-Monophosphate," J. Med. Chem., vol. 28, No. 9, pp. 1358-1361 (1985).

Fields Virology, Editors: Fields, B. N., Knipe, D. M., and Howley, P. M., Lippincott-Raven Publishers, Philadelphia, PA, Chapter 30, pp. 931-959 (1996).

Flamm. "Chronic Hepatitis C Virus Infection," J. Am. Med. Assoc., vol. 289, No. 18, pp. 2413-2417 (2003).

Freed et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (1989).

Fried, M.W. et al., "Peginterferon alfa-2a plus ribavirin for chronic hepatitis C virus infection," New England Journal of Medicine, vol. 347, No. 13, pp. 975-982 (2002).

Furman, PA, et al., "b-D-2'-Deoxy-2'-ftuoro-2'-C-methyluridine Phosphoramidates are Potent and Selective Inhibitors of HGV RNA Replication," Presented at the 15th International Symposium on Hepatitis C Virus & Related Viruses, San Antonio, TX, Oct. 5-9, 2008.

Furman, Phillip A., et al., "PSI-7851: A Novel Liver-Targeting Nucleotide Prodrug for the Treatment of Hepatitis C," Hepatology (2008) 48(4 Suppl):1161A (Abstract #1901).

Furman, Phillip A., et al., "PSI-7851: A Novel Liver-Targeting Nucleotide Prodrug for the Treatment of Hepatitis C," Presented at the 59th Annual Meeting of the American Association for the Study of Liver Diseases, San Francisco, CA, Oct. 31-Nov. 4, 2008.

Gane, E. et al., "Once Daily GS-7977 Plus Ribavirin in HGV Genotypes 1-3: The Electron Trial," EASL 47th Annual Meeting, Barcelona, Spain (Apr. 18-22, 2012).

Gane, E., et al., "Once Daily GS-7977 Plus Ribavirin in HGV Genotypes 1-3: The Electron Trial," Presented at the 47th Annual Meeting of the European Association for the Study of the Liver (Apr. 18-22, 2012), Barcelona, Spain (Poster #1113).

Gane, E., "Future Treatment for Chronic Hepatitis C: IFN or Ribavirin-Free Regimens," Hepatol. Int (2012) 6:16-17 (Abstract #TCS10-03).

Gane, Edward J., et al., "Once Daily PSI-7977 Plus RBV: Pegylated Interferon-Alfa Not Required for Complete Rapid Viral Response in Treatment-Naive Patients with HGV GT2 or GT3," Hepatology (2011) 54(4 Suppl): 377 A (Abstract #34 ).

Gane. E., "Future Hepatitis C Virus Treatment: Interferon-Sparing Combinations," Liver International (2011) 31 (S1 ): 62-67.

Gane. E.J., et al., "Electron: Once Daily PSI-7977 Plus RBV in HGV GT1/2/3," J. Hepatology (2012) 56:S438-S439 (Abstract #1113).

Gardelli et al., J. Med. Chem. (2009) 52(17): 5394-5407.

Ge et al., Nature (2009) 461 (17): 399-401.

Gillespie, et al., "Stereoselective Inhibition of Cholesterol Esterase by Enantiomeric Phosphonates," Phosphorous, Sulfur and Silicon, vol. 122, pp. 205-208 (1997).

Goekjian et al., "Synthesis of Fluorinated Marcocyclic Bis(indolyl)maleimides as Potential 19F NMR Probes for Protein Kinase C," J. Org. Chem. vol., 64., No. 12, pp. 4238-4246 (1999).

Gorbalenya et al., "A conserved NTP-motif in putative helicases," Nature, vol. 333, p. 22 (1988).

Gorbalenya et al., "N-terminal domains of putative helicases of flavi- and pestiviruses may be serine proteases," Nucleic Acids Research, vol. 17, No. 10, pp. 3889-3897 (1989).

Grakoui et al., "A second hepatitis C virus-encoded proteinase," Proc. Natl. Acad. Sci., vol. 90, pp. 10583-10587 (1993).

Grakoui et al., "Characterization of the Hepatitis C Virus-Encoded Serine Proteinase: Determination of Proteinase-Dependent Polyprotein Clevage Sites," J. Virol., vol. 67, No. 5, pp. 2832-2843 (1993).

Griffith et al., "HGV Anti-viral Agents," Annual Reports in Medicinal Chemistry, vol. 39, pp. 223-237 (2004).

Gromova et al.. "Optical Rotatory Dispersion and Circular Dichroism of Mono- and Oligonucleotide-Amino Acids (Amidates)." Biochim. Biophys. Acta., vol. 240, No. 1, pp. 1-11 (1971).

GS-7977 structure provided by Chembest Research Laboratories Ltd. (biochembest.com/product_detail.asp?m=2&id=1178 &classid1 =65&nclassid=195). (last visit for this website was made on Jun. 27, 2013).

Gudmundsson et al., Nucleosides, Nucleotides & Nucleic Acids (2003) 22(10):1953-1961.

Gudmundsson et al., Nucleosides, Nucleotides and Nucleic Acids (2004) 23(12): 1929-1937.

Gunic et al., "6-Hydrazinopurine 2'-methyl ribonucleosides and their 5'-monophosphate prodrugs as potent hepatitis C virus inhibitors," Bioorg. & Med. Chem. Lett., vol. 17, pp. 2456-2458 (2007).

Haleblian, "Characterization of Habits and Crystalline Modification of Solids and Their Pharmaceutical Applications," J. Pharm. Sci., vol. 64, No. 8, 1269-1288 (1975).

Halstead, S. B., "Pathogenesis of Dengue: Challenges to Molecular Biology," Science, vol. 239, pp. 476-481 (1988).

Halstead, S. B., "Selective Primary Health Care: Strategies for Control of Disease in the Developing World. XI. Dengue," Review of Infectious Diseases, vol. 6, No. 2, pp. 251-263 (1984).

Harris et al., "Synthesis and antiviral evaluation of phosphoramidate derivatives of (E)-5-(2-bromovinyl)-2'-deoxyuridine," Antiviral Chemistry & Chemotherapy, vol. 12, No. 5, pp. 293-300 (2001).

Hayashi et al., Genet. Anal. Techn. App 9: 73-79 (1992).

Hernandez et al.. "Synthesis of Highly Functionalized Chiral Nitriles by Radical Fragmentation of beta-Hydroxy Azides. Convenient Transformation of Aldononitriles into 1,4- and 1,5-Iminoalditols," J. Org. Chem., vol. 69. No. 24, pp. 8437-8444 (2004).

Hertel et al., "Synthesis of 2-Deoxy-2,2-difluoro-D-ribose and 2-Deoxy-2,2-diftuoro-D-ribofuranosyl Nucleosides," J. Org. Chem., vol. 53, No. 11, pp. 2406-2409 (1988).

Hijikata et al., "Two Distinct Proteinase Activities required for the Processing of a Putative Nonstructural Precursor Protein of Hepatitis C Virus," J. Virol., vol. 67, No. 8, pp. 4665-4675 (1993).

Hostetler et al., "Greatly Enhanced Inhibition of Human Immunodeficiency Virus Type 1 Replication in GEM and HT4-6C Cells by 3'-Deoxythymidine Diphosphate Dimyristoylglycerol, a Lipid

(56) References Cited

OTHER PUBLICATIONS

Prodrug of 3'-Deoxythymidine," Antimicrobial Agents and Chemotherapy, vol. 36, No. 9, pp. 2025-2029 (1992).
Hostetler et al., "Synthesis and Antiretroviral Activity of Phospholipid Analogs of Azidothymidine and Other Antiviral Nucleosides," J. Biol. Chem., vol. 265, No. 11, pp. 6112-6117 (1990).
Howes et al., "The Regiospecific One-Pot Phosphorylation of Either the 5'—or 2'-Hydroxyl in 3'-Deoxycytidines Without Protection: Critical Role of the Base," Nucleosides, Nucleotides, and Nucleic Acids, vol. 22, No. 5-8, pp. 687-689 (2003).
Hunston et al., "Synthesis and Biological Properties of Some Cyclic Phosphotriesters Derived from 2'-Deoxy-5-ftuorouridine," J. Med. Chem., vol. 27, No. 4, pp. 440-444 (1984).
International Preliminary Examination Report along with Written Opinion of the International Searching Authority issued in International PCT application No. PCT/US2008/058183 issued Apr. 7, 2010 (17 pages).
International Preliminary Examination Report in International Application No. PCT/US2004/012472 issued Dec. 1, 2005.
International Preliminary Report on Patentability and Written Opinion of the International Searching Authority issued in International Application No. PCT/EP2006/069060 mailed Jan. 30, 2007 (13 pages).
International Preliminary Report on Patentability and Written Opinion of the International Searching Authority issued in International Application No. PCT/US2005/025916 issued Jan. 23, 2007 (4 pages).
International Preliminary Report on Patentability and Written Opinion of the International Searching Authority issued in International Application No. PCT/US2005/032406 issued on Mar. 10, 2009 (4 pages).
International Preliminary Report on Patentability for PCT Application No. PCT/US2012/062115, dated May 6, 2014.
International Preliminary Report on Patentability for PCT/US2011/030725 mailed Oct. 2. 2012 (17 pages).
International Search Report and Written Opinion of the International Searching Authority for International Application No. PCT/US2012/062115 mailed Dec. 18, 2012 (10 pages).
International Search Report and Written Opinion of the International Searching Authority for International Application No. PCT/US2012/066605 mailed Mar. 14, 2013 (10 pages).
International Search Report and Written Opinion of the International Searching Authority issued in International Application No. PCT/US2009/069475 (21 pages).
International Search Report dated Nov. 25, 2010, and Written Opinion of the International Searching Authority dated Nov. 20, 2011, issued in PCT/US2010/035641 (23 pages).
International Search Report for PCT/US2009/046619 mailed Sep. 23, 2010 (4 pages).
International Search Report issued in International Application No. PCT/EP2006/069060 mailed Jan. 30, 2007 (4 pages).
International Search Report issued in International Application No. PCT/US2004/012472 mailed Dec. 30, 2004 (4 pages).
International Search Report issued in International Application No. PCT/US2005/025916 mailed Jun. 15, 2006 (2 pages).
International Search Report issued in International Application No. PCT/US2005/032406 mailed May 8, 2008 (3 pages).
International Search Report issued in International PCT application No. PCT/US2008/058183 mailed Mar. 31, 2010 (7 pages).
Invitation to Pay Additional Fees & Partial International Search Report issued in International Application No. PCT/US2010/035641(10 pages).
Iyer et al., "Synthesis in Vitro Anti-Breast Cancer Activity, and Intracellular Decomposition of Amino Acid Methyl Ester and Alkyl Amide Phosphoramidate Monesters of 3'-Azido-3'-deoxythymidine (AZT)," J. Med. Chem., vol. 43, No. 11, pp. 2266-2274 (2000).
J.K. Guillory, Polymorphism in Pharmaceutical Solids (1999) et al pp. 183-226.

Jacobson, I., et al., "PSI-7977 400 mg OD Safety and Tolerability in the First 450 Patients Treated for 12 Weeks," J. Hepatology (2012) 56:S441 (Abstract #1120).
Jacobson, I., "GS-7977 400 mg OD Safety and Tolerability in the Over 500 Patients Treated for at Least 12 Weeks," Presented at the 47th Annual Meeting of the European Association for the Study of the Liver (Apr. 18-22, 2012), Barcelona, Spain (Poster #1120).
Jin et al., "Expression, Isolation, and characterization of the Hepatitis C Virus ATPase/RNA Helicase," Archives of Biochemistry and Biophysics, vol. 323, No. 1, pp. 47-53 (1995).
Jones et al., "Minireview: Nucleotide Prodrugs," Antiviral Research, vol. 27, No. 1-2pp. 1-17 (1995).
Juodka et al., "Oligonucleotides and Nucleotide-Peptides. XXXIV. Synthesis and Some Properties of Complex Nucleotidyl (Oligonucleotidyl)-(P-N)-Amino Acids (Peptides) and Their Ethyl Esters," J. Carbohydrates Nucleosides Nucleotides, vol. 6, No. 4, pp. 333-357 (1979).
Juodka et al., "Oligonucleotides and Nucleotide-Peptides. XXXV. Some Properties of Nucleotidyl-(5'N)-Amino Acid Esters Differing in Amino Acid and Nucleotide Components," J. Carbohydrates Nucleosides Nucleotides, vol. 8, No. 1, pp. 19-39 (1981).
Juodka et al., "Oligonucleotides and Nucleotide-Peptides. XXXVII. On the Mechanism of Hydrolysis of Uridylyl-(5'-N)-Amino Acids. IntramolecuLar Catalysis by the alpha-Carboxyl Group of Amino Acids," J. Carbohydrates Nucleosides Nucleotides, vol. 8, No. 6, pp. 519-535 (1981).
K. Ishi et al., Heptology, 1999, 29: 1227-1235.
Khamnei et al., "Neighboring Group Catalysis in the Design of Nucleotide Prodrugs," J. Med. Chem., vol. 39, No. 20, pp. 4109-4115 (1996).
Kim et al., "Monitoring the Intracellular Metabolism of Nucleoside Phosphoramidate Pronucleotides by 31 P NMR," Nucleosides, Nucleotides and Nucleic Acid, vol. 23, No. 1 & 2, pp. 483-493 (2004).
Kim et al.. "C-Terminal Domain of the Hepatitis C Virus NS3 Protein Contains an RNA Helicase Activity," Biochemical and Biophysical Research Communications, vol. 215, No. 1, pp. 160-166 (1995).
Koon IN et al., "Evolution and Taxonomy of Positive-Strand RNA Viruses: Implications of Comparatives Analysis of Amino Acid Sequences," Critical Reviews in Biochemistry and Molecular Biology, vol. 28, No. 5, pp. 375-430 (1993).
Kotra et al., "Structure-Activity Relationships of 2'-Deoxy-2',2'-diftuoro-L-erythro-pentofuranosyl Nucleosides," J. Med. Chem., vol. 40, No. 22, pp. 3635-3644 (1997).
Kowdley, K.V., et al., "Atomic: 97% RVR for PSI-7977 + PEG/RBV x12 Week Regimen in HGV GT1: An End to Response-Guided Therapy?," J. Hepatology (2012) 56:S1 (Abstract #1).
Kryuchkov et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987) Translated from Russian.
Kucera et al., "Novel Membrane-Interactive Ether Lipid Analogs That Inhibit Infectious HIV-1 Production and Induce Defective Virus Formation," Aids Research and Human Retroviruses, vol. 6, No. 4, pp. 491-501 (1990).
Kwo et al., Lancet 2010.
Lackey et al., "Enzyme-catalyzed therapeutic agent (ECTA) design: activation of the antitumor ECTA compound NB1011 by thymidylate synthase," Biochemical Pharmacology, vol. 61, No. 2, pp. 179-189 (2001).
Lalezari, et al., "Once daily PRI-7977 plus PEGINF/RBV in a phase 2B trial: rapid virologic suppression in treatmen-naïve patients with HCV GT2/GT3," J. Hepatology (2011) 54: S28. (Abstract 61).
Lam, Angela M., et al., "PSI-7851, a Pronucleotide of beta-D-2'-Deoxy-2'-Fluoro-2'-C-Methyluridine Monophosphate, Is a Potent and Pan-Genotype Inhibitor of Hepatitis C Virus Replication," Antimicrob. Agents & Chemother. (2010) 54 (8):3187-3196.
Lawitz, E., et al, "The Effect of Hepatic Impairment on the Safety, Pharmacokinetics, and Antiviral Activity of GS-7977 in Hepatitis C Infected Subjects Treated for Seven Days," Presented at the 47th Annual Meeting of the European Association for the Study of the Liver (Apr. 18-22, 2012), Barcelona, Spain (Poster #1130).

(56) References Cited

OTHER PUBLICATIONS

Lawitz, E., et al., "Once Daily Dual-Nucleotide Combination of PSI-938 and PSI-7977 Provides 94% HCV RNA <LOO at Day 14: First Purine/Pyrimidine Clinical Combination Data (The Nuclear Study)," Journal of Hepatology, vol. 54, pp. 5543 (Late Breaking Abstracts #1370) (2011).
Lawitz, E., et al., "PSI-7977 Proton and Electron: 100% Concordance of SVR4 with SVR24 in HGV GT1, GT2 & GT3," J. Hepatology (2012) 56:S4 (Abstract #7).
Lawitz, E., "The Effect of Hepatic Impairment on the Pharmacokinetics and Antiviral Activity of PSI-7977 in Hepatitis C Infected Subjects Treated for Seven Days," J. Hepatology (2012) 56:S445-S446 (Abstract #1130).
Lawitz, Eric, et al., "Once-Daily PSI-7977 Plus PEG/RBV in Treatment-Naive Patients with HGV GT1: Robust End of Treatment Response Rates Are Sustained Post-Treatment," J. Hepatology (2011) 54(4 Suppl):472A-473A (Abstract #225).
Lee et al., "Selective Intracellular Activation of a Novel Prodrug of the Human Immunodeficiency Virus reverse Transcriptase Inhibitor Tenofovir Leads to Preferential Distribution and Accumulation in Lymphatic Tissue," Antimicrobial Agents and Chemotherapy, vol. 49, No. 5, pp. 1898-1906 (2005).
Lehsten et al., "An Improved Procedure for the Synthesis of Nucleoside Phosphoramidates," Organic Process Research and Development, vol. 6, pp. 819-822 (2002).
Lewis, H., et al., "Second Generation Direct Antiviral and the Way to Interferon-Free Regimens in Chronic HGV," Best Practices & Research: Clinical Gastroenterology (2012) 26:471-485.
Li et al., "Synthesis of the Phosphoramidite Derivative of 2'-Deoxy-2'-C-beta-methylcytidine", J. Org. Chem., vol. 68, No. 17, pp. 6799-6802 (2003).
Lindh et al., J. Infect. Dis. (2011) 203: 1748-1752.
Lohmann et al., "Biochemical Properties of Hepatitis C Virus NS5B RNA-Dependent RNA Polymerase and Identification of Amino Acid Sequence Motifs Essential for Enzymatic Activity," J. Virol., vol. 71, No. 11, pp. 8416-8428 (1997).
Lopez Aparicio et al., "Synthesis of Saccharinic Acid Derivatives," Carbohydrate Research, vol. 129, pp. 99-109 (1984).
Ma et al., "Characterization of the Metabolic Activation of Hepatitis C Virus Nucleoside Inhibitor B-D-2'-Deoxy-2-Fluoro-2'-C-Methylcytidine (PSI-6130) and Identification of a Novel Active 5'-Triphosphate Species," J. Biol. Chem., vol. 282, No. 41, pp. 29812-29820(Oct. 12, 2007).
Mangia et al., Gastroenterology (2010) 139: 821-827.
Martel-Laferriere, V., et al., "GS-7977: a promising nucleotide analog NS5B polymerase inhibitor of HGV," Future Virol. (2012) 7(6):537-546.
McCarthy et al., Gastroenterology (2010) 138: 2307-2314.
McGuigan et al., "Application of Phosphoramidate Pro Tide Technology Significantly Improves Antiviral Potency of Carbocyclic Adenosine Derivatives," J. Med. Chem., vol. 49, No. 24, pp. 7215-7226 (2006).
McGuigan et al., "Application of Phosphoramidate Pronucleotides Technology to Abacavir Leads to a Significant Enhancement of Antiviral Potency," J. Med. Chem., vol. 48, No. 10, pp. 3504-3515 (2005).
McGuigan et al., "Aryl phosphate derivatives of AZT retain activity against HIV1 in cell lines which are resistant to the action of AZT," Antiviral Research, vol. 17, pp. 311-321 (1992).
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., vol. 39, No. 8, pp. 1748-1753 (1996).
McGuigan et al., "Certain Phosphoramidate Derivatives of Dideoxy Uridine (ddU) Are Active Against HIV and Successfully By-pass Thymidine Kinase," FEBS Letters, vol. 351, pp. 11-14 (1994).
McGuigan et al., "Synthesis and anti-HIV activity of some novel chain-extended phosphoramidate derivatives of d4T (stavudine): esterase hydrolysis as a rapid predictive test for antiviral potency," Antiviral Chemistry and Chemotherapy, vol. 9, pp. 109-115 (1998).

McGuigan et al., "Synthesis and evaluation of some novel phosphoramidate derivatives of 3'-azido-3'-deoxythymidine (AZT) as anti-HIV compounds," Antiviral Chemistry and Chemotherapy, vol. 1, No. 2, pp. 107-113 (1990).
McGuigan et al., "Synthesis, anti-human immunodeficiency virus activity and esterase !ability of some novel carboxylic ester-modified phosphoramidate derivatives of stavudine (d4T)," Antiviral Chemistry & Chemotherapy, vol. 9, pp. 473-479 (1998).
McGuigan et al., Bioorg. & Med. Chem. Lett (2010) 20: 4850-4854.
McGuigan et al., Bioorg. & Med. Chem. Lett. (2009) 19: 4250-4254.
McGuigan et al., Bioorg. & Med. Chem. Lett. (2009) 19:4316-4320.
McHutchison, J.G., et al., "Telaprevir with Peg interferon and Ribavirin for Chronic HGV Genotype 1 Infection," N. Engl. J. Med. (2009), vol. 360, No. 18, pp. 1827-1838.
McIntee et al., "Amino Acid Phosphoramidate Nucleosides: Potential ADEPT/GDEPT Substrates," Bioorganic & Medicinal Chemistry Letters, vol. 11, No. 21, pp. 2803-2805 (2001).
McIntee et al., "Probing the Mechanism of Action and Decomposition of Amino Acid Phosphomonoester Amidates of Antiviral Nucleoside Prodrugs," J. Med. Chem., vol. 40, No. 21, pp. 3323-3331 (1997).
Mehellou, Youcef, et al., "Aryloxy Phosphoramidate Triesters: a Technology for Delivering Monophosphorylated Nucleosides and Sugars into Cells," ChemMedChem 4:1779-1791 (2009).
Meier et al., "Cyclic Saligenyl Phosphotriesters of 2',3'-Dideoxy-2',3'-didehydrothymidine (d4T)—A New Pro-Nucleotide Approach," Bioorg. & Med. Chem. Letl., vol. 7, No. 2, pp. 99-104, (1997).
Meyers et al., "Molecular Characterization of Pestiviruses," Advance in Virus Research, vol. 47, pp. 53-119 (1996).
Mills, World Health Organization, "Pharmaceutical excipients—an overview including considersation for paediatric dosing," (Jun. 2010).
Missiha, S.B., et al., "Disease Progression in Chronic Hepatitis C: Modifiable and Nonmodifiable Factors," Gastroenterology (2008), vol. 134, pp. 1699-1714.
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc. Perkin. Trans. 1, pp. 2345-2353 ( 1992).
Moennig et al., "The Pestiviruses," Advances in Virus Research, vol. 41, pp. 53-99 (1992).
Moghaddam et al., Hepatology (2011) 53(3): 746-754.
Monath, T. P., M.D., "Japanese Encephalitis—A Plague of the Orient," N. Engl. J. Med., vol. 319, No. 10, pp. 641-643 (Sep. 8, 1988).
Murakami et al., "Mechanism of Activation of beta-D-2'-Deoxy-2'-Fluoro-2'-C-Methylcytidine and Inhibition of hepatitis C Virus NS5B RNA Polymerase," Antimicrobial Agents and Chemotherapy, vol. 51, No. 2, pp. 503-509 (Feb. 2007).
Murakami et al., "The Mechanism of Action of beta-D-2'-Deoxy-2'-Fluoro-2'-C-Methylcytidine Involves a Second Metabolic Pathway Leading to beta-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy, vol. 52, No. 2, pp. 458-464 (2008).
Murakami, E., et al., "The Mechanism of Action of beta-D-2'-Deoxy-2'-fluoro-2'-C-methylcytidine Involves a Second Metabolic Pathway Leading to beta-D-2'-Deoxy-2'-fluoro-2'-C-methyluridine 5'-Triphosphate, a Potent Inhibitor of the HCV RNA-Dependent RNA Polymerase," 14th International Symposium on Hepatitis C Virus and Related Viruses, Glasgow, Scotland (Sep. 2007).
Murakami, Eisuke, et al., "Mechanism of Activation of PSI-7851 and Its Diastereoisomer PSI-7977," J. Biol. Chem. (2010) 285(45):34337-34347.
Myers, R. M., et al., "Detection of Single Base Substitutions by Ribonuclease Cleavage at Mismatches in RNA:DNA Duplexes," Science (1985), vol. 230, pp. 1242-1246.
Myers, R. M., et al., "Detection of single base substitutions in total genomic DNA," Nature (1985) vol. 313, pp. 495-498.

(56) References Cited

OTHER PUBLICATIONS

Nakayama et al., J. Am. Chem. Soc. (1990) 112(19): 6936-6942.
Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Nelson et al., "The Question of Chair-twist Equilibria for the Phosphate Rings of Nucleoside Cyclic 3',5'-Monophosphates. 1 H NMR and X-ray Crystallographic Study of Diastereomers of Thymidine Phenyl Cyclic 3',5'-Monophosphate," J. Am. Chem. Soc., vol. 109, No. 13, pp. 4058-4064 (1987).
Nelson et al., J. Hepatology (2011 ), vol. 54, pp. S544 (Abstract #1372).
Ni et al., "Progress and development of small molecule HGV antivirals," Current Opinion in Drug Discovery & Development, vol. 7, No. 4, pp. 446-459 (2004).
Nifantyev et al., "Synthesis and Structure of Some Stable Phospholane-Phospholanes," Phosphorus, Sulfur, and Silicon, vol. 113, pp. 1-13 (1996).
Novak, J. J. K., Chiroptical Properties of 2-Methyl-1,4-Lactones.
Novak, J. J. K., "Nucleic Acid Components and Their Analogues CXLIII. Nucleosides Derived from 2-Deoxy-2(R)-C-Methyl-erythro-D-Pentose," Collection Czechoslov. Chem. Commun., vol. 36, pp. 3670-3677 (1971).
Office Action issued in Canadian Patent Application No. 2,763, 151 dated Sep. 25, 2013 (4 pages).
Office Action issued in Canadian Patent Application No. 2,794,669 dated Sep. 30, 2013 (4 pages).
Oishi et al., "Asymmetric Dihydroxylation of Chiral Olefins. High Control of Diastereofacial Selection," Tel. Lett., vol. 34, No. 22, pp. 3573-3576 (1993).
Olsen et al., "2'-Modified Nucleoside Analogs as Inhibitors of Hepatitis C RNA Replication," Program and Abstracts, 16th International Conference on Antiviral Research, Abstract No. 121, p. A76 (Apr. 27-May 1, 2003).
Orita, M., et al., "Detection of polymorphisms of DNA by gel electrophoresis as single-strand conformation polymorphisms," Proc. Natl. Acad. Sci. USA (1989), vol. 86, pp. 2766-2770.
Otto, M., "Evaluation of Nucleoside Analogs in the Hepatitis C Virus Replicon System," Framing the Knowledge of Therapeutics for Viral Hepatitis, IHL Press, First Edition, pp. 247-261 (2006).
Partial International Search Report issued in International Application No. PCT/US2009/069475 (7 pages).
Paul J. Pockros et al., Hepatology (2008) 48(2): 385-397.
Pawlotsky et al., "Antiviral Action of Ribavirin in Chronic Hepatitis C," Gastroenterology (2004) 126:703-714.
PCT/US2005/025916—Written Opinion mailed Jun. 15, 2006.
PCT/US2005/032406—Written Opinion mailed May 8, 2008.
PCT/US2010/035641—International Preliminary Report issued Nov. 22, 2011.
PCT/US2011/030725—International Search Report and Written Opinion mailed Nov. 7, 2011.
PCT/US2011/030725—Partial International Search Report mail Aug. 22, 2011.
Perrone et al. "Application of the Phosphoramidate Pro Tide Approach to 4'-Azidouridine Confers Sub-micromolar Potency versus Hepatitis C Virus on an Inactive Nucleoside," J. Med. Chem., vol. 50, No. 8, 1840-1849 (2007).
Perrone et al.. "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," J. Med. Chem., vol. 50, No. 22, pp. 5463-5470 (2007).
Piantadosi et al., "Synthesis and Evaluation of Novel Ether Lipid Nucleoside Conjugates for Anti-HIV-1 Activity," J. Med. Chem., vol. 34, No. 4, pp. 1408-1414 (1991).
Pierra et al., "Synthesis and Pharmacokinetics of Valopicitabine (NM283), an Efficient Prodrug of the Potent Anti-HGV Agent 2'-C-Methylcytidine," J. Med. Chem., vol. 49, No. 22, pp. 6614-6620 (2006).
Pockros, et al., "R1626 Plus Peginterferon Alfa-2a Provides Potent Suppression of Hepatitis C Virus RNA and Significant Antiviral Synergy in Combination with Ribavirin," Hepatology (2008) 48(2):385-397.
Pogam et al., "No Evidence of R7128 Drug Resistance After Up to 4 Weeks Treatment of GT1, 2 and 3 Hepatitis C Virus Infected Individuals", 44th Annual Meeting of European Association for the Study of the Liver (EASL), Copenhagen, Denmark (Apr. 22-26, 2009).
Poordad, F. et al., "A 12-Week Interferon-Free Regimen of ABT-450/r + ABT-333 + Ribavirin Achieved SVR12 in More Than 90% of Treatment-Naive HGV Genotype-1-Infected Subjects and 47% of Previous Non-Responders," EASL 47th Annual Meeting, Barcelona, Spain (Apr. 18-22, 2012).
Poordad, F., et al., "Rapid Virologic Response: A New Milestone in the Management of Chronic Hepatitis C," Clin. Infectious Diseases (2008), vol. 46, pp. 78-84.
Press Release, Gilead Sciences, Inc., "Gilead Announces Early Sustained Virologic Response Rates for GS-7977 Plus Ribavirin in Genotype 1 Treatment-Naive Hepatitis C Patients" (Apr. 19, 2012).
Press Release, Gilead Sciences, Inc., "Gilead Announces Sustained Virologic Response for 12-Week Regimen of GS-7977 Plus Pegylated Interferon and Ribavin in Genotype 1 Hepatitis C Patients" (Apr. 19, 2012).
Rauch et al., Gastroenterology (2010) 138: 1338-1345.
Ray et al., "Intracellular Metabolism of the Nucleotide Prodrugs GS-9131, a Potent Anti-Human Immunodeficiency Virus Agent," Antimicrobial Agents and Chemotherapy, vol. 52, No. 2, pp. 648-654 (2008).
Reichard et al., "Therapy of Hepatitis C: Alpha Interferon and Ribavirin," Hepatology (1997) 26{3, Suppl. 1):108S-111S.
Remy et al., "Studies on Flourinated Pyrimidines. XIV. The Synthesis of Derivatives of 5-Fluoro-2'-deoxyuridine 5'-Phosphate and Related Compounds," J. Org. Chem., vol. 27, No. 7, pp. 2491-2500 (1962).
Response filed Oct. 25, 2010 at the EPO for European patent application No. EP08732818.3.
Response to non-final Office Action dated Oct. 1, 2009 for U.S. Appl. No. 12/142,554.
Rice, C. M., "Flaviviridae: The Viruses and Their Replication," Fields Virology, 3rd Edition, vol. 1, pp. 931-959 (1996).
Rodriguez-Torres et al., Hepatology (2009) 50(6): 11A (Abstract LB17).
Roman et al., J. Med. Chem. (2010) 53(21): 7675-7681.
Saboulard et al., "Characterization of the Activation Pathway of Phosphoramidate Triester Prodrugs of Stavudine and Zidovudine," Mol. Pharmacol., vol. 56, pp. 693-704 (1999).
Saleeba, JA, et al., "Chemical Cleavage of Mismatch to Detect Mutations," Mutagenesis and Gene Disruption (1993), vol. 217, 286-295.
Sarrazin et al., J. Hepatology (2011) 54: 415-421.
Schultz, C., "Prodrugs of Biologically Active Phosphate Esters" Bioorg. and Med. Chem., vol. 11, pp. 885-898 (2003).
Selected Prosecution Documents for U.S. Appl. No. 11/854,218: (1) Sep. 12, 2007 Amendment.
Selected Prosecution Documents for U.S. Appl. No. 12/878,262: (1) Sep. 9, 2010 Amendment.
Selected Prosecution Documents from U.S. Appl. No. 10/828,753: (1) Feb. 26, 2007 Amendment.
Selected Prosecution Documents from U.S. Appl. No. 12/053,015: (1) Jun. 15, 2010 Restriction Requirement.
Shih et al., "Preparation and Structures of 2-Dimethylamino-4-phenyl-1,3,2-dioxaphosphorinane-2-oxides," Bull. Inst. Chem., Acad. Sin., vol. 41, pp. 9-16, (Mar. 1994).
Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers," J. Pharmacol. and Exp. Ther., vol. 307, No. 3, pp. 1112-1119 (2003).
Siccardi et al., "Stereospecific chemical and enzymatic stability of phosphoramidate triester prodrugs of d4T in vitro," European Journal of Pharmaceutical Sciences, vol. 22, pp. 25-31 (2004).

(56) References Cited

OTHER PUBLICATIONS

Siddiqui et al., "Design and Synthesis of Lipophilic Phosphoramidate d4T-MP Prodrugs Expressing High Potency Against HIV in Cell Culture: Structural Determinants for in Vitro Activity and QSAR," J. Med. Chem., vol. 42, No. 20, pp. 4122-4128 (1999).
Siddiqui et al., "Enhancing the Aqueous Solubility of d4T-based Phosphoramidate Prodrugs," Bioorg. and Med. Chem. Lett., vol. 10, pp. 381-384 (2000).
Siddiqui et al., J. Med. Chem. (1999) 42(3): 393-399.
Smirrnov et al., "A Fluorescent Study of Tryptophan Derivatives of Oligonucleotides and Their Helical Complexes with Polyuridylic," FEBS Letters, vol. 51. No. 1, pp. 211-214 (1975).
Sofia et al., "beta-D-2'-Deoxy-2'-C-methyluridine Phosphoramidates: Potent and Selective Inhibitors of HGV RNA Replication", Poster #P-259, 14th International Symposium on Hepatitis C Virus and Related Viruses, Glasgow, Scotland, UK (Sep. 9 to 13, 2007).
Sofia et al., "beta-D-2'-Deoxy-2'-ftuoro-2'-C-methyluridine Phosphoramidates: Potent and Selective Inhibitors of HGV RNA Replication", 2nd International Workshop on HGV, Poster #7 (Oct. 31, 2007).
Sofia et al., J. Med. Chem. (2010) 53(19): 7202-7218.
Sofia, "Nucleotide prodrugs for HCV therapy," Antivir. Chem. & Chemother., vol. 22, pp. 23-49 (2011).
Sofia, M.J., "beta-D-2'-Deoxy-2'-ftuoro-2'-C-methyluridine Phosphoramidates: Potent and Selective Inhibitors of HGV RNA Replication", 2nd International Workshop on HCV—Resistance and New Compounds (Oct. 31, 2007).
Sofia, M.J., "R7128, A Potent and Selective Nucleoside Inhibitor of HGV NS5B Polymerase: An Overview of Clinical Efficacy and Progress Toward Second Generation Inhibitors", HGV Drug Discovery 2008, Chicago, IL (Apr. 28, 2008).
Sofia, Michael J., et al., "Beta-D-2'-Deoxy-2'-fluoro-2'-C-methyluridine (PSI-6206) phosphoramidates: Potent liver targeting nucleoside inhibitors of HGV RNA replication," 236th ACS National Meeting, Philadelphia, PA, Aug. 20, 2008 (Abstract MEDI 330).
Sofia, Michael J., et al., "Nucleoside, Nucleotide, and Non-Nucleoside Inhibitors of Hepatitis C Virus NS5B RNA-Dependent RNA-Polymerase," J. Med. Chem. (2012) 55:2481-2531.
Song et al., "Pharmacokinetics of Amino Acid Phosphoramidate Monoesters of Zidovudine in Rats," Antimicrobial Agents and Chemotherapy, vol. 46, No. 5, pp. 1357-1363 (2002).
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stella, V. J., "Prodrugs as Therapeutics," Expert opinion on therapeutic patents, vol. 14, No. 3, pp. 277-280 (Mar. 2004).
Stephens, J.C., et al., "Haplotype Variation and Linkage Disequilibrium in 313 Human Genes," Science (2001), vol. 293, pp. 489-493.
Stuyver et al., "Dynamics of Subgenomic Hepatitis C Virus Replicon RNA Levels in Huh-7 Cells after Exposure to Nucleoside Antimetabolites," J. Virol., vol. 77, No. 19, pp. 10689-10694 (2003).
Stuyver et al., "Inhibition of hepatitis C replicon RNA synthesis by B-D-2'-deoxy-2'-fluoro-2'C-methlcytidine: a specific inhibitor of hepatitis C virus replication," Antiviral Chemistry & Chemotherapy, vol. 17, No. 2, pp. 79-87 (2006).
Stuyver et al., "Inhibition of the Subgenomic Hepatitis C Virus Replicon in Huh-7 Cells by 2'-Deoxy-2'-Fluorocytidine," Antimicrobial Agents and Chemotherapy, vol. 48, No. 2, pp. 651-654 (2004).
Stuyver et al., "Ribonucleoside Analogue that Blocks Replication of Bovine Viral Diarrhea and Hepatitis C Viruses in Culture," Antimicrobial Agents and Chemotherapy, vol. 47, No. 1, pp. 244-254 (2003).
Sulkowski, M., et al., "Potent Viral Suppression with All-Oral Combination of Daclatasvir (NS5A Inhibitor) and GS-7977 (NS5B Inhibitor),+/− Ribavirin, in Treatment-Naive Patients with Chronic HGV GT1, 2, or 3," J. Hepatology (2012) 56:S560 (Abstract #1422).
Suppiah et al., Nature Genetics (2009) 41 (10): 1100-1104.
Tan et al., "Hepatitis C Therapeutics: current Status and Emerging Strategies," Nature Reviews, vol. 1, pp. 867-881 (2002).
Tanabe et al., "Synergistic Inhibition of Intracellular Hepatitis C Virus Replication by Combination of Ribavirin and Interferon-alpha," J. Infect. Dis. (2004) 189(7):1129-1139.
Tanaka et al., Nature Genetics (2009) 41 (10): 1105-1109.
The Extended search report includes the supplementary European search report issued in European Application No. 05775359.2 dated Sep. 15, 2010 (9 pages) et al.
Tomei et al., "N53 Is a Serine Protease Required for Processing of Hepatitis C Virus Polyprotein," J. Virol., vol. 67, No. 7, pp. 4017-4026 (1993).
U.S Appl. No. 10/828,753, Final Office Action Rejection, mailed Feb. 26, 2008.
U.S Appl. No. 11/353,597, Non-Final Office Action Rejection, mailed Jul. 17, 2008.
U.S Appl. No. 11/353,597, Non-Final Office Action Rejection, mailed Oct. 2, 2007.
U.S Appl. No. 11/635,898, Pending claims filed Dec. 24, 2009.
U.S Appl. No. 12/142,554, Non-Final Office Action Rejection, mailed Oct. 1, 2009.
U.S. Appl. No. 11/225,425 pending claims filed Oct. 2, 2009.
U.S. Appl. No. 12/645,710, filed Dec. 23, 2009—Originally filed claims.
U.S. Appl. No. 12/783,680, filed May 20, 2010—Originally filed claims.
U.S. Appl. No. 13/076,552, filed Mar. 31, 2011—Originally filed claims.
U.S. Appl. No. 10/828,753, Non-Final Office Action Rejection, mailed Mar. 30, 2007.
U.S. Appl. No. 11/225,425, Final Office Action Rejection, mailed Feb. 18, 2010.
U.S. Appl. No. 11/225,425, Non-Final Office Action Rejection, mailed Jul. 7, 2009.
U.S. Appl. No. 11/225,425, Non-Final Office Action Rejection, mailed Nov. 13, 2008.
U.S. Appl. No. 11/353,597, Final Office Action Rejection, mailed Dec. 2, 2008.
U.S. Appl. No. 11/635,898, Non-Final Office Action Rejection, mailed Jul. 28, 2009.
U.S. Appl. No. 11/854,218, Non-Final Office Action Rejection, mailed Oct. 1, 2009.
U.S. Appl. No. 11/854,218, Pending claims filed Sep. 12, 2007.
U.S. Appl. No. 12/142,536, Non-Final Office Action Rejection, mailed Oct. 2, 2009.
U.S. Appl. No. 12/142,536, Pending claims filed Jun. 19, 2008.
U.S. Appl. No. 12/142,554, Pending claims filed Dec. 17, 2009.
U.S. Appl. No. 12/240,342, Non-Final Office Action Rejection, mailed Oct. 1, 2009.
U.S. Appl. No. 12/240,342, Pending claims filed Sep. 29, 2008.
U.S. Appl. No. 12/479,075, filed Jun. 5, 2009.
U.S. Appl. No. 12/553,483, Non-Final Office Action Rejection, mailed Dec. 17, 2009.
U.S. Appl. No. 12/553,483, Pending claims filed Feb. 22, 2010.
U.S. Appl. No. 12/645,710, filed Dec. 23, 2009.
U.S. Appl. No. 12/645,765, filed Dec. 23, 2009.
U.S. Appl. No. 12/645,821, filed Dec. 23, 2009.
U.S. Appl. No. 11/854,218, filed Sep. 12, 2007—Claims as Amended Jun. 28, 2011.
U.S. Appl. No. 12/878,262, filed Sep. 9, 2010—Claims as Amended Sep. 1, 2011.
U.S. Appl. No. 13/099,671, filed May 3, 2011—Claims as Amended Sep. 4, 2012.
U.S. Appl. No. 60/392,350, filed Jun. 28, 2002.
U.S. Appl. No. 60/392,351, filed Jun. 28, 2002.
Uchiyama et al., J. Org. Chem. (1993) 58(2): 373-379.

(56) References Cited

OTHER PUBLICATIONS

Uckun et al., "In Vivo Pharmacokinetics and Toxicity Profile of the Anti-HIV Agent Stampidine in Dogs and Feline Immunodeficiency Virus-infected Cats," Arzneim.-Forsch./Drug Res., vol. 56, No. 2a, pp. 176-192 (2006).
Venkatachalam et al., "Rational Drug Design of Multifunctional Phosphoramidate Substituted Nucleoside Analogs," Current Pharmaceutical Design, vol. 10, No. 15, pp. 1713-1726 (2004).
Venkatachalam et al.. "Synthesis and metabolism of naphthyl substituted phosphoramidate derivatives of stavudine." Bioorg. and Med. Chem., vol. 14, pp. 5161-5177 (2006).
Von Wagner et al., Gastroenterology (2005) 129: 522-527.
Wagner et al., "Antiviral Nucleoside Drug Delivery via Amino Acid Phosphoramidates," Nucleosides, Nucleotides and Nucleic Acids, vol. 18, No. 4 & 5, pp. 913-919 (1999).
Walker et al., "Promising candidates for the treatment of chronic hepatitis C," Expert Opin. Investig. Drugs, vol. 12, No. 8, pp. 1269-1280 (2003).
Warrener et al., "Pestivirus NS3 (p80) Protein Possesses RNA Helicase Activity," J. Viral., vol. 69, No. 3, pp. 1720-1726 (1995).
Wiskerchen et al.. Pestivirus Gene Expression: Protein p80 of Bovine Viral Diarrhea Virus Is a Proteinase Involved in Polyprotein Processing. Virology, vol. 184, pp. 341-350 (1991).
Wittine, K., et al., "The Novel Phosphoramidate Derivatives of NSAID3-Hydroxypropylamides: Synthesis, Cytostatic and Antiviral Activity Evaluations," Eur. J. Med. Chem. (2009) 44:143-151.
Wolff, M.E., "Burger's Medicinal Chemistry and Drug Discovery," Fifth Edition, vol. 1, pp. 975-977 (1995).
Wozniak et al., Chem. Soc. Rev. (2003) 32:158-169.
Written Opinion of the International Searching Authority issued in International Application No. PCT/US2004/012472 dated Dec. 29, 2004 (7 pages).
Wu et al., "Synthesis and Biological Activity of a Gemcitabine Phosphoramidate Prodrug," J. Med. Chem., vol. 50, No. 15, pp. 37 43-37 46 (2007).
Wu et al., "Targeting NS5B RNA-Dependent RNA Polymerase for Anti-HGV Chemotherapy," Current Drug Targets—Infectious Disorders, vol. 3, No. 3, pp. 207-219 (2003).
Xiao-Ling et al., "The Synthesis of (2S,3R)-Sphingosine from D-Mannitol", Acta Chimica Sinica, vol. 54, pp. 826-832 (1996).
Xiao-Ling et al.. "Study on the Chirality of Sulfur in Ethyl (2S,3R,4R)-4,5-0-Isopropylidene-2,3-sulfinyl-2,3,4,5-tetrahydroxy-pentanoate", Acta Chimica Sinica, vol. 55, pp. 600-604 (1997).
Xu et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., vol. 71, No. 7, pp. 5312-5322 (1997).
Yuan et al., "Expression, Purification, and Partial Characterization of HGV RNA Polymerase," Biochemical and Biophysical Research Communications, vol. 232, No. 1, pp. 231-235 (1997).
Yuodka et al., "Oligonucleotides and polynucleotides. XXVI. Synthesis of esters of nucleotidyl- and oligonucleotidyl-(5'-N)-(Amino Acid)s and -peptides," translated from Biooorganicheskaya Khimiya, vol. 2, No. 11, pp. 1089-1094 (1976).
Zeuzem, S., et al., "Review article: management of patients with chronic hepatitis C virus infection and 'normal' alanine aminotransferase activity," Aliment Pharmacol. & Ther. (2006), vol. 24, pp. 1133-1149.
Zhong et al., "Identification and characterization of an RNA-Dependent RNA Polymerase Activity within the Nonstructural Protein 5B Region of Bovine Viral Diarrhea Virus," J. Virol., vol. 72, No. 11, pp. 9365-9369 (1998).
Zhou, Xiao-Jian, et al., "Safety and Pharmacokinetics of IDX184, a Liver-Targeted Nucleotide Polymerase Inhibitor of Hepatitis C Virus, in Healthy Subjects," Antimicrob. Agents & Chemother. (2011) 55(1):76-81.
Zhu et al., "Design and synthesis of HCV agents with sequential triple inhibitory potentials," Bioorg. & Med. Chem. Lett. (2010) 20(17): 5212-5216.
Zhu, Y., et al, "Virologic Analysis of HGV Genotype 1 Patient Samples from the Proton Study," Presented at the 47th Annual Meeting of the European Association for the Study of the Liver (Apr. 18-22, 2012), Barcelona, Spain (Poster #1217).
Zon, G., "4 Cyclophosphoamide Analogues," Progress in Medicinal Chemistry, vol. 19, pp. 205-246 (1982).
Communication pursuant to Rules 161(1) and 162 EPC for European Application No. 12795307.3 dated Jul. 29, 2014.
Office Action issued in Morrocan Patent Application No. 37130 dated Feb. 9, 2015 (5 pages).
Search Report in Panama Application No. 90225-01 dated Apr. 22, 2015, (7 pages).
Opposition by Asociación Industrial de Laboratorios Farmacéuticos AG in Chilean Application No. 1397-2014 dated Apr. 30, 2015, (5 pages).
Office Action in Canadian Application No. 2856529 dated May 5, 2015, (5page).
Office Action in Israeli Application No. 232889 dated May 18, 2015 (8 pages).
Office Action in Japanese Application No. 2014-543607 dated May 21, 2015 (8 pages).
Search Report of Taiwanese Application No. 101144495 dated Jun. 3, 2015 (12 pages).
Substantive Examination Report in Philippines Application No. 1-2014-501133 dated Jun. 30, 2015 (2 pages).
Office Action in Colombian Application No. 14.121.393 dated May 25, 2015 ( 29 pages).
Notice of Grounds for Rejection in Korean Application No. 2014-7016699 dated Jun. 5, 2015 (12 pages).
Office Action in Eurasian Application No. 201490903/28 dated Jul. 14, 2015 (9 pages).
Office Action for AP Appl. No. AP/P/2014/007699 dated Nov. 27, 2015, 6 pages.
Office Action for CL Appl. No. 2014-001397 dated Jan. 20, 2016, with English translation, 36 pages.
Office Action for CN Appl. No. 201280058114.0 dated Jul. 21, 2016, with English translation, 7 pages.
Office Action for CN Appl. No. 201280058114.0 dated Mar. 1, 2016, with English translation, 14 pages.
Office Action for EA Appl. No. 201490903 dated Apr. 26, 2016, with English translation, 4 pages.
Office Action for IL Appl. No. 232889 dated Jan. 17, 2016, with English translation, 6 pages.
Office Action for PA Appl. No. 90225-01 dated Apr. 22, 2015, 3 pages.
Office Action for TH Appl. No. 1401002830 dated Jul. 5, 2016, with English translation, 2 pages.
Office Action for CL Appl. No. 2014-001397 dated Aug. 5, 2016, with English translation, 22 pages.
First Office Action for GG Appl. No. GC 2012-22917 dated May 18, 2015, 6 pages.
Second Office Action for GC Appl. No. GC 2012-22917 dated Mar. 2, 2016, 7 pages.
Office Action for PK Appl. No. 803/2012 dated Mar. 11, 2015, 4 pages.
Office Action for TW Appl. No. 101144495 dated Jun. 23, 2015, with English translation, 14 pages.
Examination Report in New Zealand Application No. 625532 dated Mar. 17, 2015, 3 pages.
Examination Report in Australia Application No. 2012346217 dated Mar. 16, 2015, 4 pages.
Office Action in European Application No. 12 795 307.3 dated Jul. 4, 2016 (4 pages), received Aug. 16, 2016.

* cited by examiner

COMPOSITIONS AND METHODS FOR TREATING HEPATITIS C VIRUS

This application is a continuation of U.S. application Ser. No. 13/686,664, filed Nov. 27, 2012, now U.S. Pat. No. 8,889,159, which is a continuation-in-part of U.S. application Ser. No. 13/661,509, filed Oct. 26, 2012, a continuation-in-part of International Application No. PCT/US2012/055621, filed Sep. 14, 2012, and which claims the benefit under 35 U.S.C. §119(e) of U.S. Provisional Application No. 61/564,500, filed Nov. 29, 2011 and U.S. Provisional Application No. 61/707,459, filed Sep. 28, 2012, all of which are incorporated by reference in their entireties.

FIELD OF THE INVENTION

Disclosed herein are a composition and unit dosage form for the treatment of hepatitis C virus (HCV) infection comprising GS-7977 and at least one pharmaceutically acceptable excipient, as well as methods for making the said composition and unit dosage form. Also disclosed herein is a method of treating a subject, preferably a human, infected with hepatitis C virus, said method comprising administering to the subject for a time period an effective amount of GS-7977 and an effective amount of ribavirin. In one aspect, the method comprises administering to the subject an interferon-free treatment regimen comprising an effective amount of GS-7977 and an effective amount of ribavirin. In a particular aspect, the method is sufficient to produce an undetectable amount of HCV RNA in the subject for at least 12 weeks after the end of the time period.

BACKGROUND

Hepatitis C virus ("HCV") infection is a major health problem that leads to chronic liver disease, such as cirrhosis and hepatocellular carcinoma, in a substantial number of infected individuals, estimated by the World Health Organization to be about 3% of the world's population. (World Health Organization, Hepatitis C (2002).) According to the U.S. Centers for Disease Control and Prevention, HCV is the most common blood-borne infection in the United States, with an estimated 3.2 million people (1.8%) chronically infected in the United States alone. (U.S. Centers for Disease Control and Prevention, Viral Hepatitis Surveillance— United States, 2010; U.S. Centers for Disease Control and Prevention, Morbidity and Mortality Weekly Report 70(17): 537-539 (May 6, 2011).) An estimated 150-180 million individuals are chronically infected with HCV worldwide, with 3 to 4 million people infected each year. (World Health Organization, Hepatitis C, Fact Sheet No. 164 (July 2012); Ghany et al., Hepatology (2009) 49(4): 1335-1374.) Once infected, about 20% of people clear the virus, but the rest can harbor HCV for the rest of their lives. Ten to twenty percent of chronically infected individuals eventually develop liver-destroying cirrhosis or cancer. (Naggie et al., J. Antimicrob. Chemother. (2010) 65: 2063-2069.) The viral disease is transmitted parenterally by contaminated blood and blood products, contaminated needles, or sexually and vertically from infected mothers or carrier mothers to their offspring.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural ("NS") proteins are believed to provide the catalytic machinery for viral replication. The NS3 protease releases NS5B, the RNA-dependent RNA polymerase, from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex. (K. Ishi, et al, Hepatology (1999) 29: 1227-1235; V. Lohmann, et al., Virology (1998) 249: 108-118.) Inhibition of HCV NS5B polymerase prevents formation of the double-stranded HCV RNA and therefore constitutes an attractive approach to the development of HCV-specific antiviral therapies.

A number of potential molecular targets for drug development of direct acting antivirals as anti-HCV therapeutics have now been identified including, but not limited to, the NS2-NS3 autoprotease, the N3 protease, the N3 helicase, and the NS5B polymerase. The RNA-dependent RNA polymerase is essential for replication of the single-stranded, positive sense, RNA genome, and this enzyme has elicited significant interest among medicinal chemists. Another auxiliary protein of HCV is referred to as NS5A. The NS5A nonstructural protein is a phosphoprotein, with no apparent enzymatic activity; however it acts as a multifunctional regulator of cellular pathways, including host cell growth, immunity and innate immunity, and virus replication. (Appel et al., J. Virol. (2005) 79: 3187-3194; Evans et al., Proc. Natl. Acad. Sci. USA (2004) 101: 13038-13043; Gale et al., Nature (2005) 436: 939-945; Gale et al., Virology (1997) 230: 217-227; Ghosh et al., J. Gen. Virol. (1999) 80(Pt 5): 1179-1183; Neddermann et al., J. Virol. (1999) 73: 9984-9991; Polyak et al., Hepatology (1999) 29: 1262-1271; Shimakami et al., J. Virol. (2004) 78: 2738-2748; Shirota et al., J. Biol. Chem. (2002) 277: 11149-11155; and Tan et al., Proc. Natl. Acad. Sci. U.S.A. (1999) 96: 5533-5538.) NS5A is associated with host cell membranes through its N-terminal amphipathic helix, where it is a part of the replication complex. (Elazar et al., J. Virol. (2004) 78: 11393-11400 and Penin et al., J. Biol. Chem. (2004) 279: 40835-40843.) Recent studies suggest that NS5A is organized into three domains: the first 213 amino acids in the N-terminal domain constitutes domain I and contains a zinc binding motif suggesting that the protein is a zinc metalloprotein and domains II and III are in the C-terminal region of the protein. (Tellinghuisen et al., J. Biol. Chem. (2004) 279: 48576-48587 and Tellinghuisen et al., Nature (2005) 435: 374-379.) NS5A exists in two phosphorylated forms: a basal form of 56 kD and a hyperphosphorylated form of 58 kD. The protein is phosphorylated at specific sites, primarily on serine residue within domains II and III, by host cell kinases. (Ide et al., Gene (1997) 201: 151-158; Kaneko et al., Biochem. Biophys. Res. Commun. (1994) 205: 320-326; Katze et al., Virology (2000) 278: 501-513; Reed et al., J. Biol. Chem. (1999) 274: 28011-28018; Reed et al., J. Virol. (1997) 71: 7187-7197; and Tanji et al., J. Virol. (1995) 69: 3980-3986.)

The initially-approved standard of care ("SOC") for the treatment of chronic HCV infection is a combination therapy with pegylated interferon alfa-2a or pegylated interferon alfa-2b (collectively "peginterferon" or "PEG") used alone or in combination with ribavirin ("RBV"). The primary goal of treatment for chronic hepatitis C is a sustained virologic response ("SVR"), which refers to an undetectable level of serum HCV RNA maintained for a period of time post-treatment. Host factors including age, body weight, race, and advanced fibrosis influence the outcome of treatment (Dienstag and McHutchison Gastroenterology (2006)130: 231-

264 and Missiha et al., Gastroenterology (2008) 134: 1699-1714), but are poor predictors of response. In contrast, viral factors like the genotype and the on-treatment pattern of viral response can be used to determine the likelihood of treatment success and guide treatment duration individually, and they have proven to be very useful in clinical practice. (Ge et al., Nature (2009) 461: 399-401.)

In spite of an encouraging response in some patients to SOC treatment, the overall response to peginterferon/ribavirin combination therapy among patients infected with Hepatitis C virus is only about 50%. SVR rates are <50% for patients infected with genotype 1 HCV treated with a prolonged duration (48-72 weeks) of peginterferon/ribavirin therapy. (Naggie et al., J. Antimicrob. Chemother. (2010) 65: 2063-2069.) Accordingly, there is a need to provide a therapy resulting in improved SVR compared to the outcome of treatment with peginterferon alone or in combination with ribavirin. There is also a need to provide a therapy that reduces the time in which patients show evidence of complete viral suppression (negative HCV status) following the initiation of treatment.

Peginterferon alfa-2a ("PEG-IFN-α-2a" or "peginterferon α-2a"), marketed under the trademark PEGASYS®, is an antiviral administered by subcutaneous injection indicated for, among other things, treatment of chronic hepatitis C ("CHC") when administered alone or in combination with ribavirin. PEGASYS® is indicated for the treatment of CHC in patients with compensated liver disease not previously treated with interferon alpha, in patients with histological evidence of cirrhosis and compensated liver disease, and in adults with CHC/HIV co-infection. Combination therapy using PEG-IFN-α-2a and ribavirin is recommended unless the patient has contraindication to or significant intolerance to ribavirin.

Peginterferon alfa-2b ("PEG-IFN-α-2b" or "peginterferon α-2b"), marketed under the trademark PEGINTRON®, is also administered by subcutaneous injection and is indicated for use alone or in combination with ribavirin to treat CHC in patients with compensated liver disease. Like PEG-IFN-α-2a, PEG-IFN-α-2b has undesirable side effects.

Ribavirin ("RBV"), marketed under the trademark COPEGUS®, is a nucleoside analogue indicated for the treatment of CHC virus infection in combination with peginterferon in patients 5 years of age and older with compensated liver disease not previously treated with peginterferon, and in adult CHC patients co-infected with HIV. Ribavirin alone is not approved for the treatment of CHC. (COPEGUS® FDA-approved label, revised August 2011.) Clinical trials have shown that ribavirin alone can normalize alanine aminotransferase ("ALT") levels transiently during the course of treatment in some patients with CHC infections. However, these studies have reported that ribavirin alone did not reduce HCV RNA levels during or after therapy and did not produce any sustained virologic response. (Di Bisceglie et al., Ann. Intern. Med. (1995) 123(12): 897-903; Dusheiko et al., J. Hepatology (1996) 25: 591-598; Bodenheimer, Jr., et al., Hepatology (1997) 26(2): 473-477.) One clinical study reported observing a decrease in HCV RNA from treatment with ribavirin monotherapy (1.0 to 1.2 g daily for 24 weeks); however, the observed HCV RNA decrease was transient and no patient receiving ribavirin monotherapy cleared HCV RNA. (Pawlotsky et al., Gastroenterology (2004) 126: 703-714.)

Treatment of CHC using peginterferon alone or in combination with ribavirin has several disadvantages. First and foremost, this therapy is not effective for many patients. For instance, certain Phase 3 clinical trials using the combination of peginterferon and ribavirin reported SVR rates of 54 to 63%, but additional studies show that the SVR rates may be much lower in certain populations. (Feurstadt et al., Hepatology (2010) 51(4): 1137-1143.) Second, use of peginterferon and ribavirin is associated with certain adverse events. For instance, the boxed warning on the PEGASYS® label states that use of peginterferon may cause or aggravate fatal or life-threatening neuropsychiatric, autoimmune, ischemic, and infectious disorders. (PEGASYS® (peginterferon alfa-2a) FDA-approved label, revised September 2011.) Additionally, the boxed warning on the COPEGUS® label states that ribavirin adverse effects may include hemolytic anemia and that significant "teratogenic and embryocidal effects have been demonstrated in all animal species exposed to ribavirin." (COPEGUS® (ribavirin) FDA-approved label, revised August 2011.) Finally, the peginterferon/ribavirin treatment protocol is quite expensive. Given these disadvantages, there has been a recognized need to develop new anti-HCV drug substances and treatment regimens.

The FDA recently approved two additional drug products for the treatment of genotype 1 CHC, boceprevir and telaprevir, both of which are HCV NS¾ protease inhibitors. Boceprevir, marketed under the trademark VICTRELIS®, is indicated for the treatment of genotype 1 CHC infection, in combination with interferon and ribavirin, in adult patients (≥18 years of age) with compensated liver disease, including cirrhosis, who are previously untreated or who have failed previous interferon and ribavirin therapy. Telaprevir, marketed under the trademark INCIVEK®, is indicated, in combination with interferon and ribavirin, for the treatment of genotype 1 CHC in adult patients with compensated liver disease, including cirrhosis, who are treatment-naïve or who have been previously treated with interferon-based treatment, including prior null responders, partial responders, and relapsers. Both boceprevir and telaprevir are approved for administration in combination with peginterferon and ribavirin only; neither is approved for monotherapy or for administration with ribavirin alone. (INCIVEK® (telaprevir) FDA-approved label, revised June 2012; VICTRELIS® (boceprevir) FDA-approved label, revised July 2012.)

The introduction of both boceprevir and telaprevir has increased the therapeutic options available to HCV-infected patients; however, both treatment regimens have certain disadvantages. A principle disadvantage is that the boceprevir and telaprevir regimens still require the use of peginterferon. Additional disadvantages are summarized below.

Boceprevir (used in combination with peginterferon α-2a and ribavirin) has a complicated dosing regimen, e.g., 800 mg (4×200 mg) three times daily (every 7 to 9 hours) with food. Moreover, late-stage clinical studies show that boceprevir used in combination with peginterferon and ribavirin results in a 66% SVR rate. (Manns et al., Liver Int'l (2012) 27-31.) Additionally, the boceprevir regimen must be administered for 48 weeks, which means that the treatment costs are quite expensive. Finally, use of boceprevir in combination with peginterferon and ribavirin is presently limited to those subjects infected with HCV genotype 1.

The telaprevir regimen (used in combination with peginterferon and ribavirin) requires a dosing regimen of 750 mg (2×375 mg) three times daily (7-9 hours apart) with food. An SVR rate of 79% was reported for patients receiving telaprevir in combination with peginterferon and ribavirin for 12 weeks. (Jacobson et al., New Engl. J. Med. (2011) 364: 2405-2416.) However, reports reveal that about half of the treated patients developed a skin rash or itching, and a small number of patients developed the severe Stevens-Johnson Syndrome, a life-threatening skin condition, in which case the regimen must be terminated. Finally, use of telaprevir in combination with peginterferon and ribavirin is presently limited to those subjects infected with HCV genotype 1. Although the treatment period is reduced for telaprevir as compared to that for boceprevir, the treatment costs for the two regimens are about the same.

Despite the additional options offered by the boceprevir and telaprevir regimens, these alternative treatments still have disadvantages. Further, genotype 1 patients who fail therapy with boceprevir and/or telaprevir in combination with peginterferon and ribavirin may develop undesirable NS3 protease inhibitor resistance. (E.g., Pawlotsky, Hepatology (2011) 53(5): 1742-1751.) There is a need for improved treatment regimens that are more effective, safe, tolerable, shorter in duration, and which are associated with reduced rates of viral breakthrough and/or viral resistance. In particular, there is a need for interferon-free treatment regimens that are effective for treating CHC but result in reduced side-effects compared to treatment regimens involving interferon or peginterferon. There is also a need for interferon-free treatment regimens for patients suffering from CHC infection who are interferon-ineligible or interferon-intolerant.

GS-7977 (also called sofosbuvir and formerly called PSI-7977) is a nucleotide analog prodrug currently in Phase 2/Phase 3 trials for treatment of chronic HCV infection.

Several Phase 2 clinical trials have been conducted to evaluate the efficacy, safety and tolerability of GS-7977 400 mg administered for 8 or 12 weeks with or without ribavirin and optionally peginterferon in subjects with GT1, GT2 or GT3 HCV. The results of these trials, along with the results if in vitro studies, revealed several potential and hereto unknown advantages of HCV treatment regimens utilizing GS-7977 in combination with ribavirin. These results provide a basis for the disclosed and claimed method and composition for treating HCV infection.

SUMMARY

Disclosed herein are a composition and unit dosage form for the treatment of hepatitis C virus (HCV) infection comprising GS-7977 and at least one pharmaceutically acceptable excipient, as well as methods for making said composition and unit dosage form.

Also disclosed herein is a method of treating a subject, preferably a human, infected with hepatitis C virus, said method comprising administering to the subject for a time period an effective amount of GS-7977 and an effective amount of ribavirin. In one aspect, the method comprises administering to the subject an interferon-free treatment regimen comprising an effective amount of GS-7977 and an effective amount of ribavirin. In a particular aspect, the method is sufficient to produce an undetectable amount of HCV RNA in the subject for at least 12 weeks after the end of the time period.

DETAILED DESCRIPTION

Definitions

Figure 1:
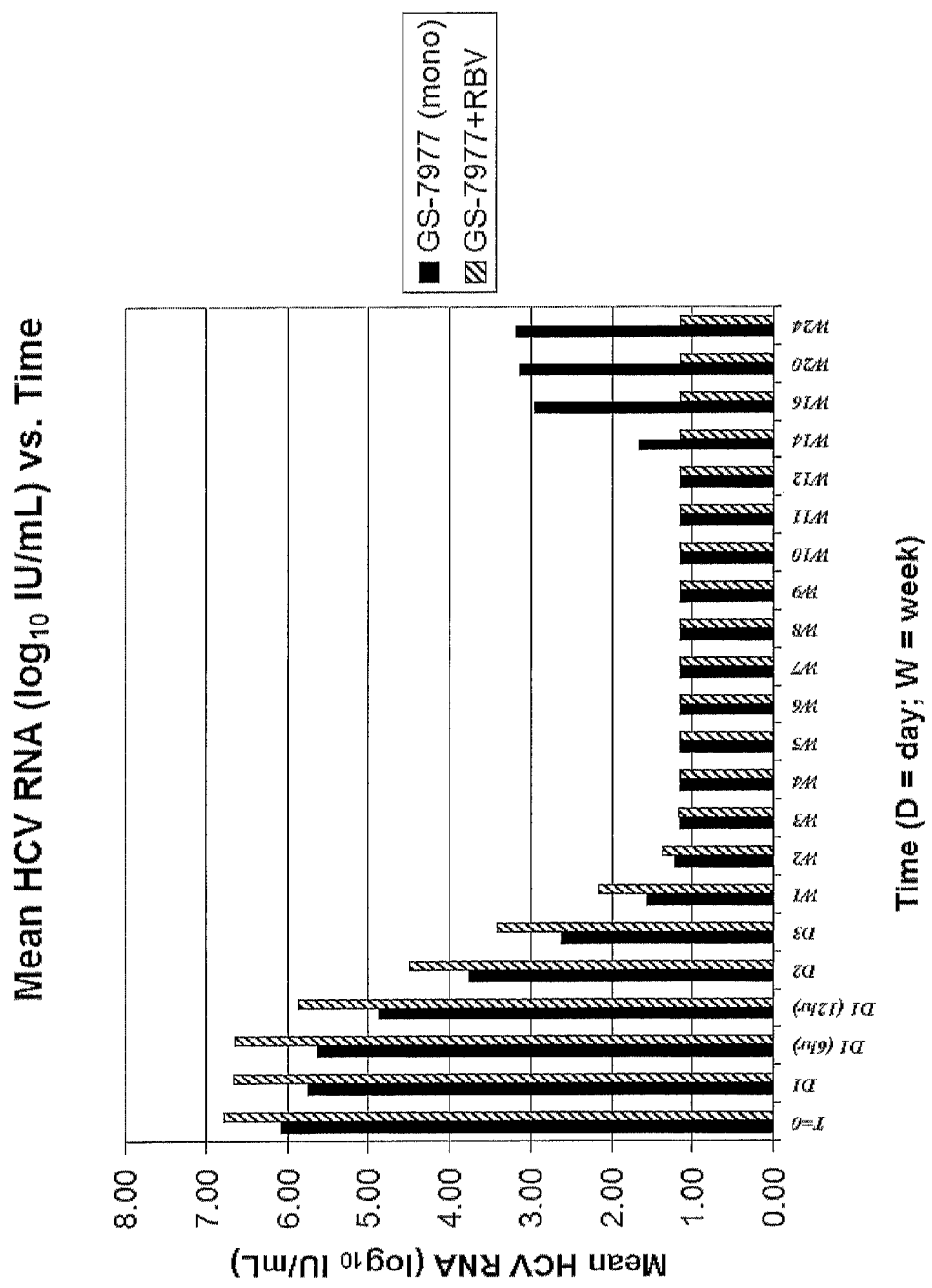
FIG. 1. Plot of Mean HCV RNA ($log_{10}$ IU/mL) versus time during treatment and for up to 12 weeks after the end of treatment ("EOT") for HCV GT2/GT3 treatment-naïve patients receiving a combination of GS-7977 (400 mg QD) and RBV (1000/1200 mg BID based on weight) for 12 weeks (ELECTRON Group 1).

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The term "about" (also represented by "~") has its plain and ordinary meaning of "approximately" except as related to an amount of GS-7977, an amount of ribavirin, or an amount of HCV RNA. As related to an amount of GS-7977, an amount of ribavirin, or an amount of HCV RNA, the qualifier "about" reflects the standard experimental error.

The terms "optional" or "optionally" as used herein means that a subsequently described event or circumstance may but need not occur, and that the description includes instances where the event or circumstance occurs and instances in which it does not.

The term "subject" as used herein means a mammal. Preferably the subject is a human.

The term "effective amount" as used herein means an amount sufficient to reduce symptoms of the HCV infection in a subject.

The term "undetectable amount" refers to an amount of HCV RNA, as determined by the assay methodology described herein, that is less than the limit of detection ("LOD") of about 15 IU/mL.

A sustained virologic response (SVR) for a patient treated according to one of the treatment regimens described herein is defined as a patient who completes the HCV treatment regimen and who has an undetectable amount of HCV RNA (i.e., <about 15 IU/mL) for a period of time post-treatment as measured in accordance with the assay methodology described herein. SVR-N is the abbreviation for sustained virologic response N weeks after completion of one of the HCV treatment regimens disclosed herein. For example, SVR-4 is the abbreviation for sustained virologic response 4 weeks after completion of one of the HCV treatment regimens disclosed herein.

The term "preparation" or "dosage form" is intended to include both solid and liquid formulations of the active compound and one skilled in the art will appreciate that an active ingredient can exist in different preparations depending on the desired dose and pharmacokinetic parameters.

The term "unit dosage form" refers to a physically discrete unit containing a predetermined quantity of the active compound. Preferred unit dosage forms are those containing a daily dose or unit daily sub-dose, or an appropriate fraction thereof, of GS-7977.

The terms "pharmaceutically acceptable excipient" and "pharmaceutical excipient" as used herein refer to a compound that is used to prepare a pharmaceutical composition, and is generally safe, non-toxic and neither biologically nor otherwise undesirable, and includes excipients that are acceptable for veterinary use as well as human pharmaceutical use.

RVR is the abbreviation for rapid virologic response and refers to an undetectable level of HCV RNA in the blood at week 4 of treatment. The occurrence of RVR has been reported to be predictive of ultimate SVR for a full treatment course of 48 weeks with peginterferon/ribavirin combination treatment in HCV GT-1 patients. (Poordad et al., Clin. Infect. Dis. (2008) 46: 78-84.)

QD means that the dose is administered once a day.

BID means that the dose is administered twice a day.

TID means that the dose is administered three times a day.

QID means that the dose is administered four times a day.

The highest activities of alanine aminotransferase (ALT) are found in hepatocytes and striated (skeletal and cardiac) muscle cells. Increased serum ALT activity can accompany hepatocellular injury or necrosis of striated muscle. With cell injury or death, ALT escapes from the cytosol. In addition, release of ALT from the cytosol can occur secondary to cellular necrosis or as a result of cellular injury with membrane damage. Determination of ALT activity is a relatively sensitive indicator of hepatic damage. Mechanisms of increased activity of ALT in serum include enzyme release from damaged cells or induction of enzyme activity, such as increased enzyme synthesis from drug administration. (Zeuzem, et al., Aliment Pharmacol Ther. 2006 Oct. 15; 24(8) 1133-1149).

The interleukin 28B (IL28B) gene encodes a cytokine distantly related to type I interferons and the IL-10 family. The IL28B gene, interleukin 28A (IL28A), and interleukin 29 (IL29) are three closely related cytokine genes that form a cytokine gene cluster on a chromosomal region mapped to 19q13. Expression of the cytokines encoded by the three genes can be induced by viral infection. All three cytokines have been shown to interact with a heterodimeric class II cytokine receptor that consists of interleukin 10 receptor, beta (IL10RB), and interleukin 28 receptor, alpha (IL28RA). (National Center for Biotechnology Information, Entrez Gene Entry for IL28B, Gene ID: 282617, updated on 23 Oct. 2010.)

Body mass index ("BMI") is a measurement based on a person's weight and height and is used to estimate a healthy body weight based on a person's height, assuming an average body composition. The units of BMI are kg/m$^2$.

LOD is the abbreviation for limit of detection. As used herein with regard to HCV RNA measurements, in one aspect LOD is from about 1 IU/mL to about 60 IU/mL, more preferably from about 5 IU/mL to about 30 IU/mL, and even more preferably from about 10 IU/mL to about 20 IU/mL. In a particularly preferred embodiment, the LOD is about 15 IU/mL.

GT is the abbreviation for genotype.

IU is the abbreviation for international unit, which is a measure of the amount of a substance based on biological activity or effect.

There are several recognized HCV Genotypes (1, 2, 3, 4, 5, 6, 7, 8, 9, 10 and 11), which can be further categorized by different sub-types: 1 (1a, 1b, and 1c), 2 (2a, 2b, 2c), 3 (3a and 3b), 4 (4a, 4b, 4c, 4d, and 4e), 5 (5a), 6 (6a), 7 (7a and 7b), 8 (8a and 8b), 9 (9a), 10 (10a), and 11 (11a). Genotype 1 is the predominant form found in North and South America, Europe, Asia, Australia, and New Zealand. Genotypes 2 and 3 are also widely distributed throughout North America, Europe, Australia, East Asia and some portions of Africa. In some portions of Africa, Genotype 4 predominates, while in others (such as South Africa) genotype 5 predominates. The method disclosed herein is contemplated to be independently effective for the treatment of each of the HCV genotypes, and in particular each genotype-sub-type.

The term "interferon-free" as used herein refers to a treatment regimen that does not involve the administration of interferon or pegylated interferon to the subject.

GS-7977, (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate, available from Gilead Sciences, Inc., is described and claimed in U.S. Pat. No. 7,964,580. (See also US 2010/0016251, US 2010/0298257, US 2011/0251152 and US 2012/0107278.) GS-7977 has the structure:

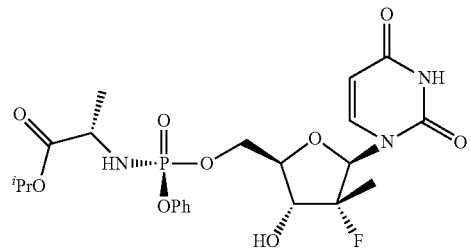 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

GS-7977 can be crystalline or amorphous. Examples of preparing crystalline and amorphous forms of GS-7977 are disclosed in US 2010/0298257 (U.S. Ser. No. 12/783,680) and US 2011/0251152 (U.S. Ser. No. 13/076,552), both of which are incorporated by reference. Polymorphic Forms 1-6 of GS-7977 disclosed in US 2010/0298257 and/or US 2011/0251152 have the following characteristic X-ray powder diffraction (XRPD) pattern 2θ-values measured according to the XRPD methods disclosed therein:

(1) 2θ-reflections)(°) at about: 5.2, 7.5, 9.6, 16.7, 18.3, and 22.2 (Form 1);

(2) 2θ-reflections)(°) at about: 5.0, 7.3, 9.4, and 18.1 (Form 1);

(3) 2θ-reflections)(°) at about: 4.9, 6.9, 9.8, 19.8, 20.6, 24.7, and 26.1 (Form 2);

(4) 2θ-reflections)(°) at about: 6.9, 9.8, 19.7, 20.6, and 24.6 (Form 3);

(5) 2θ-reflections)(°) at about: 5.0, 6.8, 19.9, 20.6, 20.9, and 24.9 (Form 4);

(6) 2θ-reflections)(°) at about: 5.2, 6.6, 7.1, 15.7, 19.1, and 25.0 (Form 5); and (7) 2θ-reflections)(°) at about: 6.1, 8.2, 10.4, 12.7, 17.2, 17.7, 18.0, 18.8, 19.4, 19.8, 20.1, 20.8, 21.8, and 23.3 (Form 6).

Polymorphic Forms 1 and 6 are alternatively characterized by the following characteristic XRPD pattern 2θ-values measured according to the methods disclosed in US 2010/0298257 (U.S. Ser. No. 12/783,680) and US 2011/0251152 (U.S. Ser. No. 13/076,552):

(1) 2θ-reflections)(°) at about: 5.0 and 7.3 (Form 1); and (2) 2θ-reflections)(°) at about: 6.1 and 12.7 (Form 6).

In one aspect, the disclosed composition comprises polymorphic Form 6 of GS-7977. It has been found that Form 6 has a melt onset of approximately 121° C. and is not hygroscopic, with less than 0.2% moisture sorption at room temperature and 90% RH. Form 6 is chemically stable when stored under opened conditions at 40° C./75% RH for 30 days.

In one aspect, GS-7977 is substantially free from its corresponding phosphorous-based diastereomer (S)-isopropyl 2-(((R)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino) propanoate. In one embodiment, GS-7977 is at least 95% free from its corresponding phosphorous-based diastereomer. In another embodiment, GS-7977 is at least 97% free from its corresponding phosphorous-based diastereomer. In another embodiment, GS-7977 is at least 99% free from its corresponding phosphorous-based diastereomer. In a further embodiment, GS-7977 is at least 99.9% free from its corresponding phosphorous-based diastereomer.

Ribavirin, 1-β-D-ribofuranosyl-1H-1,2,4-triazole-3-carboxamide, is described in the Merck Index (12th Edition), monograph no. 8365. (See also U.S. Pat. No. 4,530,901.)

As used herein, "treatment" or "treating" is an approach for obtaining beneficial or desired clinical results. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. The term "treatment" of an HCV infection, as used herein, also includes treatment or prophylaxis of a disease or a condition associated with or mediated by HCV infection, or the clinical symptoms thereof.

Compositions and Unit Dosage Forms

A first embodiment is directed to a composition for the treatment of hepatitis C virus (HCV) comprising a) GS-7977, and b) a pharmaceutically acceptable excipient.

In a first aspect of the first embodiment, the composition for the treatment of HCV comprises from about 25% to about 35% w/w of GS-7977. In another aspect, the composition comprises from about 30% to about 35% w/w of GS-7977. In another aspect, the composition comprises from about 25%, about 26%, about 27%, about 28%, about 29%, about 30%, about 31%, about 32%, about 33%, about 34%, or about 35% w/w of GS-7977. In one subembodiment, the composition comprises about 30% w/w of GS-7977. In another subembodiment, the composition comprises about 33% w/w of GS-7977. In another subembodiment, the composition comprises about 33.33% w/w of GS-7977.

In a second aspect of the first embodiment, the composition comprises crystalline GS-7977. In one subembodiment, the composition comprises crystalline GS-7977 having XRPD 2θ-reflections)(°) at about: (1) 5.2, 7.5, 9.6, 16.7, 18.3, and 22.2; (2) 5.0, 7.3, 9.4, and 18.1; (3) 4.9, 6.9, 9.8, 19.8, 20.6, 24.7, and 26.1; (4) 6.9, 9.8, 19.7, 20.6, and 24.6; (5) 5.0, 6.8, 19.9, 20.6, 20.9, and 24.9; (6) 5.2, 6.6, 7.1, 15.7, 19.1, and 25.0; or (7) 6.1, 8.2, 10.4, 12.7, 17.2, 17.7, 18.0, 18.8, 19.4, 19.8, 20.1, 20.8, 21.8, and 23.3. In another subembodiment, the composition comprises crystalline GS-7977 having XRPD 2θ-reflections)(°) at about: (1) 5.0 and 7.3; or (2) 6.1 and 12.7. In one preferred subembodiment, the composition comprises crystalline GS-7977 having XRPD 2θ-reflections)(°) at about: (1) 5.2, 7.5, 9.6, 16.7, 18.3, and 22.2; or (2) XRPD 2θ-reflections) (°) at about: 5.0, 7.3, 9.4, and 18.1. In another preferred subembodiment, the composition comprises crystalline GS-7977 having XRPD 2θ-reflections)(°) at about 6.1, 8.2, 10.4, 12.7, 17.2, 17.7, 18.0, 18.8, 19.4, 19.8, 20.1, 20.8, 21.8, and 23.3. In another preferred subembodiment, the composition comprises crystalline GS-7977 having XRPD 2θ-reflections)(°) at about: 5.0 and 7.3. In a further preferred subembodiment, the composition comprises crystalline GS-7977 having XRPD 2θ-reflections)(°) at about 6.1 and 12.7.

In a third aspect of the first embodiment, the pharmaceutically acceptable excipient comprises at least one of a diluent, a disintegrant, a glidant, and a lubricant.

In one subembodiment, the diluent is selected from the group consisting of calcium carbonate, dicalcium phosphate, dry starch, calcium sulfate, cellulose, compressible sugars, confectioner's sugar, dextrates, dextrin, dextrose, dibasic calcium phosphate dihydrate, glyceryl palmitostearate, hydrogenated vegetable oil (type I), inositol, kaolin, lactose, magnesium carbonate, magnesium oxide, maltodextrin, mannitol, microcrystalline cellulose, polymethacrylates, potassium chloride, powdered cellulose, powdered sugar, pregelatinized starch, sodium chloride, sorbitol, starch, sucrose, sugar spheres, talc, tribasic calcium phosphate, and combinations thereof. In a preferred subembodiment, the diluent is selected from the group consisting of dicalcium phosphate, cellulose, compressible sugars, dibasic calcium phosphate dehydrate, lactose, mannitol, microcrystalline cellulose, starch, tribasic calcium phosphate, and combinations thereof. In another preferred subembodiment, the diluent is selected from the group consisting of mannitol, microcrystalline cellulose, and combinations thereof.

In another subembodiment, the disintegrant is selected from the group consisting of agar, alginic acid, bentonite, carboxymethylcellulose calcium, carboxymethylcellulose sodium, carboxymethylcellulose, cellulose, a cation exchange resin, cellulose, gums, citrus pulp, colloidal silicon dioxide, corn starch, croscarmellose sodium (e.g., Ac-Di-Sol®), crospovidone, guar gum, hydrous aluminum silicate, an ion exchange resin (e.g., polyacrin potassium), magnesium aluminum silicate, methyl cellulose, microcrystalline cellulose, modified cellulose gum, modified corn starch, montmorillonite clay, natural sponge, polyacrilin potassium, potato starch, powdered cellulose, povidone, pregelatinized starch, sodium alginate, sodium bicarbonate in admixture with an acidulant such as tartaric acid or citric acid, sodium starch glycolate, starch, silicates (e.g., Veegum® HV), and combinations thereof. In a preferred subembodiment, the disintegrant is selected from the group consisting of croscarmellose sodium (e.g., Ac-Di-Sol®), crospovidone, microcrystalline cellulose, modified corn starch, povidone, pregelatinized starch, sodium starch glycolate, and combinations thereof. In another preferred subembodiment, the disintegrant is croscarmellose sodium (e.g., Ac-Di-Sol®).

In another subembodiment, the glidant is selected from the group consisting of colloidal silicon dioxide, talc, starch, starch derivatives, and combinations thereof. In a preferred subembodiment, the glidant comprises colloidal silicon dioxide.

In another subembodiment, the lubricant is selected from the group consisting of calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and combinations thereof. In a preferred subembodiment, the lubricant is selected from the group consisting of calcium stearate, magnesium stearate, polyethylene glycol, sodium stearyl fumarate, stearic acid, talc, and combinations thereof. In another preferred subembodiment, the lubricant is magnesium stearate.

In another subembodiment, the pharmaceutically acceptable excipient comprises: a) about 55% w/w to about 65% w/w of a diluent; b) about 2.5% w/w to about 7.5% w/w of a disintegrant; c) about 0.25% w/w to about 0.75% w/w of a glidant; and d) about 1.25% w/w to about 1.75% w/w of a lubricant. In a preferred subembodiment, the pharmaceutically acceptable excipient comprises a) about 60% w/w a diluent; b) about 5% w/w of a disintegrant; c) about 0.5% w/w a glidant; and d) about 1.5% w/w a lubricant. In another preferred subembodiment, the pharmaceutically acceptable excipient comprises a) about 60% w/w a diluent comprising mannitol and/or microcrystalline cellulose; b) about 5% w/w of croscarmellose sodium; c) about 0.5% w/w of colloidal silicon dioxide; and d) about 1.5% w/w of magnesium stearate. In another preferred subembodiment, the pharmaceutically acceptable excipient comprises a) about 30% w/w of mannitol and about 30% w/w of microcrystalline cellulose; b) about 5% w/w of croscarmellose sodium; c) about 0.5% w/w of colloidal silicon dioxide; and d) about 1.5% w/w of magnesium stearate.

In a fourth aspect of the first embodiment, the composition further comprises a coating agent. In one subembodiment, the coating agent is formed from an aqueous film coat composition, wherein the aqueous film coat composition comprises a film-forming polymer, water and/or an alcohol as a vehicle, and optionally one or more adjuvants such as are known in the film-coating art. In another subembodiment, the coating agent is selected from the group consisting of hydroxypropylmethylcellulose, hydroxypropylcellulose, methylcellulose, ethylcellulose, hydroxyethylcellulose, cellulose acetate phthalate, sodium ethyl cellulose sulfate, carboxymethyl cellulose, polyvinylpyrolidone, zein, and an acrylic polymer (e.g., methacrylic acid/methacrylic acid ester copolymers such as methacrylic acid/methylmethacrylate copolymers, etc.), and a polyvinyl alcohol. In another subembodiment, the coating agent comprises a polyvinyl alcohol.

In a fifth aspect of the first embodiment, the composition comprises about 25% w/w to about 35% w/w of crystalline GS-7977; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In one subembodiment, the composition comprises about 30% w/w to about 35% w/w of crystalline GS-7977; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition comprises about 30% w/w of crystalline GS-7977; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In one subembodiment, the composition comprises about 30% w/w of crystalline GS-7977 having XRPD 2θ-reflections)(°) at about 6.1, 8.2, 10.4, 12.7, 17.2, 17.7, 18.0, 18.8, 19.4, 19.8, 20.1, 20.8, 21.8, and 23.3; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition comprises about 30% w/w of crystalline GS-7977 having XRPD 2θ-reflections)(°) at about 6.1 and 12.7; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition comprises about 33% w/w of crystalline GS-7977; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition comprises about 33% w/w of crystalline GS-7977 having XRPD 2θ-reflections)(°) at about 6.1, 8.2, 10.4, 12.7, 17.2, 17.7, 18.0, 18.8, 19.4, 19.8, 20.1, 20.8, 21.8, and 23.3; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition comprises about 33% w/w of crystalline GS-7977 having XRPD 2θ-reflections)(°) at about 6.1 and 12.7; about 30% w/w of mannitol and about 30% w/w of microcrystalline cellulose; about 5% w/w of croscarmellose sodium; about 0.5% w/w of colloidal silicon dioxide; and about 1.5% w/w of magnesium stearate. In another subembodiment, the composition further comprises a coating agent.

A second embodiment is directed to a unit dosage form for the treatment of hepatitis C virus (HCV), said composition comprising a) about 400 mg of GS-7977, and b) a pharmaceutically acceptable excipient.

In a first aspect of the second embodiment, the unit dosage form comprises crystalline GS-7977. In one subembodiment, the composition comprises crystalline GS-7977 having XRPD 2θ-reflections)(°) at about: (1) 5.2, 7.5, 9.6, 16.7, 18.3, and 22.2; (2) 5.0, 7.3, 9.4, and 18.1; (3) 4.9, 6.9, 9.8, 19.8, 20.6, 24.7, and 26.1; (4) 6.9, 9.8, 19.7, 20.6, and 24.6; (5) 5.0, 6.8, 19.9, 20.6, 20.9, and 24.9; (6) 5.2, 6.6, 7.1, 15.7, 19.1, and 25.0; or (7) 6.1, 8.2, 10.4, 12.7, 17.2, 17.7, 18.0, 18.8, 19.4, 19.8, 20.1, 20.8, 21.8, and 23.3. In another subembodiment, the composition comprises crystalline GS-7977 having XRPD 2θ-reflections)(°) at about: (1) 5.0 and 7.3; or (2) 6.1 and 12.7. In one preferred subembodiment, the unit dosage form comprises crystalline GS-7977 having XRPD 2θ-reflections)(°) at about: (1) 5.2, 7.5, 9.6, 16.7, 18.3, and 22.2; or (2) XRPD 2θ-reflections) (°) at about: 5.0, 7.3, 9.4, and 18.1. In another preferred subembodiment, the unit dosage form comprises crystalline GS-7977 having XRPD 2θ-reflections)(°) at about 6.1, 8.2, 10.4, 12.7, 17.2, 17.7, 18.0, 18.8, 19.4, 19.8, 20.1, 20.8, 21.8, and 23.3. In another preferred subembodiment, the composition comprises crystalline GS-7977 having XRPD 2θ-reflections)(°) at about: 5.0 and 7.3. In a further preferred subembodiment, the composition comprises crystalline GS-7977 having XRPD 2θ-reflections)(°) at about 6.1 and 12.7.

In a second aspect of the second embodiment, the pharmaceutically acceptable excipient comprises at least one of a diluent, a disintegrant, a glidant, and a lubricant.

In a one subembodiment, diluent is selected from the group consisting of calcium carbonate, dicalcium phosphate, dry starch, calcium sulfate, cellulose, compressible sugars, confectioner's sugar, dextrates, dextrin, dextrose, dibasic calcium phosphate dihydrate, glyceryl palmitostearate, hydrogenated vegetable oil (type I), inositol, kaolin, lactose, magnesium carbonate, magnesium oxide, maltodextrin, mannitol, microcrystalline cellulose, polymethacrylates, potassium chloride, powdered cellulose, powdered sugar, pregelatinized starch, sodium chloride, sorbitol, starch, sucrose, sugar spheres, talc, tribasic calcium phosphate, and combinations thereof. In a preferred subembodiment, the diluent is selected from the group consisting of dicalcium phosphate, cellulose, compressible sugars, dibasic calcium phosphate dehydrate, lactose, mannitol, microcrystalline cellulose, starch, tribasic calcium phosphate, and combinations thereof. In another preferred subembodiment, the diluent is selected from the group consisting of mannitol, microcrystalline cellulose, and combinations thereof.

In another subembodiment, the disintegrant is selected from the group consisting of agar, alginic acid, bentonite, carboxymethylcellulose calcium, carboxymethylcellulose sodium, carboxymethylcellulose, cellulose, a cation exchange resin, cellulose, gums, citrus pulp, colloidal silicon dioxide, corn starch, croscarmellose sodium (e.g., Ac-Di-Sol®), crospovidone, guar gum, hydrous aluminum silicate, an ion exchange resin (e.g., polyacrin potassium), magnesium aluminum silicate, methyl cellulose, microcrystalline cellulose, modified cellulose gum, modified corn starch, montmorillonite clay, natural sponge, polyacrilin potassium, potato starch, powdered cellulose, povidone, pregelatinized starch, sodium alginate, sodium bicarbonate in admixture with an acidulant such as tartaric acid or citric acid, sodium starch glycolate, starch, silicates (e.g., Veegum® HV), and combinations thereof. In a preferred subembodiment, the disintegrant is selected from the group consisting of croscarmellose sodium (e.g., Ac-Di-Sol), crospovidone, microcrystalline cellulose, modified corn starch, povidone, pregelatinized starch, sodium starch glycolate, and combinations thereof. In another preferred subembodiment, the disintegrant is croscarmellose sodium (e.g., Ac-Di-Sol).

In another subembodiment, the glidant is selected from the group consisting of colloidal silicon dioxide, talc, starch, starch derivatives, and combinations thereof. In a preferred subembodiment, the glidant comprises colloidal silicon dioxide.

In another subembodiment, the lubricant is selected from the group consisting of calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and combinations thereof. In a preferred subembodiment, the lubricant is selected from the group consisting of calcium stearate, magnesium stearate, polyethylene glycol, sodium stearyl fumarate, stearic acid, talc, and combinations thereof. In another preferred subembodiment, the lubricant is magnesium stearate.

In another subembodiment, the pharmaceutically acceptable excipient comprises: a) about 660 mg to about 780 mg of a diluent; b) about 30 mg to about 90 mg of a disintegrant; c) about 3 mg to about 9 mg of a glidant; and d) about 15 mg to about 21 mg of a lubricant. In a preferred subembodiment, the pharmaceutically acceptable excipient comprises a) about 710 mg to about 720 mg of a diluent; b) about 60 mg of a disintegrant; c) about 6 mg of a glidant; and d) about 18 mg of a lubricant. In another preferred subembodiment, the pharmaceutically acceptable excipient comprises a) about 716 mg of a diluent; b) about 60 mg of a disintegrant; c) about 6 mg of a glidant; and d) about 18 mg of a lubricant. In another preferred subembodiment, the pharmaceutically acceptable excipient comprises a) about 710 mg to about 720 mg of a diluent comprising mannitol and/or microcrystalline cellulose; b) about 60 mg of croscarmellose sodium; c) about 6 mg of colloidal silicon dioxide; and d) about 18 mg of magnesium stearate. In another preferred subembodiment, the pharmaceutically acceptable excipient comprises a) about 716 mg of a diluent comprising mannitol and/or microcrystalline cellulose; b) about 60 mg of croscarmellose sodium; c) about 6 mg of colloidal silicon dioxide; and d) about 18 mg of magnesium stearate. In another preferred subembodiment, the pharmaceutically acceptable excipient comprises a) about 360 mg of mannitol and about 356 mg of microcrystalline cellulose; b) about 60 mg of croscarmellose sodium; c) about 6 mg of colloidal silicon dioxide; and d) about 18 mg of magnesium stearate.

In a third aspect of the second embodiment, the unit dosage form further comprises a coating agent. In one subembodiment, the coating agent further comprises a taste-masking agent. In one subembodiment, the coating agent is formed from an aqueous film coat composition, wherein the aqueous film coat composition comprises a film-forming polymer, water and/or an alcohol as a vehicle, and optionally one or more adjuvants such as are known in the film-coating art. In another subembodiment, the coating agent is selected from among hydroxypropylmethylcellulose, hydroxypropylcellulose, methylcellulose, ethylcellulose, hydroxyethylcellulose, cellulose acetate phthalate, sodium ethyl cellulose sulfate, carboxymethyl cellulose, polyvinylpyrolidone, zein, and an acrylic polymer (e.g., methacrylic acid/methacrylic acid ester copolymers such as methacrylic acid/methylmethacrylate copolymers, etc.), and a polyvinyl alcohol. In another subembodiment, the coating agent comprises a polyvinyl alcohol. In another subembodiment, the unit dosage comprises about 24 mg to about 60 mg of a coating agent. In another subembodiment, the unit dosage comprises about 36 mg to about 48 mg of a coating agent. In another subembodiment, the unit dosage comprises about 36 mg of a coating agent. In another subembodiment, the unit dosage comprises about 36 mg of a coating agent that further comprises a taste-masking agent.

In a fourth aspect of the second embodiment, the unit dosage form comprises about 400 mg of crystalline GS-7977; about 360 mg of mannitol and about 356 mg of microcrystalline cellulose; about 60 mg of croscarmellose sodium; about 6 mg of colloidal silicon dioxide; and about 18 mg of magnesium stearate. In one subembodiment, the unit dosage form comprises about 400 mg of crystalline GS-7977 having XRPD 2θ-reflections)(°) at about 6.1, 8.2, 10.4, 12.7, 17.2, 17.7, 18.0, 18.8, 19.4, 19.8, 20.1, 20.8, 21.8, and 23.3; about 360 mg of mannitol and about 356 mg of microcrystalline cellulose; about 60 mg of croscarmellose sodium; about 6 mg of colloidal silicon dioxide; and about 18 mg of magnesium stearate. In another subembodiment, the unit dosage form comprises about 400 mg of crystalline GS-7977 having XRPD 2θ-reflections)(°) at about 6.1 and 12.7; about 360 mg of mannitol and about 356 mg of microcrystalline cellulose; about 60 mg of croscarmellose sodium; about 6 mg of colloidal silicon dioxide; and about 18 mg of magnesium stearate.

In a fifth aspect of the second embodiment, the unit dosage form comprises a capsule or a tablet. In one subembodiment, the unit dosage form comprises a tablet. In another subembodiment, the unit dosage form comprises a tablet and further comprises a coating agent.

With respect to the coating agent, film-forming polymers are typically provided in either aqueous or organic solvent-based solutions or aqueous dispersions. However, the polymers may be provided in dry form, alone or in a powdery mixture with other components (e.g., a plasticizer and/or colorant), which is made into a solution or dispersion by the user by admixing with the aqueous vehicle.

It will be appreciated that the aqueous film coat composition further comprises water as a vehicle for the other components, to facilitate their delivery to the surface of the unit dosage form. The vehicle may optionally further comprise one or more water soluble solvents, e.g., an alcohol and/or a ketone. Examples of an alcohol include but are not limited to methanol, isopropanol, propanol, etc. A non-limiting example for the ketone is acetone. The skilled artisan can select appropriate vehicle components to provide good interaction between the film-forming polymer and the vehicle to ensure good film properties. In general, polymer-vehicle interaction is designed to yield maximum polymer chain extension to produce films having the greatest cohesive strength and thus mechanical properties. The components are also selected to provide good deposition of the film-forming polymer onto the surface of the unit dosage form, such that a coherent and adherent film is achieved.

Suitable aqueous film coating compositions include those commercially available from Colorcon, Inc. of West Point, Pa., under the trade name OPADRY and OPADRY II (non-limiting examples includes Opadry II Purple and Opadry II Yellow).

A third embodiment is directed to a method of treating a subject infected with hepatitis C virus comprising administering to the subject a composition comprising a) about 25-35% w/w of GS-7977, and b) a pharmaceutically acceptable excipient.

In a first aspect of the third embodiment, the composition comprising a) about 25-35% w/w of GS-7977, and b) a pharmaceutically acceptable excipient is administered to the subject in combination with ribavirin.

In a second aspect of the third embodiment, the subject is a human.

A fourth embodiment is directed to a method of treating a subject infected with hepatitis C virus comprising administering to the subject a unit dosage form comprising a) about 400 mg of GS-7977, and b) a pharmaceutically acceptable excipient.

In a first aspect of the fourth embodiment, the a unit dosage form comprising a) about 400 mg of GS-7977, and b) a pharmaceutically acceptable excipient is administered to the subject in combination with ribavirin.

In a second aspect of the fourth embodiment, the subject is a human.

Tablet Preparation

The choice of particular types and amounts of excipients, and tabletting technique employed depends on the further properties of GS-7977 and the excipients, e.g., compressibility, flowability, particle size, compatibility, and density. In this regard, reference is made Remington: *The Science and Practice of Pharmacy* 2006, 21st edition, Lippincott Williams & Wilkins; see also Handbook of Pharmaceutical Excipients 1994, edited by A. Wade and P. J. Weller, The Pharmaceutical Press, 2nd Edition, London. A skilled formulation scientist may modify the formulations within the teachings of the specification to provide numerous formulations for a particular route of administration without rendering compositions containing GS-7977 unstable or compromising their therapeutic activity.

Tablets may be prepared according to methods known in the art, including dry granulation (e.g., roller compaction), wet granulation (e.g., fluid bed granulation and high shear granulation), and direct compression, and the type of excipients used will vary accordingly. It has been found that dry granulation is particularly suitable for providing high strength, low breakage tablets comprising relatively high concentrations of crystalline GS-7977 (e.g., about 33%), on a scale suitable for commercial production. Suitable dry granulated tablets comprise granules comprising GS-7977 and one or more of a diluent, a disintegrant, a glidant, and a lubricant, wherein the granules are mixed with one or more of a diluent, a disintegrant, a glidant, and a lubricant to form a granulation mixture that is compressed to form tablets.

A fifth embodiment is directed to a process for preparing a tablet composition comprising about 400 mg of GS-7977, said process comprising blending an intragranular composition and an extragranular composition to obtain a blended composition; compressing the blended composition to obtain a tablet composition; and optionally coating the tablet composition.

In a first aspect of the fifth embodiment, the intragranular composition comprises GS-7977, a first intragranular diluent, optionally a second intragranular diluent, an intragranular disintegrant, an intragranular glidant, and an intragranular lubricant; and the extragranular composition comprises a first extragranular diluent, optionally a second extragranular diluent, an extragranular disintegrant, an extragranular glidant, and an extragranular lubricant, wherein the first intragranular diluent, the second intragranular diluent, the first extragranular diluent, and the second extragranular diluent are the same or different, the intragranular disintegrant and the extragranular disintegrant are the same or different, the intragranular glidant and the extragranular glidant are the same or different, and the intragranular lubricant and the extragranular lubricant are the same or different.

In a second aspect of the fifth embodiment, the intragranular composition comprises GS-7977, a first intragranular diluent, an intragranular disintegrant, an intragranular glidant, and an intragranular lubricant; and the extragranular composition comprises a first extragranular diluent, a second extragranular diluent, an extragranular disintegrant, an extragranular glidant, and an extragranular lubricant, wherein the first intragranular diluent, the first extragranular diluent, and the second extragranular diluent are the same or different, the intragranular disintegrant and the extragranular disintegrant are the same or different, the intragranular glidant and the extragranular glidant are the same or different, and the intragranular lubricant and the extragranular lubricant are the same or different.

In a third aspect of the fifth embodiment, the intragranular composition comprises GS-7977, a first intragranular diluent, a second intragranular diluent, an intragranular disintegrant, an intragranular glidant, and an intragranular lubricant; and the extragranular composition comprises a first extragranular diluent, an extragranular disintegrant, an extragranular glidant, and an extragranular lubricant, wherein the first intragranular diluent, the second intragranular diluent, and the first extragranular diluent are the same or different, the intragranular disintegrant and the extragranular disintegrant are the same or different, the intragranular glidant and the extragranular glidant are the same or different, and the intragranular lubricant and the extragranular lubricant are the same or different.

A fourth aspect of the fifth embodiment comprises at least one of the following steps:

(1) Sifting/Blending: GS-7977 and pharmaceutically acceptable excipients are sifted and/or blended during the formulation process. In one non-limiting example, first, GS-7977 and intragranular excipients (first diluent, optional second diluent, glidant, disintegrant; except for the intragranular lubricant) are sifted through a 20-mesh screen, added to a blender, and blended for a first blending time period to produce an initial blend. In one aspect, the first blending time period ranges from about 5 to about 30 minutes. Separately, an intragranular lubricant is passed through a 20-mesh screen, mixed with a portion of the initial blend, added to the blender, and blended for a second blending time period. In one aspect, the second blending time period is from about 1 minute to about 10 minutes. In another aspect, the second blending time period is from about 1 minute to about 5 minutes. In another aspect, the second blending time period is from about 5 minutes to about 10 minutes. Second, extragranular excipients (first diluent, optional second diluent, glidant, disintegrant) (except for the extragranular lubricant) are sifted through a 20-mesh screen and used in the final blending. It is contemplated that the blending time periods may increase as the scale of the formulation process increases.

(2) Dry Granulation:

(A) Roller Compaction: GS-7977 and pharmaceutically acceptable excipients are passed through a roller compactor to product compacts. Compacts are then milled (below) to achieve granules. In one non-limiting example, a blend comprising GS-7977, intragranular excipients, and lubricant, is passed through a roller compactor until granulation is achieved. The non-limiting example has the following parameters: granulator speed ranges from about 50 to about 90 rpm, more specifically about 70 rpm; compactor speed ranges from about 4 to about 6 rpm, more specifically about 5 rpm; and pressure ranges from about 65 to about 100 barr, more specifically about 75 to about 100 bar.

(B) Milling (preparation of milled/sifted granule): GS-7977 and pharmaceutically acceptable excipients are milled and/or sifted. In one non-limiting example, after GS-7977 and intragranular excipients have passed through the roller compactor, the material is passed/forced through a 20-mesh screen using a Comill or Fitz Mill, and then sifted with a 60 mesh screen. In this non-limiting example, material which remains on the 60 mesh screen is considered to be an acceptable granule, but material which passes through the 60 mesh screen is considered fines and is re-circulated through the roller compactor. This process is repeated until the percentage of fines is less than 20%. In one non-limiting example, the mill speed ranges from about 50 to about 90 rpm, more specifically about 70 rpm, (3) Final Blending: Granules comprising GS-7977 and intragranular excipients that have been milled/sifted are blended with extragranular excipients in a final blending. In one non-limiting example, the milled/sifted granules comprising GS-7977 and intragranular exceipients are added to a blender (e.g., a double-cone blender, a bin blender, or a V-shell blender) along with extragranular excipients (first diluent and/or second diluent, glidant, and disintegrant) and blended for about 10 to about 30 minutes. The extragranular lubricant is passed through a 20-mesh screen and added to the blend. The blend/mixture is blended for about 5 minutes. It is contemplated that the blending time periods may increase as the scale of the formulation process increases.

(4) Compressing: The final blend is compressed into tablets using a tablet press (e.g., a Globe Pharma Mini Press).

(5) Optionally, tablets are film-coated with a film-coating agent.

In a fifth aspect of the fifth embodiment, GS-7977 is blended with intragranular excipients comprising microcrystalline cellulose, mannitol, croscarmellose sodium and colloidal silicon dioxide in a blender. The mixture is milled and blended with a portion of magnesium stearate, then dry granulated using a roller compactor and mill. The resulting granules are then blended with extragranular excipients comprising microcrystalline cellulose, croscarmellose sodium, and colloidal silicon dioxide. An additional portion of magnesium stearate is added and the resulting composition is mixed to yield a powder blend comprising 33.33% w/w GS-7977. The powder blend is compressed into tablet cores to yield tablets comprising about 400 mg of GS-7977. The tablet cores are film-coated, and the resulting film-coated tablets are then packaged.

The embodiments described herein may be modified by one of ordinary skill without straying from the expressed intent using materials and methods described in *Remington: The Science and Practice of Pharmacy* 1995, edited by E. W. Martin, Mack Publishing Company, 19th edition, Easton, Pa.; see also Handbook of Pharmaceutical Excipients 1994, edited by A. Wade and P. J. Weller, The Pharmaceutical Press, 2nd Edition, London. One of ordinary skill may modify the formulations within the teachings of the specification to provide numerous formulations without rendering compositions containing GS-7977 unstable or compromising its therapeutic activity. The following non-limiting examples provide further guidance related to additional aspects of the disclosed methods and compositions.

Methods of Treatment

A sixth embodiment is directed to a method for treating a subject infected with hepatitis C virus comprising administering to the subject for a time period an effective amount of GS-7977 and an effective amount of ribavirin.

In a first aspect of the sixth embodiment, the time period is selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is 12 weeks. In another subembodiment the time period is 8 weeks.

In a second aspect of the sixth embodiment, the effective amount of GS-7977 is a daily dose selected from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg. In one subembodiment, the daily dose of GS-7977 is administered to the subject QD, BID, TID, or QID. In another subembodiment, a daily dose of about 400 mg of GS-7977 is administered to the subject QD, BID, TID, or QID. In another subembodiment, a daily dose of about 400 mg of GS-7977 is administered to the subject QD.

In a third aspect of the sixth embodiment, an effective amount of GS-7977 is administered to the subject in combination with an effective amount of ribavirin, wherein the administration is concurrent or alternative.

In a fourth aspect of the sixth embodiment, the effective amount of ribavirin is a daily dose selected from about 600 mg to about 1400 mg, and from about 800 mg to about 1200 mg. In one subembodiment, the effective amount of ribavirin is a daily dose of about 1000 mg to about 1200 mg. In another subembodiment, the effective amount of ribavirin is a daily dose of about 1000 mg to about 1200 mg based on the subject's body weight. In another subembodiment, the effective amount of ribavirin is a daily dose of about 800 mg. In another subembodiment, the daily dose of ribavirin is administered to the subject QD, BID, TID, or QID. In a further subembodiment, the daily dose of ribavirin is administered to the subject BID.

In a fifth aspect of the sixth embodiment, a daily dose of about 400 mg of GS-7977 is administered to the subject in combination with a daily dose of about 800 mg to about 1200 mg of ribavirin. In one subembodiment, a daily dose of about 400 mg of GS-7977 is administered to the subject in combination with a daily dose of about 800 mg of ribavirin. In another subembodiment, a daily dose of about 400 mg of GS-7977 is administered to the subject in combination with a daily dose of about 1000 mg to about 1200 mg of ribavirin.

In a sixth aspect of the sixth embodiment, the subject is infected with HCV genotype 1, 2, 3, 4, 5 or 6, or any combination thereof. In one subembodiment, the subject is infected with HCV genotype 1, 2, or 3, or any combination thereof.

In a seventh aspect of the sixth embodiment, the subject has an undetectable amount of HCV RNA for at least 12 weeks after the end of the time period. In one subembodiment, the subject has an undetectable amount of HCV RNA for at least 24 weeks after the end of the time period. In another subembodiment, the subject has an undetectable amount of HCV RNA for at least 36 weeks after the end of the time period. In a further subembodiment, the subject has an undetectable amount of HCV RNA for at least 48 weeks after the end of the time period.

In an eighth aspect of the sixth embodiment, the subject is a human.

In a ninth aspect of the sixth embodiment, an effective amount of GS-7977 and an effective amount of ribavirin are administered to the subject according to an interferon-free treatment regimen. In one subembodiment, the interferon-free treatment regimen consists of administering an effective amount of GS-7977 and an effective amount of ribavirin to the subject for the time period.

In a tenth aspect of the sixth embodiment, the effective amount of GS-7977 comprises a composition comprising GS-7977 and at least one pharmaceutically acceptable excipient as disclosed herein.

In an eleventh aspect of the sixth embodiment, the effective amount of GS-7977 comprises a unit dosage form comprising GS-7977 and at least one pharmaceutically acceptable excipient as disclosed herein.

A seventh embodiment is directed to a method of treating a subject infected with hepatitis C virus, said method comprising administering to the subject for a time period an effective amount of GS-7977 and an effective amount of ribavirin sufficient to produce an undetectable amount of HCV RNA in the subject for at least 12 weeks after the end of the time period.

In a first aspect of the seventh embodiment, the time period is selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is 12 weeks. In another subembodiment the time period is 8 weeks.

In a second aspect of the seventh embodiment, the effective amount of GS-7977 is a daily dose selected from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg. In one subembodiment, the daily dose of GS-7977 is administered to the subject QD, BID, TID, or QID. In another subembodiment, a daily dose of about 400 mg of GS-7977 is administered to the subject QD, BID, TID, or QID. In another subembodiment, a daily dose of about 400 mg of GS-7977 is administered to the subject QD.

In a third aspect of the seventh embodiment, an effective amount of GS-7977 is administered to the subject in combination with an effective amount of ribavirin, wherein the administration is concurrent or alternative.

In a fourth aspect of the seventh embodiment, the effective amount of ribavirin is a daily dose selected from about 600 mg to about 1400 mg, and from about 800 mg to about 1200 mg. In one subembodiment, the effective amount of ribavirin is a daily dose of about 1000 mg to about 1200 mg. In another subembodiment, the effective amount of ribavirin is a daily dose of about 1000 mg to about 1200 mg based on the subject's body weight. In another subembodiment, the effective amount of ribavirin is a daily dose of about 800 mg. In another subembodiment, the daily dose of ribavirin is administered to the subject QD, BID, TID, or QID. In a further subembodiment, the daily dose of ribavirin is administered to the subject BID.

In a fifth aspect of the seventh embodiment, a daily dose of about 400 mg of GS-7977 is administered to the subject in combination with a daily dose of about 800 mg to about 1200 mg of ribavirin. In one subembodiment, a daily dose of about 400 mg of GS-7977 is administered to the subject in combination with a daily dose of about 800 mg of ribavirin. In another subembodiment, a daily dose of about 400 mg of GS-7977 is administered to the subject in combination with a daily dose of about 1000 mg to about 1200 mg of ribavirin.

In a sixth aspect of the seventh embodiment, the subject is infected with HCV genotype 1, 2, 3, 4, 5 or 6, or any combination thereof. In one subembodiment, the subject is infected with HCV genotype 1, 2, 3, or any combination thereof.

In a seventh aspect of the seventh embodiment, the subject has an undetectable amount of HCV RNA for at least 24 weeks after the end of the time period. In one subembodiment, the subject has an undetectable amount of HCV RNA for at least 36 weeks after the end of the time period. In another subembodiment, the subject has an undetectable amount of HCV RNA for at least 48 weeks after the end of the time period.

In an eighth aspect of the seventh embodiment, the subject is a human.

In a ninth aspect of the seventh embodiment, an effective amount of GS-7977 and an effective amount of ribavirin are administered to the subject according to an interferon-free treatment regimen. In one subembodiment, the interferon-free treatment regimen consists of administering an effective amount of GS-7977 and an effective amount of ribavirin to the subject for the time period.

In a tenth aspect of the seventh embodiment, the effective amount of GS-7977 comprises a composition comprising GS-7977 and at least one pharmaceutically acceptable excipient as disclosed herein.

In an eleventh aspect of the seventh embodiment, the effective amount of GS-7977 comprises a unit dosage form comprising GS-7977 and at least one pharmaceutically acceptable excipient as disclosed herein.

An eighth embodiment is directed to a method of treating a human infected with hepatitis C virus, said method comprising administering to the human for a time period an effective amount of GS-7977 and an effective amount of ribavirin sufficient to produce an undetectable amount of HCV RNA in the human for at least 12 weeks after the end of the time period.

In a first aspect of the eighth embodiment, the time period is selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is 12 weeks. In another subembodiment the time period is 8 weeks.

In a second aspect of the eighth embodiment, the effective amount of GS-7977 is a daily dose selected from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg. In one subembodiment, the daily dose of GS-7977 is administered to the human QD, BID, TID, or QID. In another subembodiment, a daily dose of about 400 mg of GS-7977 is administered to the human QD, BID, TID, or QID. In another subembodiment, a daily dose of about 400 mg of GS-7977 is administered to the human QD.

In a third aspect of the eighth embodiment, an effective amount of GS-7977 is administered to the subject in combination with an effective amount of ribavirin, wherein the administration is concurrent or alternative.

In a fourth aspect of the eighth embodiment, the effective amount of ribavirin is a daily dose selected from about 600 mg to about 1400 mg, and from about 800 mg to about 1200 mg. In one subembodiment, the effective amount of ribavirin is a daily dose of about 1000 mg to about 1200 mg. In another subembodiment, the effective amount of ribavirin is a daily dose of about 1000 mg to about 1200 mg based on the human's body weight. In another subembodiment, the effective amount of ribavirin is a daily dose of about 800 mg. In another subembodiment, the daily dose of ribavirin is administered to the human QD, BID, TID, or QID. In a further subembodiment, the daily dose of ribavirin is administered to the human BID.

In a fifth aspect of the eighth embodiment, a daily dose of about 400 mg of GS-7977 is administered to the human in combination with a daily dose of about 800 mg to about 1200 mg of ribavirin. In one subembodiment, a daily dose of about 400 mg of GS-7977 is administered to the human in combination with a daily dose of about 800 mg of ribavirin. In another subembodiment, a daily dose of about 400 mg of GS-7977 is administered to the human in combination with a daily dose of about 1000 mg to about 1200 mg of ribavirin.

In a sixth aspect of the eighth embodiment, the human is infected with HCV genotype 1, 2, 3, 4, 5, or 6, or any combination thereof. In one subembodiment, the subject is infected with HCV genotype 1, 2, or 3, or any combination thereof.

In a seventh aspect of the eighth embodiment, the human has an undetectable amount of HCV RNA for at least 24 weeks after the end of the time period. In one subembodiment, the human has an undetectable amount of HCV RNA for at least 36 weeks after the end of the time period. In another subembodiment, the human has an undetectable amount of HCV RNA for at least 48 weeks after the end of the time period.

In an eighth aspect of the eighth embodiment, an effective amount of GS-7977 and an effective amount of ribavirin are administered to the human according to an interferon-free treatment regimen. In one subembodiment, the interferon-free treatment regimen consists of administering an effective amount of GS-7977 and an effective amount of ribavirin to the subject for the time period.

In a ninth aspect of the eighth embodiment, the effective amount of GS-7977 comprises a composition comprising GS-7977 and at least one pharmaceutically acceptable excipient as disclosed herein.

In a tenth aspect of the eighth embodiment, the effective amount of GS-7977 comprises a unit dosage form comprising GS-7977 and at least one pharmaceutically acceptable excipient as disclosed herein.

A ninth embodiment is directed to a method of treating a human infected with hepatitis C virus, said method comprising administering to the human for a time period an effective amount of GS-7977 and an effective amount of ribavirin sufficient to produce an amount of HCV RNA in the human that is less than about 15 IU/mL for at least 12 weeks after the end of the time period.

In a first aspect of the ninth embodiment, the time period is selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is about 12 weeks. In another subembodiment the time period is about 8 weeks.

In a second aspect of the ninth embodiment, the effective amount of GS-7977 is a daily dose selected from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg. In one subembodiment, the daily dose of GS-7977 is administered to the human QD, BID, TID, or QID. In another subembodiment, a daily dose of about 400 mg of GS-7977 is administered to the human QD, BID, TID, or QID. In another subembodiment, a daily dose of about 400 mg of GS-7977 is administered to the human QD.

In a third aspect of the ninth embodiment, an effective amount of GS-7977 is administered to the human in combination with an effective amount of ribavirin wherein the administration is concurrent or alternative.

In a fourth aspect of the ninth embodiment, the effective amount of ribavirin is a daily dose selected from about 600 mg to about 1400 mg, and from about 800 mg to about 1200 mg. In one subembodiment, the effective amount of ribavirin is a daily dose of about 1000 mg to about 1200 mg. In another subembodiment, the effective amount of ribavirin is a daily dose of about 1000 mg to about 1200 mg based on the human's body weight. In another subembodiment, the effective amount of ribavirin is a daily dose of about 800 mg. In another subembodiment, the daily dose of ribavirin is administered to the human QD, BID, TID, or QID. In a further subembodiment, the daily dose of ribavirin is administered to the human BID.

In a fifth aspect of the ninth embodiment, a daily dose of about 400 mg of GS-7977 is administered to the human in combination with a daily dose of about 800 mg to about 1200 mg of ribavirin. In one subembodiment, a daily dose of about 400 mg of GS-7977 is administered to the human in combination with a daily dose of about 800 mg of ribavirin. In another subembodiment, a daily dose of about 400 mg of GS-7977 is administered to the human in combination with a daily dose of about 1000 mg to about 1200 mg of ribavirin.

In a sixth aspect of the ninth embodiment, the human is infected with HCV genotype 1, 2, 3, 4, 5, or 6, or any combination thereof. In one subembodiment, the human is infected with HCV genotype 1, 2, or 3, or any combination thereof.

In a seventh aspect of the ninth embodiment, the human has an amount of HCV RNA less than about 15 IU/mL for at least 24 weeks after the end of the time period. In one subembodiment, the human has an amount of HCV RNA less than about 15 IU/mL for at least 36 weeks after the end of the time period. In another subembodiment, the human has an amount of HCV RNA less than about 15 IU/mL for at least 48 weeks after the end of the time period.

In an eighth aspect of the ninth embodiment, an effective amount of GS-7977 and an effective amount of ribavirin are administered to the human according to an interferon-free treatment regimen. In one subembodiment, the interferon-free treatment regiment consists of administering an effective amount of GS-7977 and an effective amount of ribavirin to the subject for the time period.

In a ninth aspect of the ninth embodiment, the effective amount of GS-7977 comprises a composition comprising GS-7977 and at least one pharmaceutically acceptable excipient as disclosed herein.

In a tenth aspect of the ninth embodiment, the effective amount of GS-7977 comprises a unit dosage form comprising GS-7977 and at least one pharmaceutically acceptable excipient as disclosed herein.

A tenth embodiment is directed to a method of treating a human infected with hepatitis C virus, said method consisting of administering to the human for a time period about 400 mg of GS-7977 and about 800 mg to about 1200 mg of ribavirin.

In a first aspect of the tenth embodiment, the time period is selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is 12 weeks. In another subembodiment the time period is 8 weeks.

In a second aspect of the tenth embodiment, about 400 mg of GS-7977 is administered to the human daily. In one subembodiment, a daily dose of about 400 mg of GS-7977 is administered to the human QD, BID, TID, or QID. In another subembodiment, a daily dose of about 400 mg of GS-7977 is administered to the human QD.

In a third aspect of the tenth embodiment, about 400 mg of GS-7977 is administered to the human in combination with about 800 mg to about 1200 mg of ribavirin, wherein the administration is concurrent or alternative.

In a fourth aspect of the tenth embodiment, about 1000 mg to about 1200 mg of ribavirin is administered to the human daily. In one subembodiment, a daily dose of 1000 mg to about 1200 mg of ribavirin is administered to the human QD, BID, TID, or QID. In another subembodiment, a daily dose of about 1000 mg to about 1200 mg of ribavirin is administered to the human BID. In a further subembodiment, a daily dose of 1000 mg or 1200 mg of ribavirin is administered to the subject based on body weight.

In a fifth aspect of the tenth embodiment, about 800 mg of ribavirin is administered to the human daily. In one subembodiment, a daily dose of about 800 mg of ribavirin is administered to the human QD, BID, TD or QID. In another subembodiment, a daily dose of about 800 mg of ribavirin is administered to the human BID.

In a sixth aspect of the tenth embodiment, the human is infected with HCV genotype 1, 2, 3, 4, 5 or 6, or any combination thereof. In one subembodiment, the human is infected with HCV genotype 1, 2, or 3, or any combination thereof.

In a seventh aspect of the tenth embodiment, the human has an undetectable amount of HCV RNA for at least 12 weeks after the end of the time period. In one subembodiment, the human has an undetectable amount of HCV RNA for at least 24 weeks after the end of the time period. In another subembodiment, the human has an undetectable amount of HCV RNA for at least 36 weeks after the end of the time period. In a further subembodiment, the human has an undetectable amount of HCV RNA for at least 48 weeks after the end of the time period.

In an eighth aspect of the tenth embodiment, the about 400 mg of GS-7977 comprises a composition comprising GS-7977 and at least one pharmaceutically acceptable excipient as disclosed herein.

In a ninth aspect of the tenth embodiment, the about 400 mg of GS-7977 comprises a unit dosage form comprising GS-7977 and at least one pharmaceutically acceptable excipient as disclosed herein.

An eleventh embodiment is directed to a composition useful for the treatment of hepatitis C virus infection in a subject, said composition comprising an effective amount of GS-7977 and an effective amount of ribavirin.

In a first aspect of the eleventh embodiment, the composition does not comprise peginterferon.

In a second aspect of the eleventh embodiment, the effective amount of GS-7977 comprises from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg of GS-7977 administered to the subject daily. In one subembodiment, the composition comprises about 400 mg of GS-7977 administered to the subject QD.

In a third aspect of the eleventh embodiment, the effective amount of ribavirin comprises from about 600 mg to about 1400 mg, or from about 800 mg to about 1200 mg administered to the subject daily. In one subembodiment, the effective amount of ribavirin is about 1000 mg to about 1200 mg administered to the subject daily. In another subembodiment, the effective amount of ribavirin is about 1000 mg to about 1200 mg administered to the subject daily based on the subject's body weight. In another subembodiment, the effective amount of ribavirin about 800 mg administered to the subject daily. In another subembodiment, the composition comprises an effective amount ribavirin administered to the subject QD, BID, TID, or QID. In a further subembodiment, the composition comprises an effective amount of ribavirin administered to the subject BID.

In a fourth aspect of the eleventh embodiment, the composition comprises about 400 mg of GS-7977 administered to the subject QD and about 800 mg to about 1200 mg of ribavirin administered to the subject BID. In one subembodiment, the composition comprises about 400 mg of GS-7977 administered to the subject QD and about 800 mg of ribavirin administered to the subject BID. In another subembodiment, the composition comprises about 400 mg of GS-7977 administered to the subject QD and about 100 mg to about 1200 mg of ribavirin administered to the subject BID In a fifth aspect of the eleventh embodiment, the composition is capable of providing an undetectable amount of HCV RNA for at least 12 weeks after the end of a time period following treatment of a subject infected with hepatitis C virus for the time period. In one subembodiment, the composition is capable of providing an undetectable amount of HCV RNA for at least 24 weeks after the end of a time period following treatment of a subject infected with hepatitis C virus for the time period. In another subembodiment, the composition is capable of providing an undetectable amount of HCV RNA for at least 36 weeks after the end of a time period following treatment of a subject infected with hepatitis C virus for the time period. In a further subembodiment, the composition is capable of providing an undetectable amount of HCV RNA for at least 48 weeks after the end of a time period following treatment of a subject infected with hepatitis C virus for the time period.

In a sixth aspect of the eleventh embodiment, the composition is capable of providing less than about 15 IU/mL of HCV RNA for at least 12 weeks after the end of a time period following treatment of a subject infected with hepatitis C virus for the time period. In one subembodiment, the composition is capable of providing less than about 15 IU/mL of HCV RNA for at least 24 weeks after the end of a time period following treatment of a subject infected with hepatitis C virus for the time period. In another subembodiment, the composition is capable of providing less than about 15 IU/mL of HCV RNA for at least 36 weeks after the end of a time period following treatment of a subject infected with hepatitis C virus for the time period. In a further subembodiment, the composition is capable of providing less than about 15 IU/mL of HCV RNA for at least 48 weeks after the end of a time period following treatment of a subject infected with hepatitis C virus for the time period.

In a seventh aspect of the eleventh embodiment, the effective amount of GS-7977 comprises a unit dosage form comprising GS-7977 and at least one pharmaceutically acceptable excipient as disclosed herein administered to the subject. In one subembodiment, the unit dosage form comprising GS-7977 and at least one pharmaceutically acceptable excipient as disclosed herein is administered to the subject QD.

A twelfth embodiment is directed to use of an effective amount of GS-7977 and an effective amount of ribavirin to treat hepatitis C virus infection in a subject in need thereof.

In a first aspect of the twelfth embodiment, the use comprises administering an effective amount of GS-7977 and an effective amount of ribavirin to the subject for a time period selected from among from about 2 weeks to about 12 weeks, from about 3 weeks to about 12 weeks, from about 4 weeks to about 12 weeks, from about 5 weeks to about 12 weeks, from about 6 weeks to about 12 weeks, from about 7 weeks to about 12 weeks, from about 8 weeks to about 12 weeks, from about 9 weeks to about 12 weeks, from about 10 weeks to about 12 weeks, from about 11 weeks to about 12 weeks, and about 12 weeks. In one subembodiment the time period is 12 weeks. In another subembodiment the time period is 8 weeks.

In a second aspect of the twelfth embodiment, the effective amount of GS-7977 is a daily dose selected from about 100 mg to about 800 mg, from about 200 mg to about 800 mg, from about 400 mg to about 800 mg, from about 600 mg to about 800 mg, from about 100 mg to about 600 mg, from about 100 mg to about 400 mg, from about 100 mg to about 200 mg, from about 200 mg to about 600 mg, from about 200 mg to about 400 mg, from about 400 mg to about 600 mg, and about 400 mg. In one subembodiment, the daily dose of GS-7977 is administered to the subject QD, BID, TID, or QID. In another subembodiment, a daily dose of about 400 mg of GS-7977 is administered to the subject QD, BID, TID, or QID. In another subembodiment, a daily dose of about 400 mg of GS-7977 is administered to the subject QD.

In a third aspect of the twelfth embodiment, an effective amount of GS-7977 is used in combination with an effective amount of ribavirin, wherein the administration of GS-7977 and ribavirin is concurrent or alternative.

In a fourth aspect of the twelfth embodiment, the effective amount of ribavirin is a daily dose selected from about 600 mg to about 1400 mg, and from about 800 mg to about 1200 mg. In one subembodiment, the effective amount of ribavirin is a daily dose of about 1000 mg to about 1200 mg. In another subembodiment, the effective amount of ribavirin is a daily dose of about 1000 mg to about 1200 mg based on the subject's body weight. In another subembodiment, the effective amount of ribavirin is a daily dose of about 800 mg. In another subembodiment, the daily dose of ribavirin is administered to the subject QD, BID, TID, or QID. In a further subembodiment, the daily dose of ribavirin is administered to the subject BID.

In a fifth aspect of the twelfth embodiment, the effective amount of GS-7977 is about 400 mg QD and the effective amount of ribavirin is about 800 mg to about 1200 mg BID. In one subembodiment, the effective amount of GS-7977 is about 400 mg QD and the effective amount of ribavirin is about 800 mg BID. In another subembodiment, the effective amount of GS-7977 is about 400 mg QD and the effective amount of ribavirin is about 1000 mg to about 1200 mg BID.

In a sixth aspect of the twelfth embodiment, the subject is infected with HCV genotype 1, 2, 3, 4, 5 or 6, or any combination thereof. In one subembodiment, the subject is infected with HCV genotype 1, 2, or 3, or any combination thereof.

In a seventh aspect of the twelfth embodiment, the subject has an undetectable amount of HCV RNA for at least 12 weeks after the end of the time period. In one subembodiment, the subject has an undetectable amount of HCV RNA for at least 24 weeks after the end of the time period. In another subembodiment, the subject has an undetectable amount of HCV RNA for at least 36 weeks after the end of the time period. In a further subembodiment, the subject has an undetectable amount of HCV RNA for at least 48 weeks after the end of the time period.

In an eighth aspect of the twelfth embodiment, the subject has an amount of HCV RNA less than about 15 IU/mL for at least 12 weeks after the end of the time period. In on subembodiment, the subject has an amount of HCV RNA less than about 15 IU/mL for at least 24 weeks after the end of the time period. In one subembodiment, the subject has an amount of HCV RNA less than about 15 IU/mL for at least 36 weeks after the end of the time period. In another subembodiment, the subject has an amount of HCV RNA less than about 15 IU/mL for at least 48 weeks after the end of the time period.

In a ninth aspect of the twelfth embodiment, the subject is a human.

In a tenth aspect of the twelfth embodiment, an effective amount of GS-7977 and an effective amount of ribavirin are used according to an interferon-free treatment regimen. In one subembodiment, the interferon-free treatment regimen consists of administering an effective amount of GS-7977 and an effective amount of ribavirin to the subject for a time period.

In an eleventh aspect of the twelfth embodiment, the effective amount of GS-7977 comprises a composition comprising GS-7977 and at least one pharmaceutically acceptable excipient as disclosed herein.

In a twelfth aspect of the twelfth embodiment, the effective amount of GS-7977 comprises a unit dosage form comprising GS-7977 and at least one pharmaceutically acceptable excipient as disclosed herein.

According to the FDA-approved label dated Aug. 22, 2011, which is hereby incorporated by reference, the recommended dose of COPEGUS® (ribavirin) tablets when used in combination with peginterferon depends on body weight and the HCV genotype to be treated, as shown in the following table.

| HCV Genotype | PEGASYS ® Dose* | COPEGUS ® Dose | Duration |
|---|---|---|---|
| Genotypes 1, 4 | 180 μg | <75 kg = 1000 mg | 48 weeks |
| | | ≥75 kg = 1200 mg | 48 weeks |
| Genotypes 2, 3 | 180 μg | 800 mg | 24 weeks |

Genotypes 2 and 3 showed no increased response to treatment beyond 24 weeks.
*See PEGASYS ® Package Insert for further details on PEGASYS ® dosing and administration. The FDA- approved label for PEGASYS ® dated Sep. 29, 2011 is incorporated by reference.

The daily dose of COPEGUS® indicated for use in combination with peginterferon is 800 mg to 1200 mg administered orally in two divided doses (BID). The dose should be individualized to the subject depending on baseline disease characteristics (e.g., genotype), response to therapy, and tolerability of the regimen. Based on the foregoing, as well as the examples described below, an effective amount ribavirin when used in combination with an effective amount of GS-7977 is contemplated to include 800 mg and 1000 mg to 1200 mg, including daily doses of 1000 mg or 1200 mg depending on body weight.

Based on the data reported herein, an effective amount of GS-7977 is 400 mg QD, which can also be administered BID, TID, or QID. It is also contemplated that an effective amount of GS-7977 can include 100 mg to 400 mg and all integer values in between.

When administered as a combination, GS-7977 is administered to the subject in association with ribavirin. That is, the GS-7977 dose is administered during the same time period that the subject receives doses of ribavirin. Concurrent or alternative administration is considered, which means that while the GS-7977 and ribavirin are administered during the same time period, the specific order of administration on a daily basis can be: GS-7977 followed by ribavirin, GS-7977 and ribavirin together, or ribavirin followed by GS-7977. GS-7977 may be administered orally in capsule or tablet form, or any other suitable unit dosage form, in association with the oral (capsule or tablet form) administration of ribavirin. Of course, other types of administration of both medicaments, as they become available, are contemplated, such as by nasal spray, by a buccal or sublingual administration dosage form, transdermally, by suppository, by sustained release dosage form, etc. Any form of administration will work so long as the proper dosages are delivered without destroying the active ingredient and/or without impeding the effective amount of GS-7977 and/or an effective amount of ribavirin delivered to the subject.

EXAMPLES

GS-7977 Formulation Compositions Using Roller Compaction Process

A series of formulations containing polymorphic Form 1 GS-7977 with different quantitative compositions of excipients were prepared and screened using the roller compaction process to evaluate the impact of various diluents and compression aids on granulation powder properties and on tablet disintegration and dissolution times. Considerations were also given to moisture sorption properties of the tablets due to the sensitivity of Form 1 of GS-7977 to moisture.

All formulations were compressed into tablets at both high and low hardness levels. Formulation and tablet performance were determined by tablet disintegration time, content uniformity, and dissolution, as presented in Table 1A.

TABLE 1A

Formulation Compositions for GS-7977 Form 1 Tablets Using a Roller Compaction Process

| | Formulation Composition (% w/w) | | | | | | |
|---|---|---|---|---|---|---|---|
| Ingredient | A | B1 | B2 | C | G1 | G2 | H |
| | Intragranular | | | | | | |
| GS-7977 | 25.0 | 33.3 | 33.3 | 33.3 | 33.3 | 33.3 | 33.3 |
| Microcrystalline Cellulose | 25.0 | 33.3 | 33.3 | — | — | — | — |
| Mannitol | — | — | — | 33.3 | 30.6 | 33.3 | 30.6 |
| Croscarmellose Sodium | — | — | — | — | 2.00 | 3.0 | 2.00 |
| Colloidal Silicon Dioxide | 0.5 | 0.25 | 0.3 | 0.25 | 0.25 | 0.3 | 0.25 |
| Magnesium Stearate | — | 0.5 | 0.5 | 0.5 | 0.5 | 0.5 | 0.5 |
| | Extragranular | | | | | | |
| Microcrystalline Cellulose | 49.0 | 31.9 | 31.8 | — | 15.3 | 21.0 | — |
| Mannitol | — | — | — | 31.9 | 15.3 | 5.8 | — |

TABLE 1A-continued

Formulation Compositions for GS-7977 Form 1 Tablets Using a Roller Compaction Process

| | Formulation Composition (% w/w) | | | | | | | | | | | |
|---|---|---|---|---|---|---|---|---|---|---|---|---|
| Ingredient | A | | B1 | | B2 | C | G1 | | G2 | | H | |
| Croscarmellose Sodium | — | | — | | — | — | 2.0 | | 2.0 | | 2.00 | |
| Dicalcium Phosphate | — | | — | | — | — | — | | — | | 30.6 | |
| Colloidal Silicon Dioxide | — | | 0.25 | | 0.25 | 0.25 | 0.25 | | 0.3 | | 0.25 | |
| Magnesium Stearate | 0.5 | | 0.5 | | 0.5 | 0.5 | 0.5 | | 0.5 | | 0.5 | |
| Total Tablet Weight (mg) | 400 | | 300 | | 300 | 300 | 300 | | 300 | | 300 | |
| Hardness (kp) Low/High | 8.1 | 16.3 | 7.4 | 17.2 | 10.2 | 5.8 NA | 5.4 | 12.1 | 8.2 | 5.1 | 9.9 | |
| Disintegration time (min:sec) | 0:17 | 0:33 | 0:13 | 3:16 | 0:48 | 45:00 | 0:14 | 6:27 | 1:43 | 1:23 | 8:06 | |
| Dissolution @ 45 min (% LS) | 98 | 102 | 94 | 91 | 82 | 87 NA | 101 | 95 | 96 | 60 | 64 | |

The results in Table 1A show that use of microcrystalline cellulose as the sole diluent (Formulations A, B1, B2) produced tablets with acceptable hardness, disintegration and dissolution, even without incorporating a disintegrant. In contrast, incorporation of mannitol as the sole diluent (Formulation C) without a disintegrant resulted in lower compressibility and a longer disintegration time resulting in slower dissolution. When used in combination with microcrystalline cellulose, mannitol levels as high as 75% of total filler amount (Formulation G) produced an acceptable tablet as long as a disintegrant was added to the formulation. However, lowering mannitol levels produced a harder and more robust tablet. Dicalcium phosphate used in combination with mannitol (Formulation H) failed to produce an acceptable tablet with respect to dissolution and hardness. The data in Table 1A support the use of formulations containing microcrystalline cellulose and mannitol/microcrystalline cellulose, in particular, as diluents.

Formulations B2 and G2 in Table 1A prepared per a roller compaction/granulation process were further evaluated. The prototype tablet batches were packaged 30 tablets per bottle and placed on stability in 40° C./75% RH conditions, with each bottle containing a molecular sieve (Tri-Sorb®) desiccant. The data shown in Table 1B show a decrease in moisture level as the amount of mannitol is increased (concomitant with reduction in microcrystalline cellulose).

TABLE 1B

Stability Data for GS-7977 Form 1 Tablets Using a Roller Compaction Process

| | | | | HPLC Assay | | Dissolution (% Dissolved)[a] | | | | |
|---|---|---|---|---|---|---|---|---|---|---|
| Formulation | Stability Condition | Time (mo.) | % LS | Unknown % img/deg at RRT 0.67 | | 15 min | 30 min | 45 min | 60 min | Water Content (%) |
| B2 | 25° C./60% RH | 0 | 98.5 | — | | 76 (4) | 80 (3) | 82 (3) | 85 (3) | 4.3 |
| | | 3 | 98.4 | — | | 73 (2) | 77 (3) | 79 (3) | 81 (3) | 3.2 |
| | | 6 | 96.2 | <0.04 | | 76 (2) | 80 (2) | 82 (2) | 85 (2) | 3.2 |
| | 40° C./75% RH | 3 | 97.0 | — | | 71 (5) | 74 (5) | 77 (4) | 79 (4) | 3.3 |
| | | 6 | 96.8 | 0.04 | | 79 (8) | 84 (8) | 87 (8) | 89 (7) | 3.5 |
| G2 | 25° C./60% RH | 0 | 99.9 | — | | 84 (6) | 93 (3) | 96 (3) | 98 (3) | 1.7 |
| | | 3 | 98.3 | <0.04 | | 72 (8) | 92 (2) | 96 (2) | 97 (3) | 1.4 |
| | | 6 | 97.9 | <0.04 | | 82 (4) | 93 (2) | 95 (3) | 97 (2) | 1.3 |
| | 40° C./75% RH | 3 | 98.0 | <0.04 | | 77 (4) | 84 (4) | 88 (3) | 89 (3) | 1.5 |
| | | 6 | 99.0 | <0.04 | | 80 (5) | 90 (5) | 93 (4) | 94 (4) | 1.2 |
| | 40° C./75% RH (no dessicant) | 3 | 97.9 | 0.08 | | 79 (4) | 91 (3) | 96 (2) | 97 (2) | 1.9 |
| | | 6 | 97.8 | 0.18 | | 72 (8) | 85 (2) | 91 (2) | 93 (3) | 1.9 |

[a]Dissolution method: USP Apparatus II (paddles) with 900 mL, pH 6.8 (50 mM sodium phosphate), 0.5% SLS, 75 rpm, 37° C.

GS-7977 400 mg Tablets

Formulations (Tablets A and B) comprising GS-7977 polymorphic Form 1 were prepared by dry granulation. The formulations contained GS-7977 (polymorphic Form 1) (33.33%), mannitol (30.00%), microcrystalline cellulose (29.67%), croscarmellose sodium (5.00%), colloidal silicon dioxide (0.50%), and magnesium stearate (1.50%), as described in Table 2.

TABLE 2

GS-7977 Polymorphic Form 1 400 mg Tablet Compositions

| | % w/w of 400 mg tablet | |
|---|---|---|
| | Tablet A | Tablet B |
| Intragranular Components | | |
| GS-7977 (Form 1) | 33.33 | 33.33 |
| Mannitol | 30.0 | 30.0 |
| Croscarmellose Sodium | 3.0 | 3.0 |
| FD&C Red 40 Aluminum Lake | — | 0.27 |
| FD&C Blue 2 Aluminum Lake | — | 0.10 |
| Colloidal Silicon Dioxide | 0.25 | 0.25 |
| Magnesium Stearate | 0.50 | 0.5 |
| Extragranular Components | | |
| Microcrystalline Cellulose | 29.67 | 29.12 |
| Croscarmellose Sodium | 2.00 | 2.00 |
| FD&C Red 40 Aluminum Lake | — | 0.13 |
| FD&C Blue 2 Aluminum Lake | — | 0.05 |
| Colloidal Silicon Dioxide | 0.25 | 0.25 |
| Magnesium Stearate | 1.00 | 1.00 |
| Total | 100.00 | 100.00 |
| Coating Agent | 3.00 | — |

Tablets containing about 400 mg of GS-7977 (Form 1) per tablet and an Opadry II purple film coating (Tablet A in Table 2) were prepared as follows:

(1) A composition comprising GS-7977 (Form 1) and the intragranular excipients (mannitol, croscarmellose sodium, and colloidal silicon dioxide) was sifted through a 20-mesh screen and added to a blender (V-shell blender) and blended for about 10-15 minutes to obtain an initial blend. Separately, the intragranular magnesium stearate was passed through a 20-mesh screen and mixed with a portion of the initial blend, added to the blender, and blended for about 5 minutes to obtain an intragranular blend.

(2) Separately, the extragranular excipients microcrystalline cellulose, croscarmellose sodium, and colloidal silicon dioxide were sifted through a 20-mesh screen for use in the final blending (step (4), below).

(3) The intragranular blend comprising GS-7977, mannitol, croscarmellose sodium, colloidal silicon dioxide, and magnesium stearate was passed through a roller compactor equipped with a 20-mesh (0.84 mm) milling screen on the granulator and both 20- and 60-mesh (0.25 mm) screens on the separator until granulation was achieved. The roller compactor parameters were: (i) granulator speed ranges from about 50 to about 90 rpm, more specifically about 70 rpm, compactor speed ranges from about 4 to about 6 rpm, more specifically about 5 rpm, and pressure ranges from about 65 to about 100 barr, more specifically about 75 to about 100 bar. Ribbons were produced using flat straight-grooved rollers. Upon passing through the roller compactor, the material was passed/forced through a 20-mesh screen and then sifted with a 60 mesh screen. Granules were sorted into three categories (coarse, acceptable, and fine) using the separator portion of the dry granulator. 'Coarse' granules retained on the 20-mesh (0.84 mm) screen on the separator were passed through a Comil with a 0.055-inch (1.4 mm) round screen. Granules that remained on the 60 mesh screen were considered to be 'acceptable' granules. The milled/sifted granule material was passed to the final blending step. Material that passed through the 60 mesh screen was considered 'fine' and was re-circulated through the roller compactor. This process was repeated until a minimum amount (e.g., less than 20%) of fines remained.

(4) The milled/sifted granules from step (3) and the sifted extragranular excipients (microcrystalline cellulose, mannitol, croscarmellose sodium and silicon dioxide) from step (2) were added to a blender (V-shell blender) and blended for about 15 minutes. Separately, magnesium stearate was passed through a 20-mesh screen. The magnesium stearate was added to the blender and blended for about 5 minutes to obtain a final powder blend comprising 33.33% w/w GS-7977. Blend uniformity samples were taken prior to removing the blend from the blender.

(5) The final blend was compressed into tablets using a tablet press (e.g., a Globe Pharma Mini Press) to obtain 1200 mg uncoated tablets comprising about 400 mg of GS-7977. As needed, a 15% w/w aqueous suspension for film-coating comprising polyvinyl alcohol (Opadry II Purple) was prepared and applied to achieve a target weight gain of 3% (range: 2-4%). The coating suspension was sprayed at 300 g/min/4 guns (range: 200-400 g/min/4 guns) at a target pan speed of 5 rpm (range: 4-8 rpm) and an exhaust temperature of 46±5° C. The GS-7977 tablets were packaged with 30 tablets and 1 gram of desiccant per bottle.

Uncoated tablets comprising 400 mg of GS-7977 (Form 1) were prepared in a similar manner using blue and red lake in the blend (Tablet B in Table 2).

Another formulation (Tablet C) was prepared containing GS-7977 polymorphic Form 6 (33.33%), mannitol (30.00%), microcrystalline cellulose (29.67%), croscarmellose sodium (5.00%), colloidal silicon dioxide (0.50%), and magnesium stearate (1.50%), as described in Table 3. While a low moisture grade of microcrystalline cellulose (PH 112) was used in the Form 1 formulation to improve the stability of Form 1 GS-7977, the microcrystalline cellulose grade was changed to PH 102 for the Tablet C formulation due to the non-hygroscopic nature of Form 6. In addition, incorporation of a large proportion of the excipients into the intragranular composition decreased the potential for powder segregation and the variability in the blend, and improved the tablet content uniformity for the Tablet C formulation.

TABLE 3

GS-7977 Polymorphic Form 6 400 mg Tablet Composition

| | Tablet C | |
|---|---|---|
| | % w/w | mg/tablet |
| Intragranular Components | | |
| GS-7977 (Form 6) | 33.33 | 400.0 |
| Mannitol | 30.00 | 360.0 |
| Microcrystalline Cellulose | 24.67 | 296.0 |
| Croscarmellose Sodium | 2.50 | 30.0 |
| Colloidal Silicon Dioxide | 0.45 | 5.4 |
| Magnesium Stearate | 0.75 | 9.0 |
| Extragranular Components | | |
| Microcrystalline Cellulose | 5.00 | 60.0 |
| Croscarmellose Sodium | 2.50 | 30.0 |

TABLE 3-continued

GS-7977 Polymorphic Form 6 400 mg Tablet Composition

|  | Tablet C | |
| --- | --- | --- |
|  | % w/w | mg/tablet |
| Colloidal Silicon Dioxide | 0.05 | 0.6 |
| Magnesium Stearate | 0.75 | 9.0 |
| Total | 100.00 | 1200 |
| Coating Agent | 3.0 | 36.0 |

The Tablet C formulation was prepared by blending the intragranular components listed in Table 3, other than magnesium stearate (i.e., GS-7977, microcrystalline cellulose, mannitol, croscarmellose sodium and colloidal silicon dioxide) in a blender. The mixture was milled, blended with the intragranular magnesium stearate and dry granulated using a roller compaction process train and mill. The resulting ribbons were milled through a milling screen and then blended with the extragranular excipients (microcrystalline cellulose, croscarmellose sodium, colloidal silicon dioxade, magnesium stearate) to yield a powder blend comprising 33.33% w/w GS-7977. The powder blend was compressed to a target tablet weight of 1200 mg, with each tablet comprising about 400 mg of GS-7977. An aqueous suspension for the film-coating process was prepared and applied to achieve a target weight gain of 3%.

Moisture content was tested for Tablets A-C and tablet stability (30 tablets/bottle with a 1 gram Tri-sorb® dessicant in a 60 cc HDPE bottle) was tested for Tablets B and C, the results of which are presented in Table 4.

TABLE 4

Moisture and Stability Data for GS-7977 400 mg Tablets

|  | Tablet A | | | Tablet B | | | Tablet C |
| --- | --- | --- | --- | --- | --- | --- | --- |
|  |  | HPLC Assay | | | HPLC Assay | | HPLC Assay |
|  | Moisture (% w/w) | % GS-7977 | % Impurity | Moisture (% w/w) | % GS-7977 | % Impurity | % GS-7977 |
| Initial | 1.8 | 100 | 0.05 | 1.5 | 99.5 | 0.05 | 101.7 |
| 40° C./75% RH | | | | | | | |
| 1 month | 1.4 | 102.4 | 0.04 | 1.5 | 101.7 | 0.05 | 101.1 |
| 2 months | 1.5 | 101.5 | 0.04 | 1.7 | 101.1 | 0.04 | 100.9 |

The results in Table 4 show that the exemplary tablet compositions described herein exhibit stability to both moisture and degradation.

The dissolution profile (75 RPM, Apparatus II (Paddle), Phosphate buffer pH 6.8 900 mL) of tablets having the Tablet B formulation was tested initially and after storage at 40° C. and 75% relative humidity. The results are presented in Table 5.

TABLE 5

Dissolution Data for GS-7977 (Form 1) 400 mg Tablet B Composition

|  | Mean Dissolution (±RSD$^a$) | | | |
| --- | --- | --- | --- | --- |
|  | 15 min | 30 min | 45 min | 60 min |
| Initial | 97 ± 1 | 102 ± 2 | 103 ± 1 | 102 ± 1 |
| 40° C./75% RH | | | | |

TABLE 5-continued

Dissolution Data for GS-7977 (Form 1) 400 mg Tablet B Composition

|  | Mean Dissolution (±RSD$^a$) | | | |
| --- | --- | --- | --- | --- |
|  | 15 min | 30 min | 45 min | 60 min |
| 1 month | 87 ± 3 | 99 ± 2 | 101 ± 2 | 100 ± 3 |
| 2 month | 96 ± 1 | 102 ± 1 | 102 ± 1 | 102 ± 1 |

$^a$RSD = Relative Standard Deviation

In Vitro Antiviral Synergy for the Combination of GS-977 and Ribavirin

The antiviral effect of GS-7977 in combination with ribavirin was evaluated using the HCV genotype 1a replicon. (Robinson et al., Antimicrob. Agents Chemother. (2010) 54(8): 3099-3106.) The cells were grown in cell culture medium containing Dulbecco's Modified Eagle Medium (DMEM) with Gibco® GlutaMAX supplemented with 10% HyClone FBS, 100 units/mL penicillin, 100 µg/mL streptomycin, and 0.1 mM non-essential amino acids. Replicon cells were maintained in 0.5 mg/mL Geneticin®. The cells were passaged every 3-4 days before reaching confluency. All compounds were supplied in 100% DMSO and compound serial dilutions were performed in 100% DMSO. To each well of a 384-well plate was added 90 µL of cell culture medium (without Geneticin®) containing 2000 suspended HCV replicon cells and 0.4 µL of compound solution. The DMSO concentration of the final assay wells was 0.44%. The plates were incubated for 3 days at 37° C. with 5% $CO_2$ and 85% humidity.

For the $CC_{50}$ assay, the media in the 384-well plate was aspirated and the wells were washed four times with 100 µL 1×PBS each. A volume of 50 µL of a solution containing 400 nM calcein AM in 1×PBS was added to each well and the plate was incubated for 30 minutes at room temperature before the fluorescence signal (excitation 490 nm, emission 520 nm) was measured.

$EC_{50}$ assays were performed in the same wells as $CC_{50}$ assays. The calcein-PBS solution was aspirated and a volume of 20 µL of Dual-Glo® luciferase buffer was added to each well. The plate was incubated for 10 minutes at room temperature and a volume of 20 µL of a solution containing a 1:100 mixture of Dual-Glo® Stop & Glo® substrate and Dual-Glo® Stop & Glo® buffer was added to each well. The plate was incubated at room temperature for 10 minutes before the luminescence signal was measured.

The combination study experimental data were analyzed for two-compound synergy using the MacSynergy II program developed by Prichard and Shipman. (Prichard et al., MacSyngergy™ II, Version 1.0, University of Michigan, Ann Arbor (1993).) Two-compound synergy definitions are provided in Table 6:

TABLE 6

Two-Compound Synergy Definitions

| Synergy/Antagonism Volume (nM$^2$%) | Interaction |
|---|---|
| >100 | Strong Synergy |
| >50 and ≤100 | Moderate Synergy |
| >25 and ≤50 | Minor Synergy |
| ≤25 and >−25 | Additive |
| ≤−25 and >−50 | Minor Antagonism |
| ≤−50 and >−100 | Moderate Antagonsim |
| ≤−100 | Strong Antagonsim |

GS-7977 in combination with ribavirin showed a synergy volume of 35.3±3.2 nM$^2$% indicating a synergistic interaction. A cytotoxicity study analyzing the combined effect of GS-7977 and ribavirin showed cell viability greater than 85% at the highest combined drug concentrations (320 nM GS-7977, 1600 nM ribavirin, 14.0±4.4% inhibition on cell growth). (See also Hebner et al., 63$^{rd}$ Annual Meeting of the American Association for the Study of Liver Diseases, Poster 1875, Nov. 12, 2012.) These findings support the potential of GS-7977 administered in combination with ribavirin to achieve enhanced viral suppression compared to GS-7977 or ribavirin monotherapy.

In Vitro Susceptibility of S282T Mutants to GS-7977, Ribavirin, and the Combination of GS-7977 and Ribavirin In vitro studies have shown that S282T is the primary mutation selected by GS-7977 in HCV genotype 1a, 1b and 2a replicon cells. (Lam et al., J. Virology (2011) 85(23): 12334-12342; Lam et al., Antimicrob. Agents Chemother. (2012) 56(6): 3359-3368.) S282T mutations in NS5B were created by site-directed mutagenesis in 1a-H77, 1b con-1, and 2a JFH1 sub-genomic replicons. 1b con-1-based chimeric replicons containing 2b, 3a, 4a, 5a, or 6a NS5B were also engineered to harbor the S282T mutation. (See Wong et al., Virology (2012) 429:57-62.) Replication capacities and drug susceptibilities of S282T to GS-7977 and ribavirin were determined in transient replicon assays. The susceptibilities of S282T and wild-type (WT) NS5B to GS-7977 and ribavirin were further studied by passaging the mixture of 50% S282T and 50% WT in GT2a in the presence of GS-7977 and ribavirin individually and in combination. Relative percentages of mutant and WT were assessed by deep sequencing.

Figure 2:
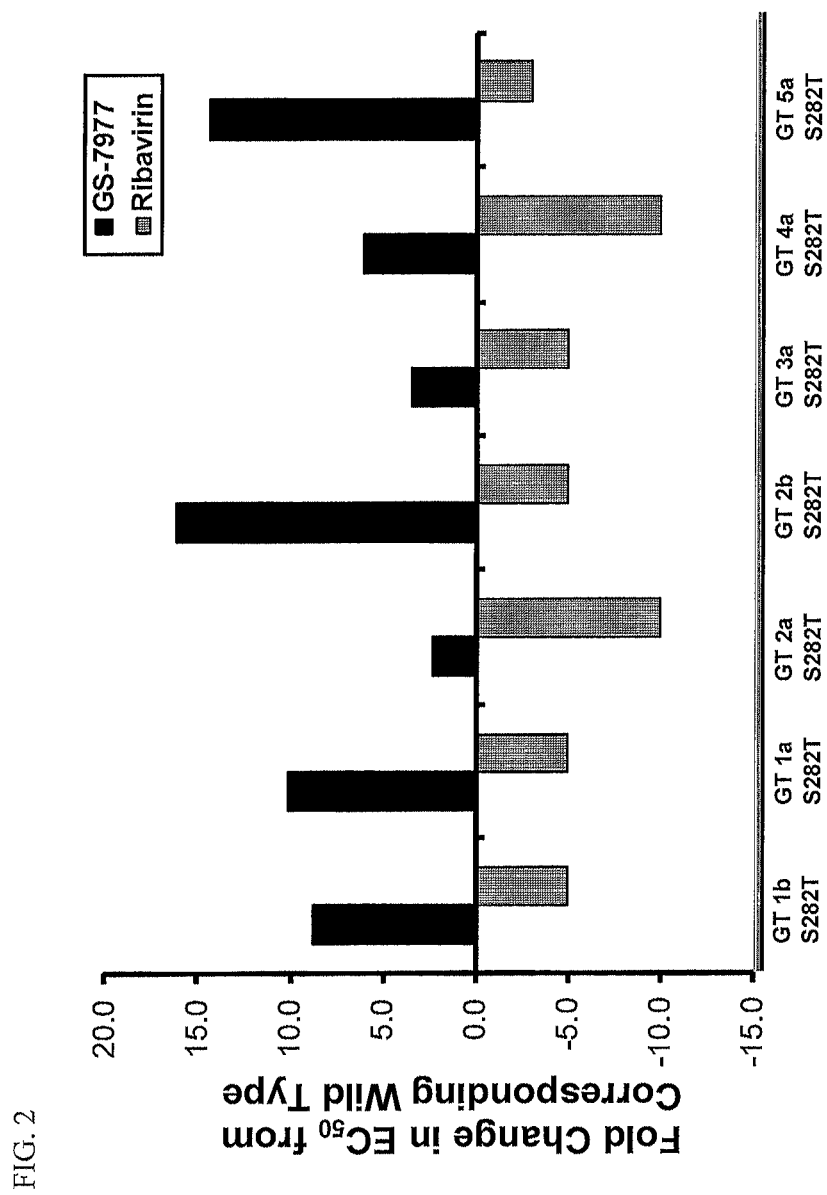
FIG. 2. Fold-change in $EC_{50}$ for HCV replicons containing 1b, 1a, 2a, 2b, 3a, 4a, and 5a NS5B harboring the S282T mutation (compared to the corresponding wild-type) treated with GS-7977 or ribavirin.

Introduction of the NS5B S282T mutation into 1b, 1a, 2a, 2b, 3a, 4a, and 5a HCV replicons resulted in reduced susceptibility to GS-7977 for all seven genotypes, producing a 2- to 16-fold increase in EC$_{50}$ values compared to the wild-type from the corresponding genotypes. Surprisingly, the S282T replicons were 3- to 10-fold more sensitive to treatment with ribavirin than their corresponding wild-type for these seven genotypes. EC$_{50}$ values were not calculated for genotype 6a S282T mutants due to low signal-to-noise ratios; the genotype 6a mutant did not replicate sufficiently to obtain drug susceptibility data. The results of these studies are presented in Table 7, below, and in FIG. 2.

TABLE 7

Antiviral Activity of GS-7977 and Ribavirin Against S282T Mutants in Genotype 1-6 Replicons

| | GS-7977 | | | Ribavirin | | |
|---|---|---|---|---|---|---|
| | EC$_{50}$ nM$^a$ | | Fold | EC$_{50}$ nM$^a$ | | Fold$^b$ |
| Genotype | WT | S282T | Change$^b$ | WT | S282T | Change |
| 1b | 21.5 | 189.2 | 8.8 | 6.6 | 1.6 | 0.2 |
| 1a | 25.1 | 253.1 | 10.1 | 21.0 | 5.0 | 0.2 |
| 2a | 146.8 | 346.1 | 2.4 | 8.3 | 0.6 | 0.1 |
| 2b$^c$ | 13.3 | 215.6 | 16.2 | 2.6 | 0.6 | 0.2 |
| 3a$^c$ | 33.9 | 117.1 | 3.5 | 6.7 | 1.0 | 0.2 |
| 4a$^c$ | 35.8 | 217.5 | 6.1 | 6.2 | 0.6 | 0.1 |
| 5a$^c$ | 9.91 | 142.2 | 14.35 | 1.9 | 0.6 | 0.3 |
| 6a$^c$ | 39.8 | n/a$^d$ | — | 5.3 | n/a$^d$ | — |

$^a$EC$_{50}$ indicates average of 2 or more independent experiments.
$^b$Fold change from corresponding wild-type.
$^c$These chimeric replicons carry NS5B from genotypes 2b, 3a, 4a; however, the NS5A sequence in all of these chimeric replicons is derived from genotype 1b.
$^d$EC$_{50}$ was not determined due to low signal-to-noise ratio.

Figure 3:
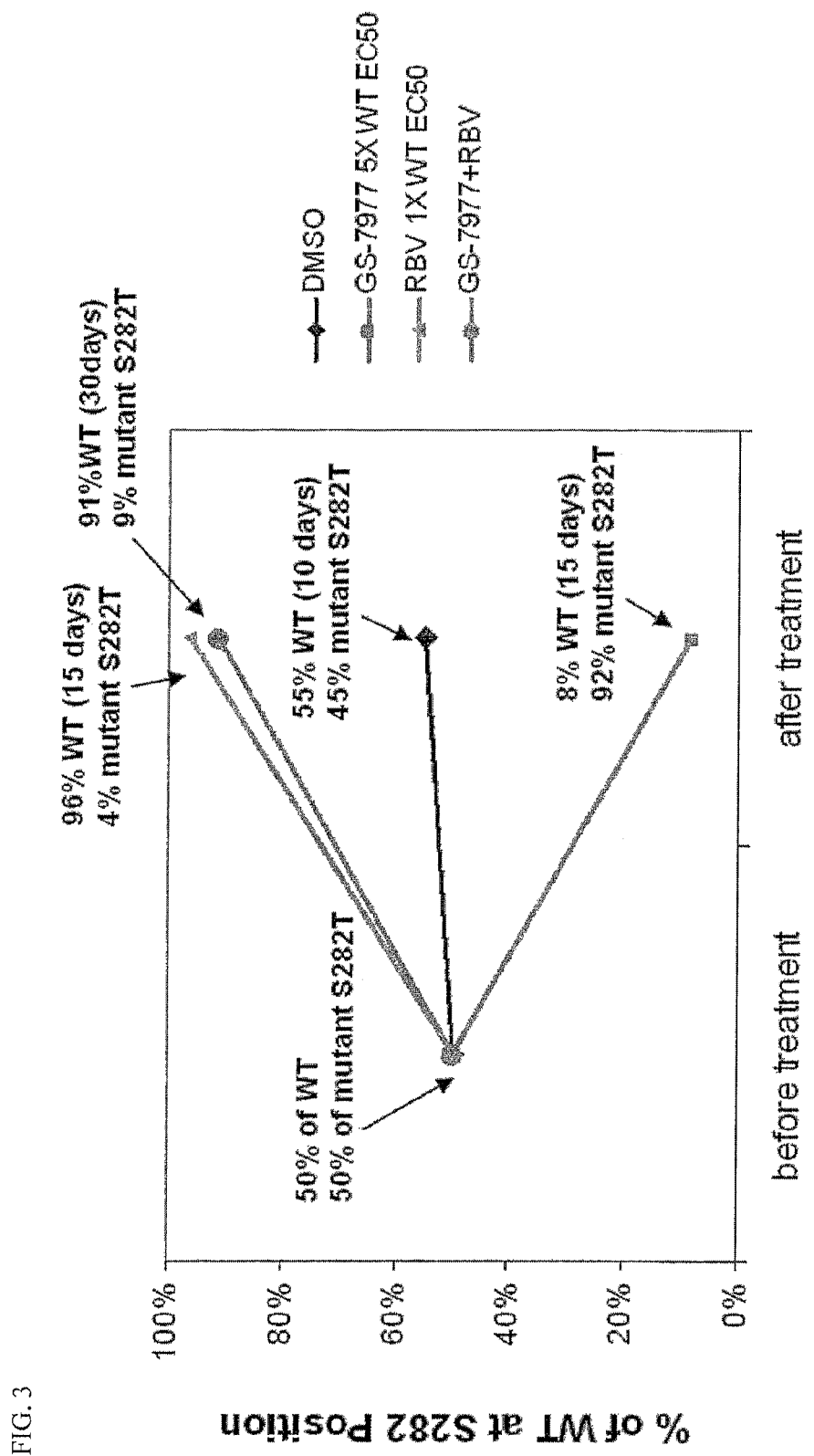
FIG. 3. Percentage of wild-type at S282 position in HCV replicons before and after treatment with GS-7977, ribavirin, and a combination of GS-7977 and ribavirin in long-term passaging study (15-30 days).

A long-term passaging study in GT 2a replicons revealed that GS-7977 alone displayed greater inhibition of WT than S282T, resulting in a population that was 92% mutant S282T over fifteen days. Ribavirin alone suppressed S282T more than WT, resulting in a population that was 96% WT after fifteen days. The combination of GS-7977 and ribavirin also preferentially inhibited S282T over WT, resulting in a population that was 91% WT following thirty days of treatment. The results of the passaging study are presented in FIG. 3. (See also Han et al., 63$^{rd}$ Annual Meeting of the American Association for the Study of Liver Diseases, Poster 1078, Nov. 11, 2012.)

Thus, while the S282T replicon has been shown to confer reduced susceptibility to GS-7977 in vitro, the mutant replicon has demonstrated increased susceptibility to ribavirin over the wile-type, suggesting that treatment of CHC with the combination of GS-7977 and ribavirin may result in reduced viral breakthroughs and incidence of resistance compared to monotherapy with GS-7977 alone. The hypersensitivity of S282T mutants to ribavirin may provide an additional advantage to combination treatment comprising GS-7977 and ribavirin, in terms of preventing or delaying the emergency of S282T mutants.

Quantification of HCV RNA in Human Clinical Studies

Quantitative HCV RNA testing for clinical trials was performed using the Roche COBAS® AmpliPrep/COBAS® HCV TaqMan® assay using a standardized, automatic RNA extraction system and standardized controls and calibrators. The established LOD of the assay was 15 IU/mL (defined by a 95% hit rate with WHO Standards). HCV RNA levels were measured using serum samples.

US 2010/0226885 (U.S. Ser. No. 12/376,180), which is incorporated by reference, also discloses a method for measuring whether a patient has achieved an HCV negative status using RT-PCR to measure HCV RNA levels.

Treatment Regimens—P7977-0221 and PROTON Clinical Studies

A Phase 2a, 3-cohort placebo-controlled study (P7977-0221) evaluated treatment with GS-7977 (100 mg, 200 mg or 400 mg QD) in combination with peginterferon and ribavirin in treatment-naïve GT1 HCV subjects for 4 weeks, followed by up to an additional 44 weeks of treatment with SOC peginterferon and ribavirin. High RVR (88-94%) was observed for all three GS-7977 treatment groups. Following discontinuation of GS-7977, the durability of antiviral response (SVR-12 and SVR-24) was greatest in the 400 mg treatment group (86.7% and 80.0%, respectively). SVR-12 and SVR-24 rates were 72.2% and 83.3%, respectively, for patients receiving a 200 mg GS-7977 treatment regimen, and the majority of GS-7977-treated patients who failed to achieve SVR received a 100 mg QD dose of GS-7977.

The Phase 2b PROTON study evaluated treatment with a combination of GS-7977, peginterferon, and ribavirin at daily dosage levels of 200 mg and 400 mg of GS-7977 for 12 weeks, followed by up to an additional 36 weeks of treatment with SOC peginterferon and ribavirin. A greater number of subjects experienced viral breakthrough after cessation of the GS-7977 200 mg dosage level while still receiving peginterferon/ribavirin treatment compared to no viral breakthroughs after cessation of the GS-7977 400 mg dosage level while still receiving peginterferon/ribavirin treatment.

The preceding studies indicate enhanced efficacy for a GS-7977 400 mg daily dose level compared to a 200 mg daily dose level.

Treatment Regimens—ELECTRON Clinical Study

The ongoing Phase 2a ELECTRON clinical study evaluated GS-7977 400 mg QD for 8 or 12 weeks in combination with or without ribavirin and/or peginterferon in subjects with GT1, GT2 or GT3 HCV infection. Preliminary data demonstrates 100% SVR-12 for treatment-naïve GT2 or GT3 HCV patients treated with a combination of GS-7977 and ribavirin, regardless of the presence of peginterferon, as well as 84% SVR-12 for treatment-naïve GT1 HCV patients receiving combination treatment with GS-7977 and ribavirin. In comparison, only 60% of treatment-naïve GT2/GT3 HCV patients receiving GS-7977 monotherapy achieved SVR-12.

Part 1 of the ELECTRON trial evaluated 12-week regimens of GS-7977 400 mg QD in combination with ribavirin (RBV) only (1000/12000 mg by weight BID) and, in separate arms, with abbreviated durations of peginterferon for 4, 8, or 12 weeks in treatment-naïve patients with HCV GT2 or GT3:

Group 1: GS-7977 (400 mg QD) with RBV (1000/1200 mg BID) for 12 weeks (no peginterferon) (GT2/GT3 treatment-naïve); and Groups 2, 3, 4: GS-7977 (400 mg QD) with RBV (1000/1200 mg BID) for 12 weeks and PEG (180 µg weekly) weeks 1-4 only/PEG (180 µg weekly) weeks 1-8 only/PEG (180 µg weekly) weeks 1-12 (GT2/GT3 treatment-naïve).

In Part 2 of the ELECTRON trial, an additional 30 patients were enrolled in exploratory regimens of GS-7977 monotherapy and abbreviated durations of total therapy with the combination of GS-7977, RBV and PEG:

Group 5: GS-7977 (400 mg QD) monotherapy for 12 weeks (GT2/GT3 treatment-naïve);

Group 6: GS-7977 (400 mg QD) with PEG (180 µg weekly) and RBV (1000/1200 mg BID) for 8 weeks (GT2/GT3 treatment-naïve); and Group 7: GS-7977 (400 mg QD) with RBV (1000/1200 mg BID) for 12 weeks (GT1 null responders).

In Part 3 of the ELECTRON trial, two additional peginterferon-free regimens were explored in treatment-naïve patients with HCV GT1 and treatment-experienced patients with HCV GT2 or HCV GT3:

Group 8: GS-7977 (400 mg QD) with RBV (1000/1200 mg BID) for 12 weeks (GT1 treatment-naïve); and Group 9: GS-7977 (400 mg QD) with RBV (1000/1200 mg BID) for 12 weeks (GT2/GT3 treatment-experienced).

In Part 4 of the ELECTRON trial, two further peginterferon-free regimens were added:

Group 10: GS-7977 (400 mg QD) with RBV (1000/1200 mg BID) for 8 weeks (GT2/GT3 treatment-naïve); and Group 11: GS-7977 (400 mg QD) with RBV (800 mg BID) for 12 weeks (GT2/GT3 treatment-naïve).

Null responders were defined as patients with <2 $\log_{10}$ IU/mL decline from baseline HCV RNA after at least 12 weeks of treatment with peginterferon and ribavirin.

Treatment-experienced patients were defined as those who had any of the following responses after at least 12 weeks of treatment with peginterferon and ribavirin: (1)<2 $\log_{10}$ IU/mL decline from baseline HCV RNA, (2)≥$\log_{10}$ IU/mL reduction in HCV RNA, but HCV RNA> limit of quantitation ("LOQ") at end of treatment, and (3) HCV RNA<LOQ at end of treatment but subsequent HCV RNA>LOQ (relapsers).

The preliminary results of the ELECTRON trial are presented below.

The patient population and demographics for ELECTRON Groups 1-9 are summarized in Tables 8A and 8B, below.

TABLE 8A

| | ELECTRON Patient Demographics (Groups 1-5) | | | | |
|---|---|---|---|---|---|
| | GS-7977 RBV NO PEG | GS-7977 RBV 4 Wks PEG | GS-7977 RBV 8 Wks PEG | GS-7977 RBV 12 Wks PEG | GS-7977 NO RBV NO PEG |
| | GT2/GT3 Tx-Naive | | | | |
| | (Group 1) | (Groups 2, 3, 4) | | | (Group 5) |
| Number (N) | 10 | 9 | 10 | 11 | 10 |
| Male (n, %) | 8 (80) | 5 (56) | 5 (50) | 9 (82) | 4 (40) |
| Race (Caucasian, %) | 7 (70) | 4 (44) | 8 (80) | 8 (73) | 7 (70) |
| Age (Mean, range) | 47 (35-53) | 47 (29-66) | 49 (29-66) | 46 (22-57) | 43 (22-57) |
| BMI (Mean, range) ($kg/m^2$) | 28 (23.7-35.7) | 26 (21.3-32.2) | 25 (18.1-32.5) | 24 (20.8-28.4) | 26 (18.2-39.4) |
| HCV RNA (Mean, SD) ($\log_{10}$ IU/mL) | 6.7 (0.42) | 6.6 (0.52) | 6.4 (0.57) | 6.3 (0.76) | 5.7 (0.89) |
| HCV RNA (Median, range) | 6.7 (6.6-7.3) | 6.6 (5.8-7.3) | 6.4 (5.1-7.0) | 6.4 (5.2-7.1) | 5.7 (4.6-7.3) |
| HCV GT-2:GT-3 | 4:6 | 3:6 | 4:6 | 4:7 | 3:7 |

TABLE 8A-continued

| ELECTRON Patient Demographics (Groups 1-5) | | | | | |
|---|---|---|---|---|---|
| | GS-7977 RBV NO PEG | GS-7977 RBV 4 Wks PEG | GS-7977 RBV 8 Wks PEG | GS-7977 RBV 12 Wks PEG | GS-7977 NO RBV NO PEG |
| IL28B CC/CT/TT | 5/4/1 | 4/4/1 | 4/4/2 | 4/5/2 | 2/6/2 |
| IL28B CC (n, %) | 5 (50) | 4 (44) | 4 (40) | 4 (36) | 2 (20) |

TABLE 8B

| ELECTRON Patient Demographics (Groups 6-9) | | | | |
|---|---|---|---|---|
| | GS-7977 RBV PEG 8 Wks GT2/GT3 Tx-Naive (Group 6) | GS-7977 RBV NO PEG 12 Wks Null (Group 7) | GS-7977 RBV NO PEG 12 Wks GT1 Tx-Naive (Group 8) | GS-7977 RBV NO PEG 12 Wks GT2/GT3 Tx-Experienced (Group 9) |
| Number (N) | 10 | 10 | 25 | 25 |
| Male (n, %) | 50 | 70 | 60 | 76 |
| Race (Caucasian, %) | 70 | 90 | 80 | 68 |
| BMI (Mean, range) | 24.8 (21-34.9) | 28.1 (19.5-35.7) | 25.6 (19.3-37.6) | 26.8 (19.2-40.0) |
| HCV RNA (Mean, SD) ($\log_{10}$ IU/mL) | 6.1 (4.3-7.3) | 6.8 (5.6-7.5) | 6.1 (4.4-7.2) | 6.5 (4.8-7.7) |
| GT 1a (%) | n/a | 90 | 88 | n/a |
| GT 3 (%) | 100 | n/a | n/a | 76 |
| IL28B CC/CT/TT | 3/6/1 | 2/5/3 | 11/12/2 | 11/12/2 |
| IL28B CC (n, %) | 3 (30) | 2 (20) | 11 (44) | 11 (44) |

A summary of the patient results for treatment-naïve HCV GT2/GT3 Groups 1-5 as related to the percentage of patients having an amount of HCV RNA below the limits of detection (LOD) is provided in Table 9.

TABLE 9

| ELECTRON Groups 1-5 Patient Results | | | | | | | | | |
|---|---|---|---|---|---|---|---|---|---|
| | GS-7977 RBV NO PEG (Group 1) | | GS-7977 RBV 4 wks PEG | | GS-7977 RBV 8 wks PEG[a] | | GS-7977 RBV 12 weeks PEG[a] | | GS-7977 NO RBV NO PEG (Group 5) |
| | | | | (Groups 2, 3, 4) | | | | | |
| Time (Wks) | n/N | % < LOD | n/N | % < LOD | n/N | % < LOD | n/N | % < LOD | n/N | % < LOD |
| 0 | 0/10 | 0 | 0/9 | 0 | 0/10 | 0 | 0/11 | 0 | 10/0 | 0 |
| 4 | 10/10 | 100 | 9/9 | 100 | 10/10 | 100 | 11/11 | 100 | 10/10 | 100 |
| 8 | 10/10 | 100 | 9/9 | 100 | 10/10 | 100 | 11/11 | 100 | 10/10 | 100 |
| 12 | 10/10 | 100 | 9/9 | 100 | 10/10 | 100 | 11/11 | 100 | 10/10 | 100 |
| SVR-4 | 10/10 | 100 | 9/9 | 100 | 10/10 | 100 | 11/11 | 100 | 6/10 | 60 |
| SVR-8 | 10/10 | 100 | 9/9 | 100 | 10/10 | 100 | 11/11 | 100 | 6/10 | 60 |
| SVR-12 | 10/10 | 100 | 9/9 | 100 | 10/10 | 100 | 11/11 | 100 | 6/10 | 60 |
| SVR-24 | 10/10 | 100 | 9/9 | 100 | 10/10 | 100 | 11/11 | 100 | 6/10 | 60 |

From Table 9 it can be seen that all treatment-naïve HCV GT2 and GT3 patients treated with GS-7977 and RBV for 12 weeks (Groups 1-4) had no detectable amount of HCV RNA during the entire treatment period (with or without PEG). All such patients treated with a combination of GS-7977 and RBV (with or without PEG) had no detectable amount of HCV RNA at 12 weeks and at 24 weeks after the termination of treatment.

Table 9 also reveals that all HCV GT2/GT3 treatment-naïve patients receiving 12 weeks of GS-7977 (400 mg QD) monotherapy (Group 5) had no detectable amount of HCV RNA during the entire treatment period. However, only 60% of the patients receiving GS-7977 monotherapy achieved SVR-12 and SVR-24.

Comparing Group 1 (GS-7977+RBV) with Group 5 (GS-7977 monotherapy), the combination of GS-7977 and ribavirin appears to provide a synergistic increase in SVR-4, SVR-8, SVR-12 and SVR-24 rates, as ribavirin alone has been reported to have little to no effect on HCV RNA levels.

Table 10 provides the mean HCV RNA values ($\log_{10}$ IU/mL) for treatment-naive HCV GT2/GT3 patients (N=10) for time of treatment (12 weeks) up to 12 weeks after treatment (W24) for patients receiving a combination of 400 mg QD of GS-7977 and 1000/1200 mg BID (based on weight) of RBV (Group 1). Table 10 also provides the mean HCV RNA values ($\log_{10}$ IU/mL) for treatment-naïve HCV GT2/GT3 patients (N=10) for the time of treatment (12 weeks) for patients receiving a 12-week regimen of 400 mg QD of GS-7977 only (Group 5). The terms "D1 (6 hr)" and "D1 (12 hr)" refer to the recorded measurements made 6 hrs and 12 hrs, respectively, on day 1 following day 1 dosing. The data presented in Table 10 is also illustrated in FIG. 1.

TABLE 10

| ELECTRON Groups 1 and 5 HCV RNA values($\log_{10}$ IU/mL) | | |
|---|---|---|
| | HCV RNA ($\log_{10}$ IU/mL) | |
| Time | GS-7977 RBV (Group 1) | GS-7977 NO RBV (Group 5) |
| T = 0[a] | 6.79 | 6.08 |
| D1 | 6.67 | 5.74 |

TABLE 10-continued

ELECTRON Groups 1 and 5 HCV RNA values(log₁₀ IU/mL)

| Time | HCV RNA (log₁₀ IU/mL) | |
|---|---|---|
| | GS-7977 RBV (Group 1) | GS-7977 NO RBV (Group 5) |
| D1 (6 hr)[b] | 6.65 | 5.63 |
| D1 (12 hr)[c] | 5.86 | 4.98 |
| D2 | 4.50 | 3.75 |
| D3 | 3.41 | 2.62 |
| W1 | 2.16 | 1.56 |
| W2 | 1.36 | 1.22 |
| W3 | 1.18 | 1.15 |
| W4 | 1.15 | 1.15 |
| W5 | 1.15 | 1.15 |
| W6 | 1.15 | 1.15 | value is below the limit of detection during weeks 3-12 of the treatment period for patients receiving GS-7977 monotherapy. However, Table 10 and FIG. 1 also illustrate that patients who received a combination of GS-7977 and ribavirin for 12 weeks (Group 1) maintained lower mean HCV RNA levels for the 12 weeks following cessation of treatment compared to patients who received monotherapy with GS-7977 (Group 5).

These results demonstrate that the combination of GS-7977 and ribavirin is advantageous in that patients can be treated for HCV without receiving peginterferon treatment and achieve a high rate of SVR-12.

A summary of the preliminary patient results for all nine fully reported cohorts of the ELECTRON trial as related to the percentage of patients having an amount of HCV RNA below the limits of detection (LOD) is summarized in Table 11.

TABLE 11

ELECTRON Groups 1-9 Patient Results

| | Genotype 2/3 Treatment Naive | | | | Genotype 1 Null Responders | Genotype 1 | Genotype 2/3 Treatment Experienced |
|---|---|---|---|---|---|---|---|
| Time (Wks) | GS-7977 RBV NO PEG 12 wks (Group 1) (N = 10) n (%) | GS-7977 RBV PEG 12 wks (Groups 2, 3, 4) (N = 30) n (%) | GS-7977 NO RBV NO PEG 12 weeks (Group 5) (N = 10) n (%) | GS-7977 RBV PEG 8 weeks (Group 6) (N = 10) n (%) | GS-7977 RBV NO PEG 12 weeks (Group 7) (N = 10) n (%) | GS-7977 RBV NO PEG 12 weeks (Group 8) (N = 25) n (%) | GS-7977 RBV NO PEG 12 weeks (Group 9) (N = 25) n (%) |
| 0 | 0 | 0 | 0 | 0 | 0 | 0 | 0 |
| 1 | 2 (20) | 8 (27) | 5 (50) | 6 (60) | 1 (10) | 8 (32) | 8 (32) |
| 2 | 8 (80) | 23 (77) | 8 (80) | 10 (100) | 7 (70) | 17 (68) | 21 (84) |
| 3 | 9 (90) | 25 (83) | 10 (100) | 10 (100) | 10 (100) | 22 (88) | 25 (100) |
| 4 | 10 (100) | 30 (100) | 10 (100) | 10 (100) | 10 (100) | 25 (100) | 25 (100) |
| 8 | 10 (100) | 30 (100) | 10 (100) | N/A | 10 (100) | 25 (100) | 25 (100) |
| 12 | 10 (100) | 30 (100) | 10 (100) | 10 (100) | 10 (100) | 25 (100) | 25 (100) |
| SVR-4 | 10 (100) | 30 (100) | 6 (60) | 10 (100) | 1 (10) | 22 (88) | 19 (76) |
| SVR-12 | 10 (100) | 30 (100) | 6 (60) | 10 (100) | 1 (10) | 21 (84) | 17 (68) |

TABLE 10-continued

ELECTRON Groups 1 and 5 HCV RNA values(log₁₀ IU/mL)

| Time | HCV RNA (log₁₀ IU/mL) | |
|---|---|---|
| | GS-7977 RBV (Group 1) | GS-7977 NO RBV (Group 5) |
| W7 | 1.15 | 1.15 |
| W8 | 1.15 | 1.15 |
| W9 | 1.15 | 1.15 |
| W10 | 1.15 | 1.15 |
| W11 | 1.15 | 1.15 |
| W12 | 1.15 | 1.15 |
| W14 | 1.15 | 1.66 |
| W16 | 1.15 | 2.95 |
| W20 | 1.15 | 3.12 |
| W24 | 1.15 | 3.17 |

[a]Initial Screening Values for patients.
[b]Day 1 results 6 hrs after dosing.
[c]Day 1 results 12 hrs after dosing.

The data in Table 10 and FIG. 1 clearly show that treatment of HCV GT2/GT3 treatment-naïve patients with a combination of GS-7977 and RBV (in the amounts noted above) results in mean HCV RNA levels below the limit of detection during weeks 4-12 of the treatment period, as well as SVR-12. This data also shows that the mean HCV RNA The data in Table 11 demonstrate an SVR-12 rate of 100% for treatment-naïve patients with HCV GT2/GT3 (Groups 1-4, 6) when treated with a combination of GS-7977 (400 mg QD) and RBV, regardless of the presence of peginterferon. The data in Table 11 also demonstrates an SVR-12 rate of 84% for patients with HCV GT1 (Group 8) treated with a combination of GS-7977 and RBV in the absence of peginterferon. In contrast, monotherapy with GS-7977 (Group 5) for GT2/GT3 treatment-naïve patients produced an SVR-12 rate of 60%.

All patients enrolled in Group 10 (8 weeks of GS-7977+ ribavirin combination therapy in treatment-naïve GT2/GT3 HCV subjects) achieved rapid virological response, and there were no discontinuations or on-treatment breakthroughs.

Treating a subject infected with HCV by administering an effective amount of GS-7977, either alone or in combination with an effective amount of RBV, means that the side-effects normally associated with peginterferon may be avoided. Table 12 presents adverse events reported in at least 15% of the subjects in any treatment group for ELECTRON Groups 1-9.

TABLE 12

ELECTRON Groups 1-9 Adverse Events Reported in at Least 15% of Subjects in Any Treatment Group

| Adverse Event | GS-7977 RBV NO PEG 12 wks N = 70 (Groups 1, 7, 8, 9) | GS-7977 PEG RBV 12 wks N = 30 (Groups 2, 3, 4) | GS-7977 NO RBV NO PEG 12 wks N = 10 (Group 5) | GS-7977 RBV PEG 8 wks N = 10 (Group 6) |
|---|---|---|---|---|
| ≥1 AE: n (%) | 69 (99) | 30 (100) | 10 (100) | 10 (100) |
| Blood and Lymphatic System Disorders | 10 (14) | 10 (33) | 0 | 3 (30) |
| Anemia | 3 (4) | 5 (17) | 0 | 3 (30) |
| Gastrointestinal Disorders | 32 (46) | 17 (57) | 8 (80) | 7 (70) |
| Nausea | 18 (26) | 9 (30) | 3 (30) | 2 (20) |
| Diarrhoea | 10 (14) | 4 (13) | 0 | 3 (30) |
| Abdominl Pain | 1 (1) | 1 (3) | 0 | 2 (20) |
| Flatulence | 1 (1) | 0 | 0 | 2 (20) |
| General Disorders and Administration Site Conditions | 43 (61) | 22 (73) | 8 (80) | 10 (100) |
| Fatigue | 27 (39) | 11 (37) | 3 (30) | 7 (70) |
| Irritability | 8 (11) | 5 (17) | 1 (10) | 2 (20) |
| Pyrexia | 1 (1) | 4 (13) | 0 | 5 (50) |
| Pain | 1 (1) | 2 (7) | 0 | 2 (20) |
| Chills | 0 | 2 (7) | 0 | 2 (20) |
| Injection Site Erythema | 0 | 1 (3) | 0 | 2 (20) |
| Axillary Pain | 0 | 0 | 2 (20) | 0 |
| Infections and Infestations | 33 (47) | 12 (40) | 5 (50) | 6 (60) |
| Upper Respiratory Tract Infection | 11 (16) | 3 (10) | 2 (20) | 1 (10) |
| Metabolism and Nutrition Disorders | 5 (7) | 11 (37) | 0 | 50 (50) |
| Decreased Appetite | 4 (6) | 5 (17) | 0 | 50 (50) |
| Musculoskeletal and Connective Tissue Disorders | 23 (33) | 19 (63) | 2 (20) | 7 (70) |
| Myalgia | 10 (14) | 9 (30) | 1 (10) | 4 (40) |
| Back Pain | 3 (4) | 4 (13) | 1 (10) | 2 (20) |
| Arthralgia | 4 (6) | 5 (17) | 0 | 1 (10) |
| Nervous System Disorders | 40 (57) | 26 (87) | 9 (90) | 7 (70) |
| Headache | 28 (40) | 24 (80) | 8 (80) | 6 (60) |
| Dizziness | 7 (10) | 9 (30) | 2 (20) | 1 (10) |
| Dizziness Postural | 0 | 0 | 0 | 2 (20) |
| Psychiatric Disorders | 26 (37) | 23 (77) | 6 (60) | 5 (50) |
| Insomnia | 15 (21) | 16 (53) | 6 (60) | 1 (10) |
| Respiratory, Thoracic and Mediastinal Disorders | 18 (26) | 15 (50) | 3 (30) | 5 (50) |
| Oropharyngeal Pain | 5 (7) | 3 (10) | 2 (20) | 1 (10) |
| Dyspnoea | 2 (3) | 5 (17) | 0 | 1 (10) |
| Skin and Subcutaneous Tissue Disorders | 31 (44) | 25 (83) | 3 (30) | 8 (80) |
| Rash | 16 (23) | 9 (30) | 1 (10) | 5 (50) |
| Pruritus | 4 (6) | 8 (27) | 0 | 2 (20) |
| Dry Skin | 7 (10) | 5 (17) | 0 | 2 (20) |
| Alopecia | 0 | 5 (17) | 0 | 1 (10) |

The data in Table 12 reveal that lower incidence rates (%) were reported for a number of types of adverse events for treatment regimens involving the combination of GS-7977 and ribavirin (Groups 1, 7, 8, 9) compared to treatment regimens also involving peginterferon (Groups 2, 3, 4). For example, reduced rates of the following adverse events were reported for the interferon-free treatment regimens combining GS-7977 and ribavirin: blood and lymphatic system disorders (including anemia); pain and chills; metabolism and nutrition disorders (including decreased appetite); musculoskeletal and connective tissue disorders (including myalgia, back pain and arthralgia); nervous system disorders (including headache and dizziness); psychiatric disorders (including insomnia); respiratory, thoracic and mediastinal disorders (including dyspnoea); and skin and subcutaneous tissue disorders (including pruritis, dry skin and alopecia).

The data in Table 13, below, reveals reduced frequencies of Grade 3 and Grade 4 hematologic abnormalities for interferon-free Groups 1, 5, 7, 8 and 9 compared to Groups 2, 3, 4 and 6 receiving treatment regimens including peginterferon:

TABLE 13

| Laboratory Abnormalities | GS-7977 RBV NO PEG 12 wks (Group 1) (N = 10) n (%) | GS-7977 RBV PEG 12 wks (Groups 2, 3, 4) (N = 30) n (%) | GS-7977 NO RBV NO PEG 12 weeks (Group 5) (N = 10) n (%) | GS-7977 RBV PEG 8 weeks (Group 6) (N = 10) n (%) | GS-7977 RBV NO PEG 12 weeks (Group 7) (N = 10) n (%) | GS-7977 RBV NO PEG 12 weeks (Group 8) (N = 25) n (%) | GS-7977 RBV NO PEG 12 weeks (Group 9) (N = 25) n (%) |
|---|---|---|---|---|---|---|---|
| Alanine aminotransferase | | | | | | | |
| Grade 3 | 0 | 1 (3) | 0 | 0 | 0 | 1 (4) | 0 |
| Hemoglobin | | | | | | | |
| Grade 3 | 0 | 1 (3) | 0 | 1 (10) | 1 (10) | 0 | 0 |
| Lymphocytes | | | | | | | |
| Grade 3 | 0 | 3 (10) | 0 | 0 | 0 | 0 | 0 |
| Grade 4 | 0 | 0 | 1 (10) | 0 | 0 | 1 (4) | 0 |
| Neutropenia | | | | | | | |
| Grade 3 | 0 | 5 (17) | 0 | 2 (20) | 0 | 0 | 0 |
| Grade 4 | 0 | 5 (17) | 0 | 0 | 0 | 0 | 0 |
| White blood cells | | | | | | | |
| Grade 3 | 0 | 6 (20) | 0 | 0 | 0 | 0 | 0 |
| INR | | | | | | | |
| Grade 3 | 1 (10) | 0 | 0 | 0 | 1 (10) | 0 | 0 |

Additional results, not shown here, show a rapid normalization of ALT levels in all patients in ELECTRON Groups 1-5 during the treatment period (12 weeks), and to the extent of available data, for periods after the end of the treatment period.

GS-7977 Resistance in Human Clinical Studies

To date, no virologic breakthrough has been observed during treatment with GS-7977, suggesting a high barrier to resistance. Across the P7977-0221, PROTON, ELECTRON (Groups 1-9) and ATOMIC Phase 2 human clinical studies of treatment regimens involving GS-7977 alone or in combination with ribavirin and/or peginterferon, 53 out of 621 patients have experienced viral relapse after cessation of GS-7977-containing treatment. Population sequencing of the viral relapse samples showed that S282T was detected in only one of the 53 patients, who was GT2b and relapsed 4 weeks after completion of 12 weeks of GS-7977 monotherapy. Deep sequencing revealed 99% S282T in this GT2b patient at relapse. Population and clonal phenotypic analysis demonstrated that the GT2b S282T-containing sample was 8- to 13-fold less susceptible to GS-7977 compared to corresponding baseline virus. For the other 52 patients experiencing relapse, deep sequencing at baseline and relapse showed no S282T, and no specific NS5B mutation at other residues was identified by population or deep sequencing as being associated with GS-7977 resistance. (See also Svarovskaia et al., 63rd Annual Meeting of the American Association for the Study of Liver Diseases, Poster 753, Nov. 11, 2012.)

The foregoing illustrates that GS-7977 has a high resistance barrier. Notably, the S282T mutation has not been observed in any patient receiving a treatment regimen combining GS-7977 and ribavirin.

Concordance of SVR-4 with SVR-12 and SVR-24 for Treatment Regimens Combining GS-7977 with Ribavirin and Optionally Peginterferon Florian et al. have reported that SVR-12 and SVR-24 were concordant across a large population database of HCV clinical trials including trials involving peginterferon/ribavirin combination treatment and treatment regimens combining peginterferon, ribavirin and telaprevir or boceprevir, with SVR-12 having a positive predictive value of 98% for SVR-24. (Florian et al., AASLD 2011, Abstract LB-28; see also Martinot-Peignoux et al., Hepatology (2010) 51(4): 1122-1126.)

HCV data from treatment-naive GT1, GT2 and GT3 patients in the PROTON, ELECTRON and ATOMIC Phase 2 studies who received at least 12 weeks of treatment with GS-7977, either alone or in combination with ribavirin and optionally peginterferon, were evaluated. Only patients treated for at least 12 weeks with 400 mg GS-7977 who had SVR-4 and SVR-12 or SVR-4 and SVR-24 data were included in the analysis (259 of 596 patients). The analysis found 99-100% concordance between SVR-4 and both SVR-12 and SVR-24 across all regimens for patients who achieved SVR-4 and for whom post-treatment week 12 data were available. These results show that SVR-4 is highly concordant with SVR-12 and SVR-24 for GT1, GT3 and GT3 HCV patients treated with 400 mg GS-7977 and ribavirin, and optionally with peginterferon. (Lawitz et al., GS-7977 Phase 2 Trials: Concordance of SVR4 with SVR12 and SVR24 in HCV Genotypes 1-3, EASL (Apr. 18-22, 2012).)

The foregoing suggests that the SVR data presented herein may have predictive value for longer-term SVR rates including SVR-24, SVR-36 and SVR-48.

The compositions and unit dosage forms comprising GS-7977 disclosed herein provide good stability to moisture and degradation, as well as desirable dissolution and disintegration profiles. They may be used to treat HCV infection optionally in combination with ribavirin, peginterferon or any other antiviral agent.

Additionally, the foregoing data illustrate that GS-7977 administered in combination with ribavirin (with or without peginterferon) elicited a rapid decline in HCV RNA and end of treatment response (EOTR) in patients with HCV GT1, GT2 and GT3. No viral breakthrough has been observed during the course of treatment with GS-7977, including when combined with ribavirin and optionally peginterferon. SVR-12 was 100% for HCV GT2 and GT3 treatment-naïve patients who received a combination of GS-7977 and ribavirin for 12 weeks and 84% for HCV GT1 treatment-naïve patients who received a combination of GS-7977 and ribavirin for 12 weeks, compared to 60% SVR-12 for HCV GT2 and GT3 treatment-naïve patients who received GS-7977 alone. Given that ribavirin, alone, has been shown to have little to no effect on HCV RNA levels in human clinical trials, the foregoing clinical and in vitro data demonstrates that the combination of GS-7977 and ribavirin produces a synergistic reduction in HCV RNA levels.

Further, treatment arms in the ELECTRON trial receiving GS-7977 in combination with ribavirin, compared to treatment arms also receiving peginterferon, reported reduced incidences of side effects, suggesting that interferon-free treatment with a combination of GS-7977 and ribavirin may offer advantages over treatment regimens involving peginterferon.

Even further, in vitro results showing that HCV replicons with the S282T mutation, which show reduced susceptibility to GS-7977, display increased susceptibility to ribavirin suggest that the combination of GS-7977 and ribavirin may provide a treatment regimen resulting in reduced rates of resistance compared to monotherapy with GS-7977. Thus far, the S282T mutation has not been observed in a patient receiving GS-7977 and ribavirin combination therapy, compared to the observation of the mutation in one patient receiving GS-7977 monotherapy.

The ability to provide effective therapy without peginterferon according to the methods described herein has the potential to significantly improve therapeutic options for individuals living with HCV infection.

The foregoing description of the present invention provides illustration and description, but is not intended to be exhaustive or to limit the invention to the precise one disclosed. Modifications and variations are possible in light of the above teachings or may be acquired from practice of the invention.

What is claimed is:

1. A method of treating a human infected with hepatitis C virus comprising administering to the human a composition comprising:
   a) about 25% to about 35% w/w of a crystalline compound having the structure:

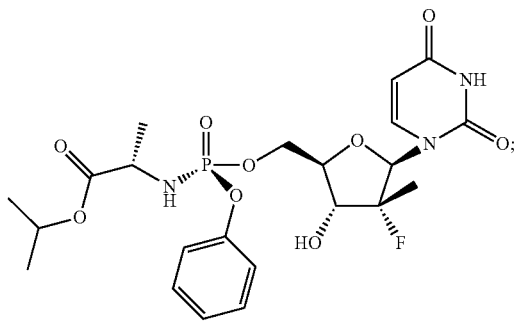 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and
   b) about 55% w/w to about 65% w/w of a diluent consisting of mannitol and microcrystalline cellulose, in combination with a daily dose of about 800 mg to about 1200 mg ribavirin,
   wherein the crystalline compound has XRPD 2θ-reflections)(°) at about: 6.1 and 12.7.

2. The method according to claim 1, wherein the method comprises administering a daily dose of about 400 mg of the crystalline compound.

3. The method according to claim 2, wherein the method comprises administering a daily dose of about 1000 mg to about 1200 mg of ribavirin.

4. The method according to claim 1, wherein the method comprises administering the crystalline compound to the human once, twice, three times or four times daily.

5. The method according to claim 1, wherein the method comprises administering ribavirin to the human once, twice, three times or four times daily.

6. The method according to claim 1, wherein the method comprises administering the crystalline compound to the human once daily.

7. The method according to claim 6, wherein the method comprises administering ribavirin to the human twice daily.

8. The method according to claim 1, wherein the method comprises administering a daily dose of about 400 mg of the crystalline compound and a daily dose of about 1000 mg to about 1200 mg of ribavirin.

9. The method according to claim 8, wherein the method comprises administering the crystalline compound to the human once daily and administering ribavirin to the human twice daily.

10. The method of claim 1, wherein the method comprises administering the crystalline compound and ribavirin to the human concurrently or alternatively.

11. The method of claim 1, wherein the method comprises administering the crystalline compound and ribavirin to the human orally.

12. The method of claim 11, wherein the method comprises administering the crystalline compound in a tablet or a capsule form.

13. The method of claim 12, wherein the method comprises administering ribavirin in a tablet or capsule form.

14. The method of claim 1, wherein the human is infected with hepatitis C virus genotype 1, 2, 3, 4, 5, or 6, or any combination thereof.

15. The method of claim 1, wherein the human is infected with hepatitis C virus genotype 2 or 3.

16. The method of claim 1, wherein the method comprises administering the composition in combination with ribavirin for a period of about 12 weeks.

17. The method of claim 1, wherein the composition further comprises:
   about 2.5% w/w to about 7.5% w/w of a disintegrant;
   about 0.25% w/w to about 0.75% w/w of a glidant; and
   about 1.25% w/w to about 1.75% w/w of a lubricant.

18. The method of claim 1, wherein the diluent consists of about 30% w/w of mannitol and about 30% w/w of microcrystalline cellulose.

19. The method of claim 1, wherein the composition comprises about 33% w/w of the crystalline compound.

20. A method of treating a human infected with hepatitis C virus comprising administering to the human a composition comprising:
   about 25% w/w to about 35% w/w of a crystalline compound having the structure:

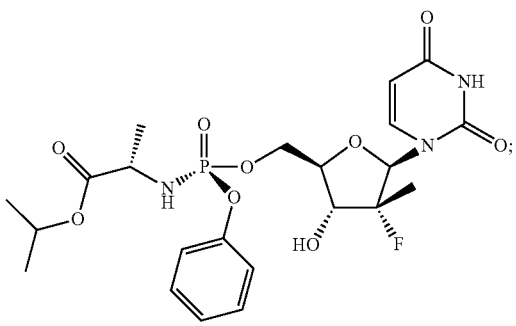 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

about 30% w/w of mannitol;
about 30% w/w of microcrystalline cellulose;
about 2.5% w/w to about 7.5% w/w of croscarmellose sodium;
about 0.25% w/w to about 0.75% w/w of colloidal silicon dioxide; and
about 1.25% w/w to about 1.75% w/w of magnesium stearate, in combination with a daily dose of about 800 mg to about 1200 mg ribavirin, wherein the crystalline compound has XRPD 2θ-reflections)(±0.2°) at about 6.1 and 12.7.

21. The method of claim 20, wherein the composition comprises:
about 33% w/w of the crystalline compound;
about 30% w/w of mannitol;
about 30% w/w of microcrystalline cellulose;
about 5% w/w of croscarmellose sodium;
about 0.5% w/w of colloidal silicon dioxide; and
about 1.5% w/w of magnesium stearate.

22. The method of claim 20, wherein the composition comprises an intragranular portion comprising:
about 33% w/w of the crystalline compound;
about 30% w/w of mannitol;
about 25% w/w of microcrystalline cellulose;
about 2.5% w/w of croscarmellose sodium;
about 0.45% w/w of colloidal silicon dioxide; and
about 0.75% w/w of magnesium stearate.

23. The method of claim 20, wherein the composition further comprises an extragranular portion comprising:
about 5% w/w of microcrystalline cellulose;
about 2.5% w/w of croscarmellose sodium;
about 0.05% w/w of colloidal silicon dioxide; and
about 0.75% w/w of magnesium stearate.

* * * * *

UNITED STATES PATENT AND TRADEMARK OFFICE
CERTIFICATE OF CORRECTION

PATENT NO.        : 9,549,941 B2
APPLICATION NO.   : 14/538736
DATED             : January 24, 2017
INVENTOR(S)       : Darryl G. Cleary et al.

Page 1 of 1

It is certified that error appears in the above-identified patent and that said Letters Patent is hereby corrected as shown below:

In the Claims

In Claim 1, Column 47, Lines 54-65, please replace

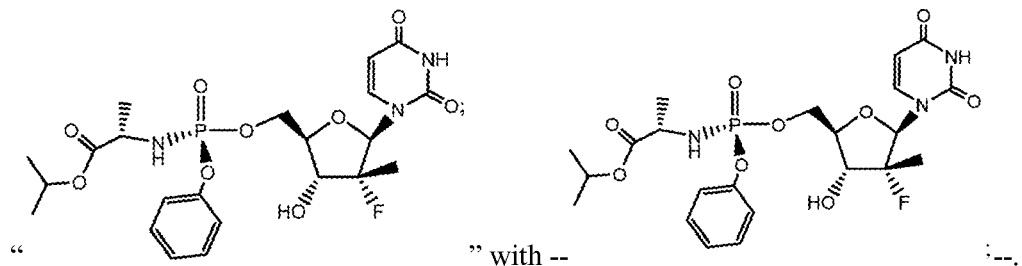

" with --                                           --.

In Claim 1, Column 48, Lines 6-7, please replace "XRPD 2θ-reflections)(°)" with
--XRPD 2θ-reflections (°)--.

In Claim 20, Column 49, Lines 1-13, please replace

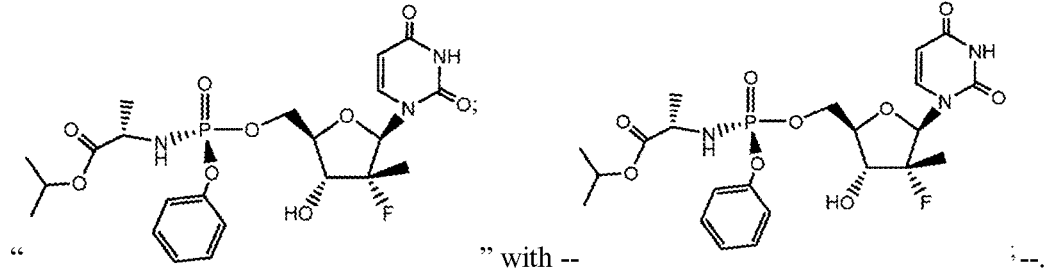

" with --                                           --.

In Claim 20, Column 49, Line 25, please replace "XRPD 2θ-reflections)(±0.2°)" with
--XRPD 2θ-reflections (±0.2°)--.

In Claim 23, Column 50, Line 18, please replace "The method of claim 20" with
--The method of claim 22--.

Signed and Sealed this
Eighth Day of May, 2018

Andrei Iancu
*Director of the United States Patent and Trademark Office*